United States Patent [19]

Gillaspey et al.

[11] Patent Number: 5,021,184
[45] Date of Patent: * Jun. 4, 1991

[54] ADAMANTANE DERIVATIVES, COMPOSITIONS OF MATTER CONTAINING SAME, PROCESSES FOR PREPARING SAID ADAMANTANE DERIVATIVES AND SAID COMPOSITIONS, AND ORGANOLEPTIC AND DEODORANCY USES OF SAID ADAMANTANE DERIVATIVES AND SAID COMPOSITIONS

[75] Inventors: William Gillaspey, Germantown, Tenn.; Myrna L. Hagedorn, Edison, N.J.; Marie R. Hanna, Keyport, N.J.; Kathleen E. Boardwick, Keyport, N.J.; Charles E. J. Beck, Summit, N.J.; Futoshi Fujioka, Oakhurst, N.J.; Anthony G. Branco, Matawan, N.J.; Anubhav Narula, Hazlet, N.J.; Richard M. Boden, Ocean, N.J.

[73] Assignee: International Flavors & Fragrances Inc., New York, N.Y.

[*] Notice: The portion of the term of this patent subsequent to Sep. 11, 2007 has been disclaimed.

[21] Appl. No.: 414,526

[22] Filed: Sep. 29, 1989

Related U.S. Application Data

[63] Continuation-in-part of Ser. No. 261,275, Oct. 21, 1988, Pat. No. 4,956,481.

[51] Int. Cl.$^5$ .................. C11D 3/50; A61K 7/46; C07C 35/22
[52] U.S. Cl. .................. 252/174.11; 131/277; 512/19; 560/256; 568/818
[58] Field of Search .................. 252/174.11; 585/352; 549/459; 568/818; 560/256; 512/19

[56] References Cited

U.S. PATENT DOCUMENTS

| 3,870,759 | 3/1975 | Inamoto et al. | 568/346 |
| 3,883,603 | 5/1975 | Inamoto et al. | 568/733 |
| 3,996,169 | 12/1976 | Light et al. | 252/522 |
| 4,036,892 | 7/1977 | Inamoto et al. | 260/617 F |
| 4,036,893 | 7/1977 | Inamoto et al. | 260/617 F |
| 4,169,958 | 10/1979 | Inamoto et al. | 568/668 |
| 4,439,354 | 3/1984 | Light et al. | 252/522 R |

FOREIGN PATENT DOCUMENTS 63-3350 2/1988 Japan .
2054557 2/1981 United Kingdom .

OTHER PUBLICATIONS

Chemical Abstracts, vol. 71, #94695w, "Perfume Compositions," NL Appl. 67 15903, 5/28/69.
Mlinaric-Majerski and Majerski, J. Am. Chem. Soc. 1983, 105, pp. 7389-7395.
Hallden-Abberton, J. Org. Chem., vol. 46, 3, 1981, pp. 538-546.

(List continued on next page.)

Primary Examiner—Paul Lieberman
Assistant Examiner—A. Beadles-Hay
Attorney, Agent, or Firm—Arthur L. Liberman

[57] ABSTRACT

Described are adamantane derivatives defined according to the generic structure:

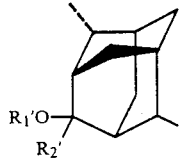

wherein $R_1'$ is hydrogen or acetyl; $R_2'$ is hydrogen or lower alkyl and the dashed line is a carbon-carbon single bond or a carbon-carbon double bond as well as uses thereof for augmenting or enhancing the aroma or taste of consumable materials selected from the group consisting of perfume compositions, perfumed articles, colognes, smoking tobacco compositions, smoking tobacco articles, deodorizing articles, doedorizing compositions and malodor maskants.

11 Claims, 39 Drawing Sheets

OTHER PUBLICATIONS

Drivas and Mison, Tetrahedron Letters, vol. 22, 1981, pp. 641–644, "Nouvelle Methode De Synthese Du Dimethyl-1,3 Adamantanol-2 Et Du Dimethyl-1,5 Adamantanol-2 Syn".

Fort and Schleyer; "Adamantane: Consequences of the Diamondoid Structure", Chem. Rev. 1964, vol. 64, p. 277.

Grob et al., Chem. Abstrs. vol. 104:148361e "Synthesis and Hydrolysis of 4-Substituted-2-Adamantyl P-Nitrobenzenesulfonates" (Abstract of Halv. Chim. Acta., 1985, 68(3), pp. 760–769.

Grob et al., Helv. Chim. Acta., 1985, 68(3), pp. 760–769.

Chem. Abstracts, vol. 76, 1972, No. 3446e "Adamantane and Its Derivatives", XXI, Derivatives of 2-Methyladamantane (Abstract of Landra et al., Collect. Czech. Chem. Commun., 1971, 36(8), pp. 3059–3065).

Chem. Abstracts, vol. 93, 1980, No. 149878v "Preparation of Adamantan-1-Ol and its Homologs" (Burkhard et al.: Abstract of Sb.Vys.Sk. Chem.-Technol. Praze, Technol., Paliv., 1978, D39, pp. 57–75.

Chem. Abstracts, vol. 93, 1980, No. 149879w, "Synthesis of Adamantane Derivatives", 60, Facile Synthesis of 2,4-Oxa-Bridged Protoadamantanes and Their Conversions to 2-Substituted and 2,4-Disubstituted Protoadamantanes and a 2,4-Disubstituted Adamantane, (Abstract of Sasaki et al., J. Org. Chem., 1980, 45(19), pp. 3824–3827).

Chem. Abstract, vol. 109:74082u, "Adamantyl Mono(-Meth)Acrylates and Their Polymers" (Abstract of Katanosaka et al., Japan Kokai Tokkyo Koho JP63/33,350 [88/33,3501], Published on Feb. 13, 1988.

FIG.5-A
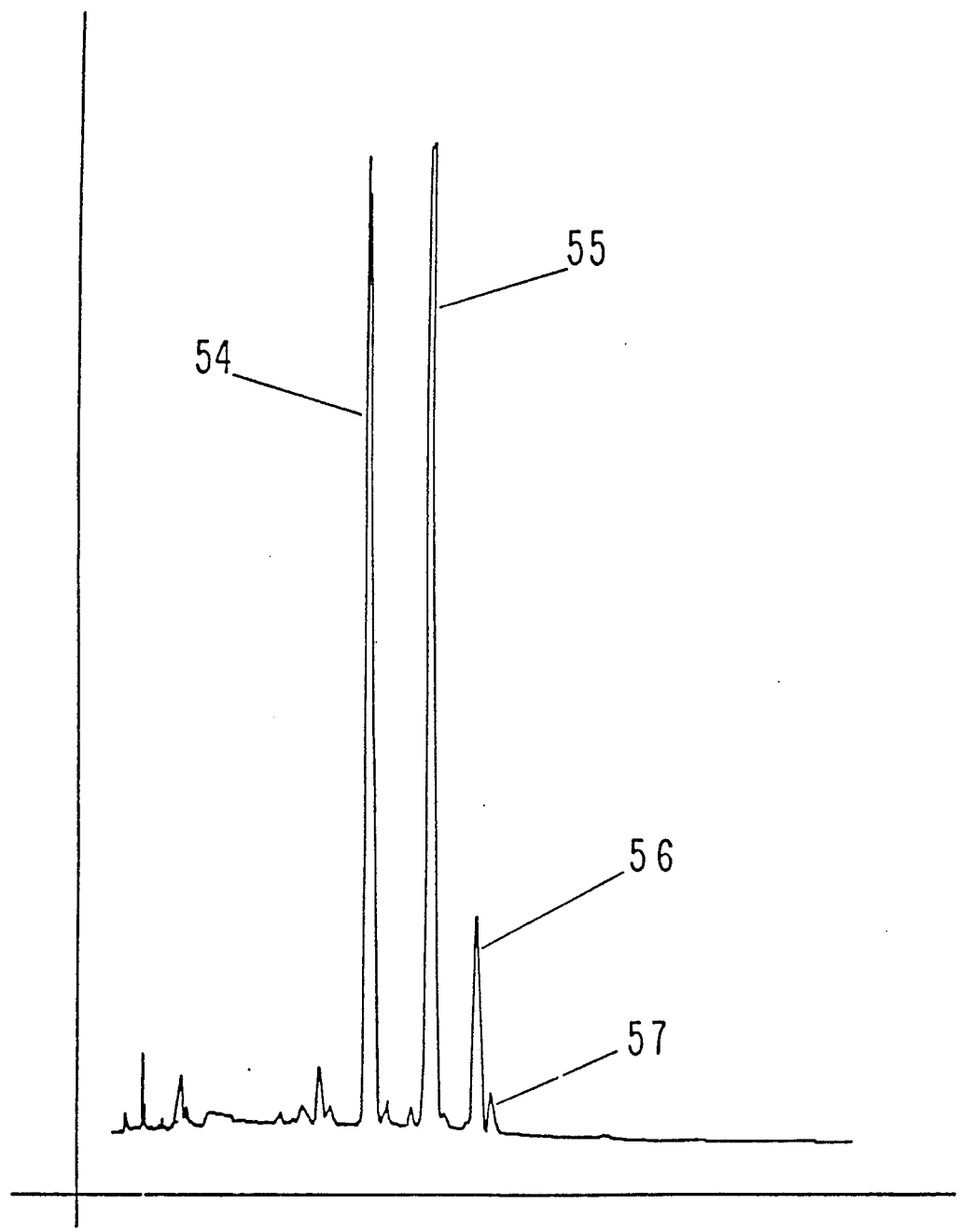

FIG.5B
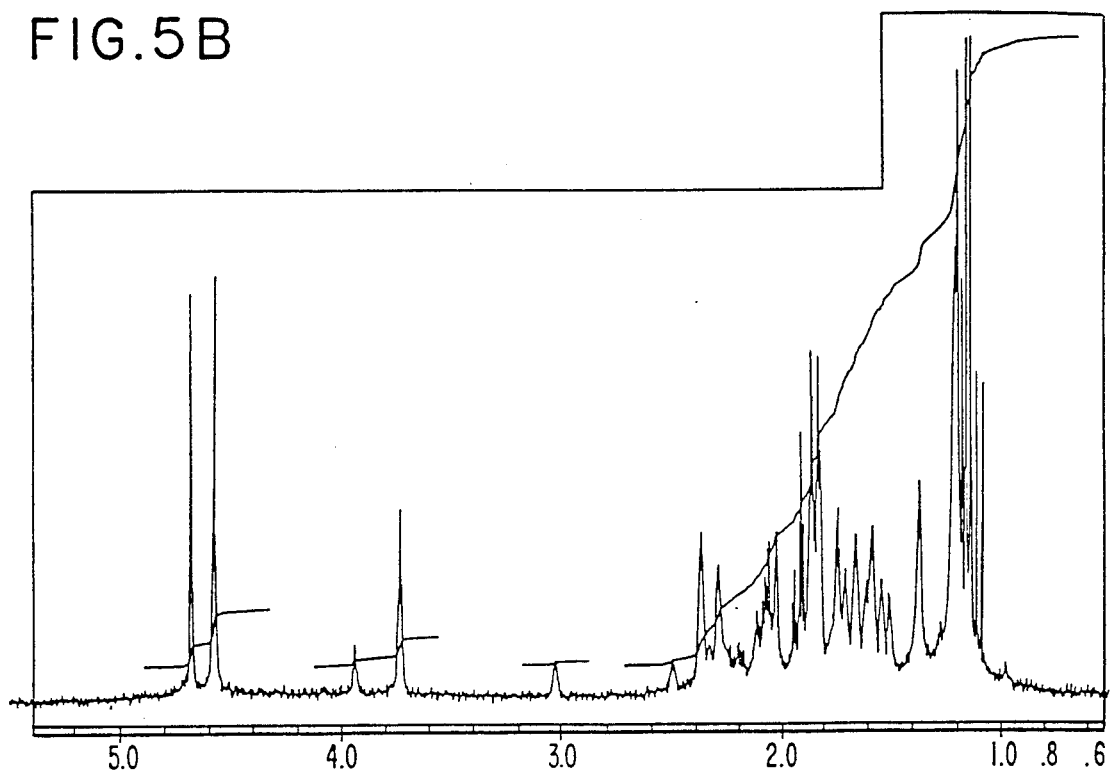
FIG.5-C
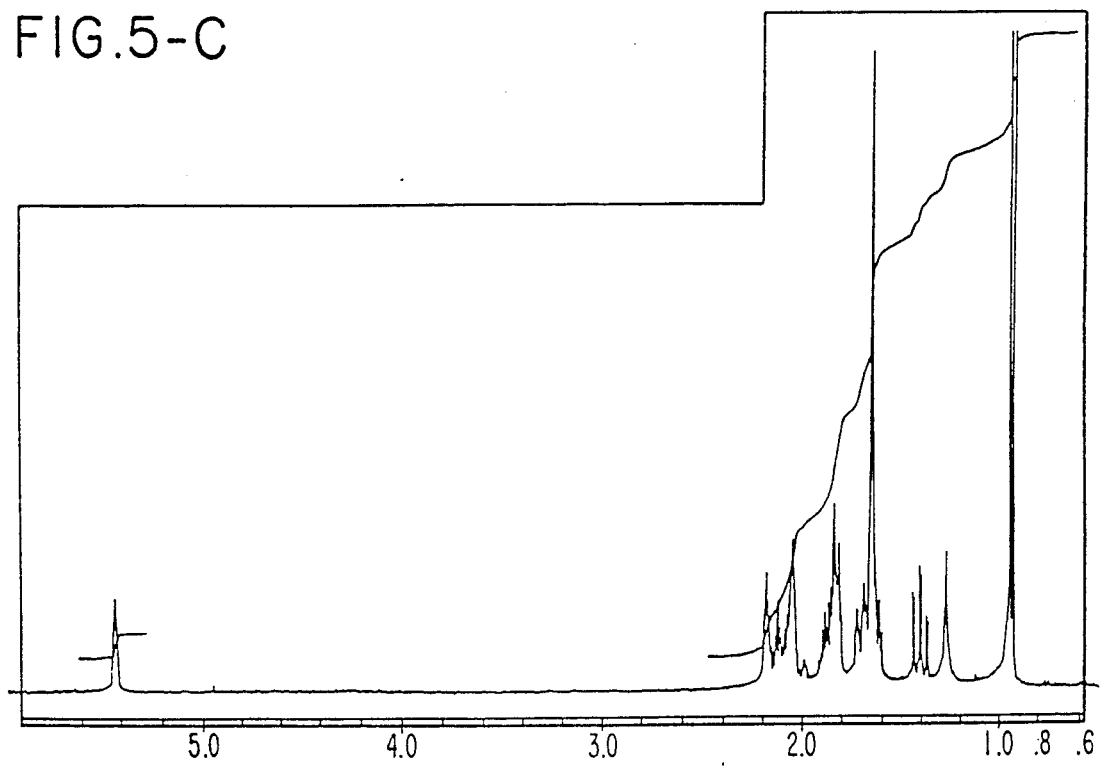

FIG.5-D
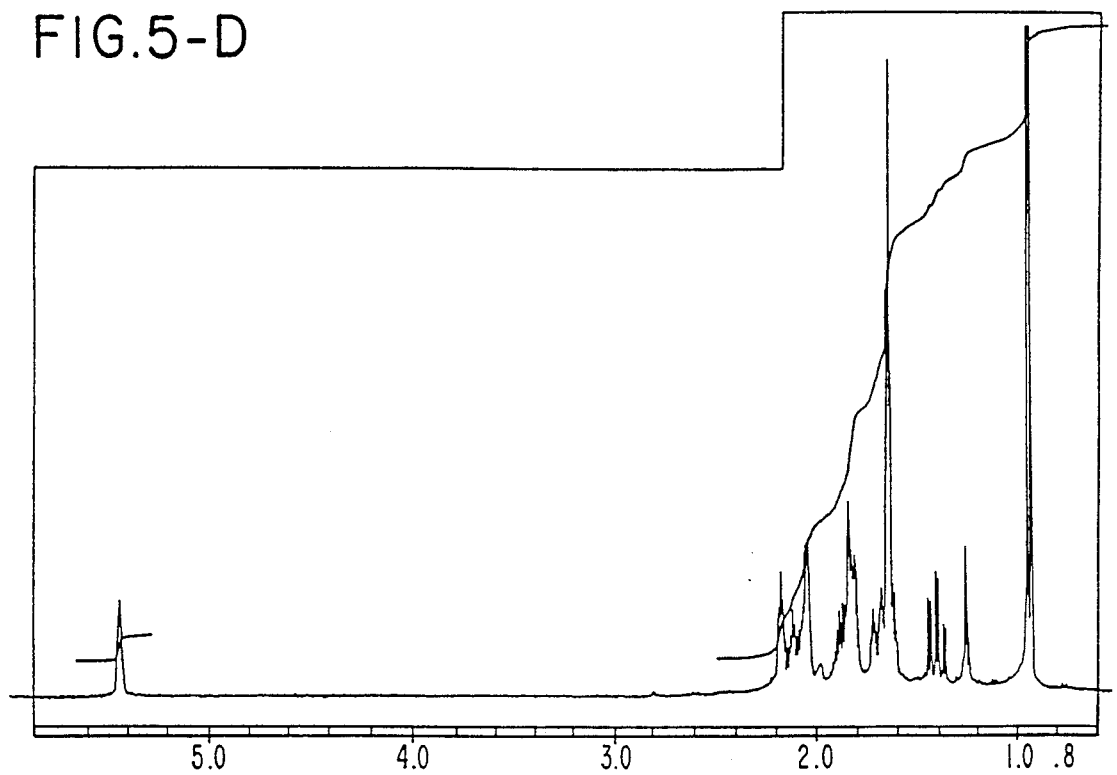
FIG.5-E
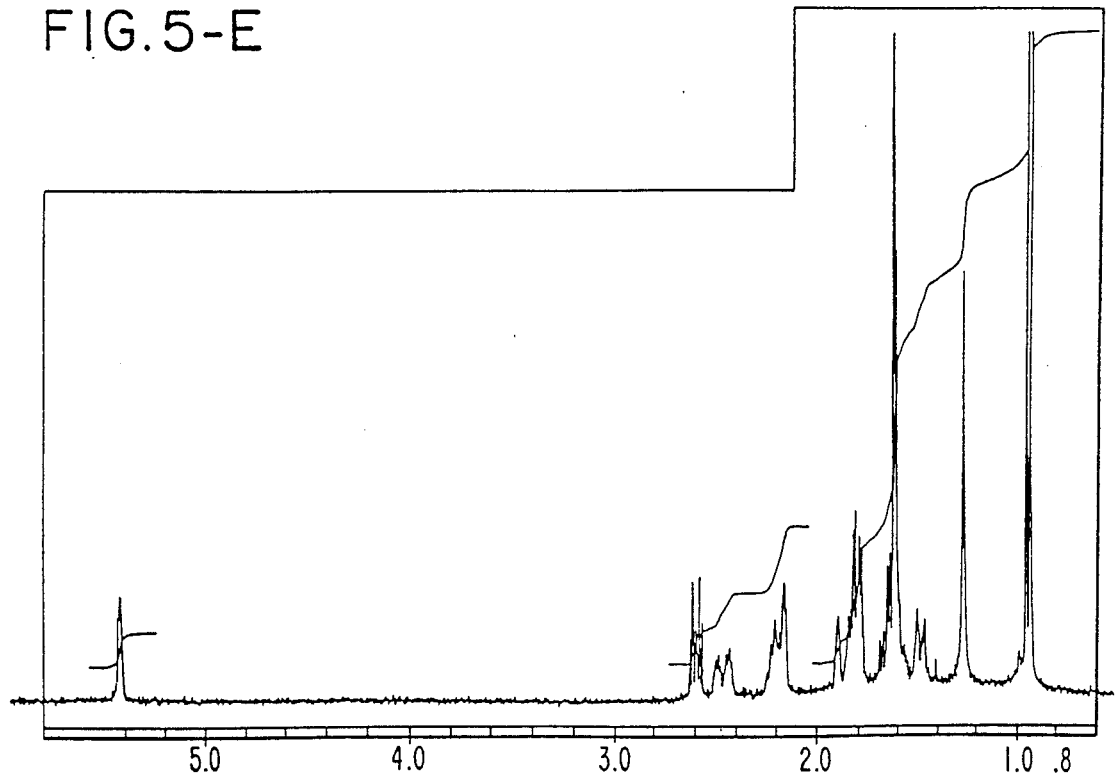

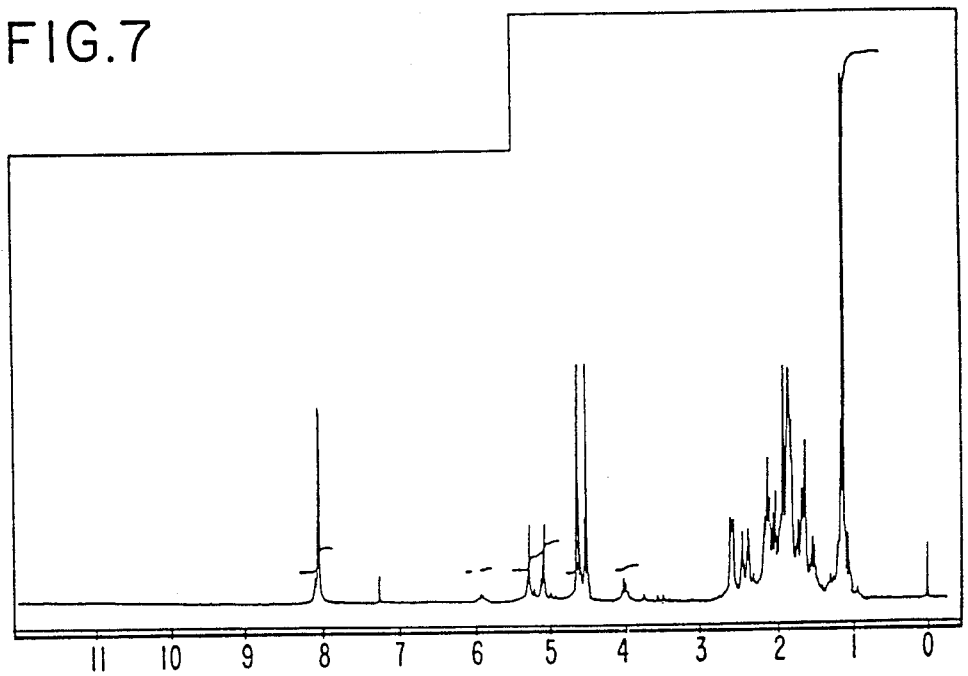

FIG.II

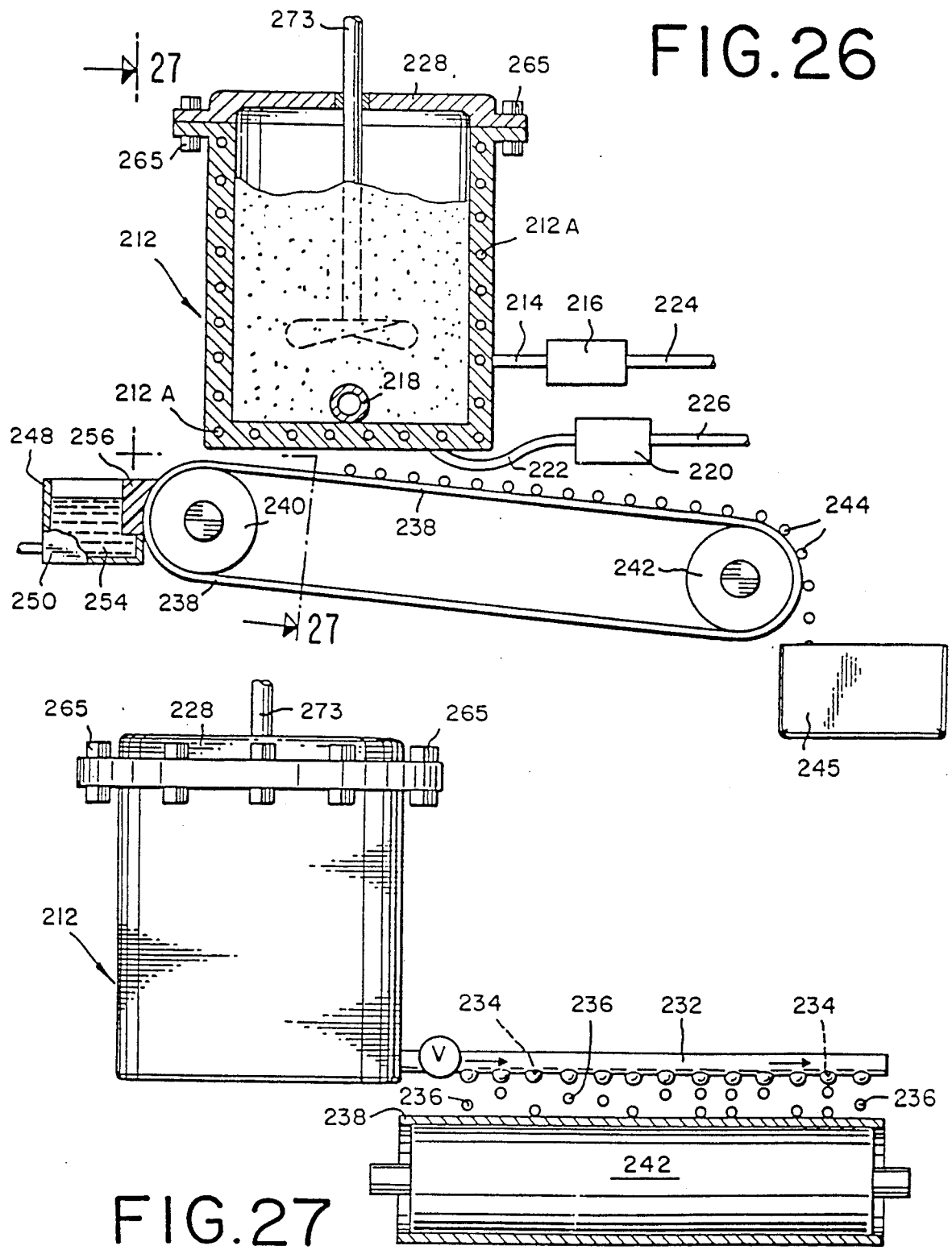

FIG.37-A
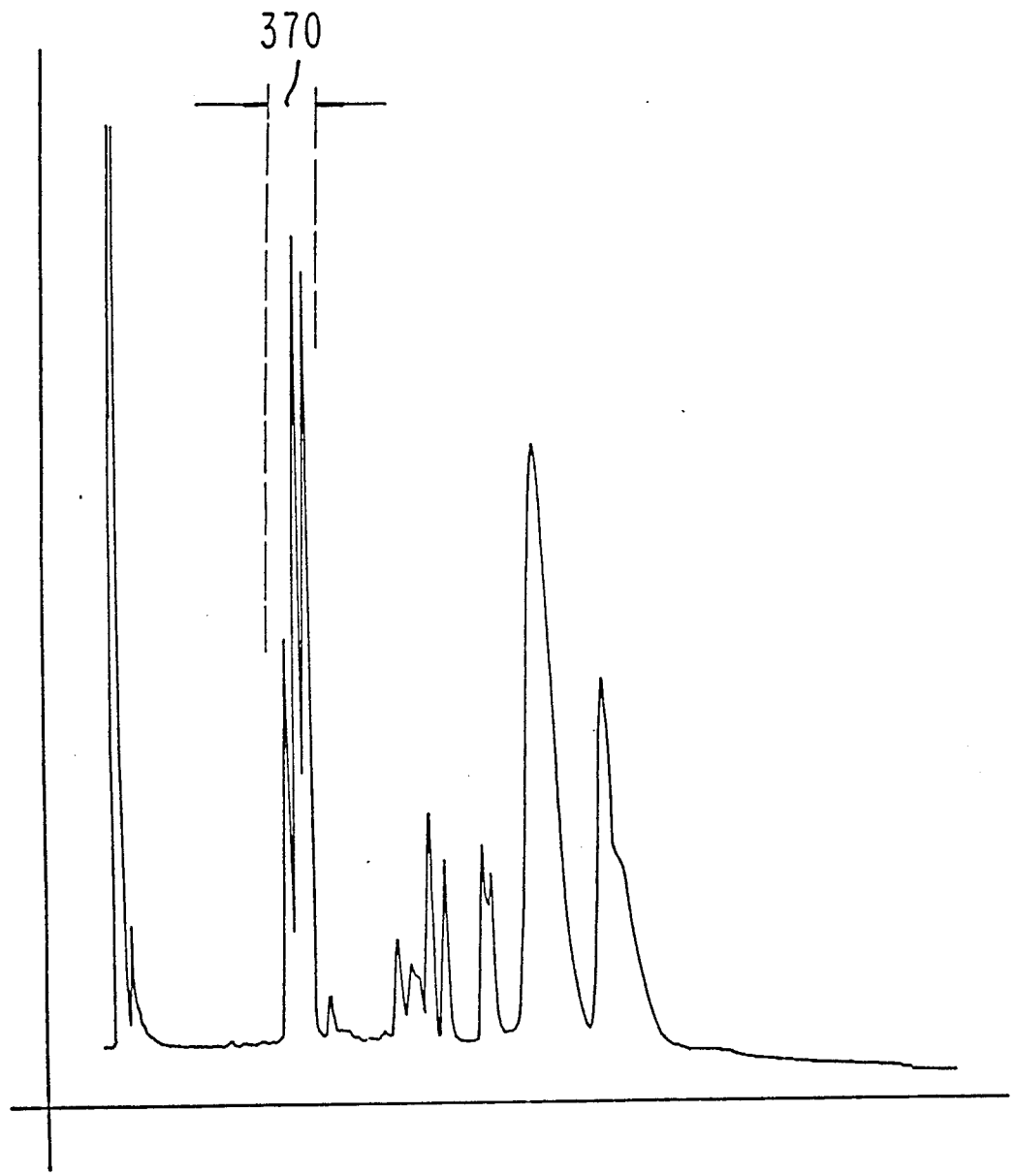

FIG.37-B
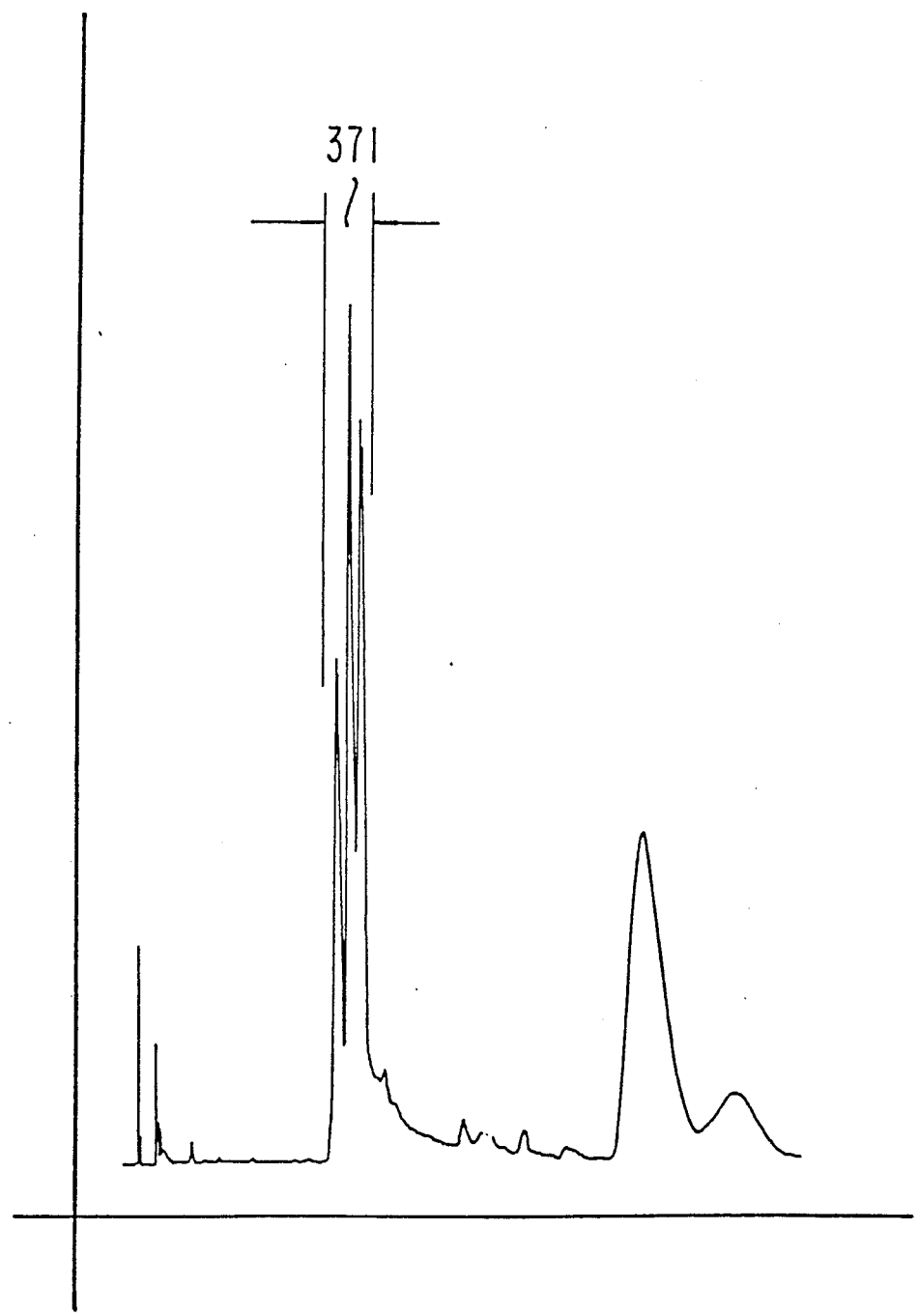

FIG.37-C
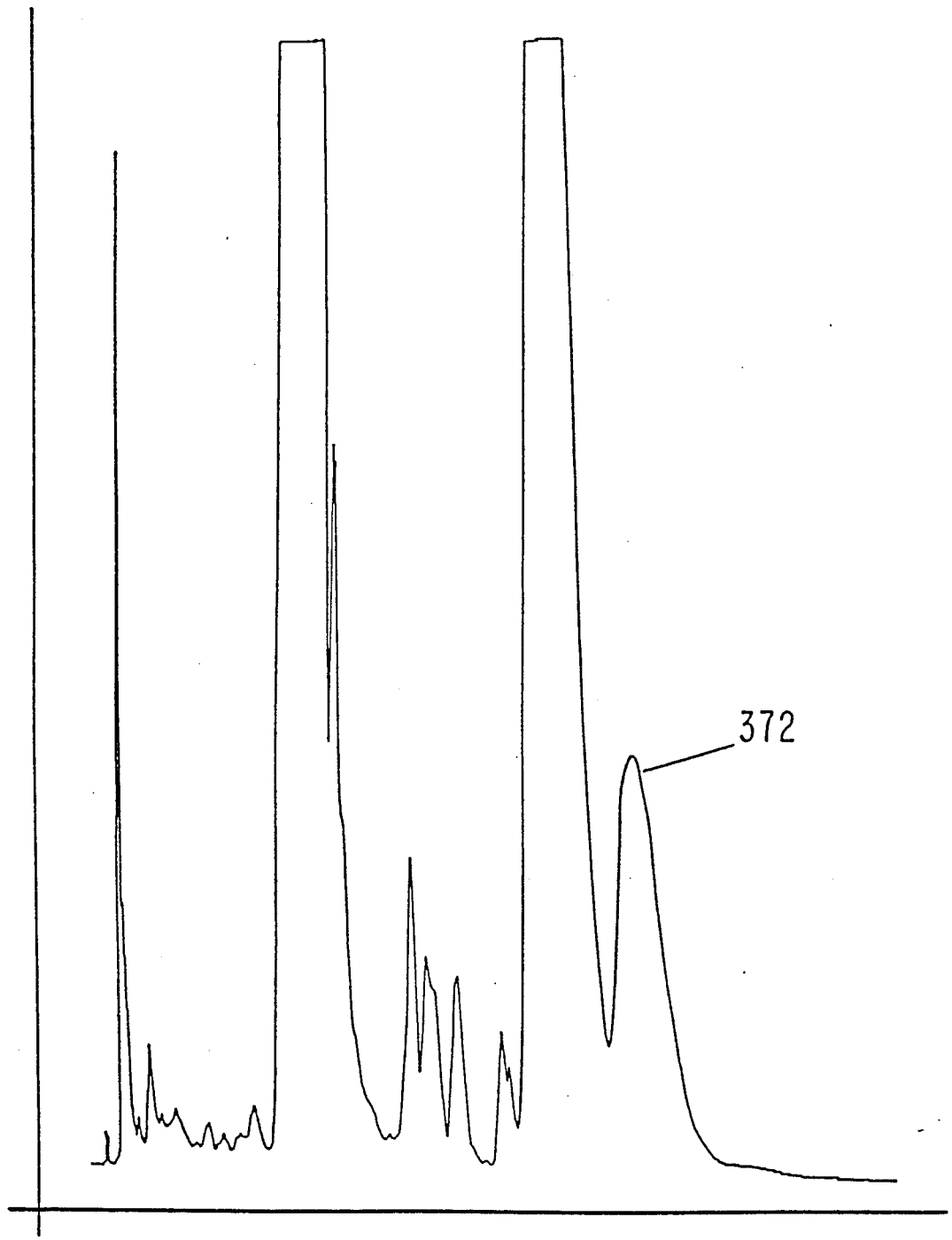

ADAMANTANE DERIVATIVES, COMPOSITIONS OF MATTER CONTAINING SAME, PROCESSES FOR PREPARING SAID ADAMANTANE DERIVATIVES AND SAID COMPOSITIONS, AND ORGANOLEPTIC AND DEODORANCY USES OF SAID ADAMANTANE DERIVATIVES AND SAID COMPOSITIONS

This application is a continuation-in-part of Application for U.S. Letters Pat. Ser. No. 261,275 filed on Oct. 21, 1988, now U.S. Pat. No. 4,956,481, issued on Sept. 11, 1990.

SUMMARY OF ADAMANTANE DERIVATIVES AND PROPERTIES

The following Table A summarizes the nature of the compounds of our invention and their aroma properties:

TABLE A

| Composition of Matter | Perfumery Properties |
|---|---|
| The compound having the structure: 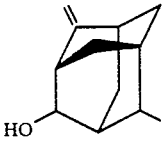 produced according to Example III, bulked fractions 6-9. | A sandalwood, woody, patchouli, rhubarb, ginger, minty and amyris aroma with amyris, camphoraceous, patchouli, woody, and piney topnotes. |
| The compound having the structure: 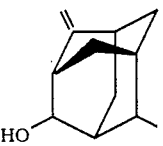 produced according to Example IIIA. | A camphoraceous, ginger cardamon and woody aroma profile. |
| The compound having the structure: 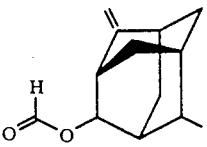 prepared according to Example IV, bulked fractions 8-18. | A cedarwood-like, sandalwood-like, camphoraceous, woody, minty and earthy aroma with cedarwood, sandalwood, patchouli, camphoraceous, herbaceous, incense and olibanum topnotes. |
| The compound having the structure: 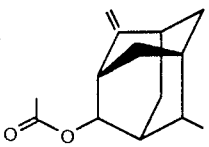 prepared according to Example V(B), bulked fractions 7-9. | A cedarwood-like, patchouli, vetiver, peppery, grapefruit peel-like and camphoraceous aroma with vetiver and grapefruit peel-like topnotes. |

TABLE A-continued

| Composition of Matter | Perfumery Properties |
|---|---|
| The compound having the structure: 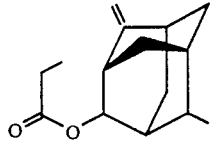 prepared according to Example VI, bulked fractions 10-16. | A woody, rose-like and peony-like aroma with floral, sweet pea, rose and peony topnotes. |
| The compound having the structure: 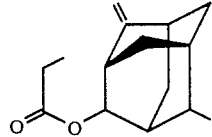 prepared according to Example VI, bulked fractions 5-19. | An ambery, woody and cedarwood-like aroma with fruity and woody topnotes. |
| The compound having the structure: 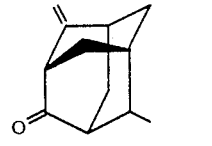 prepared according to Example VII. | A camphoraceous aroma with early morning forest path, green, piney, woody and camphoraceous topnotes. |
| The compound having the structure: 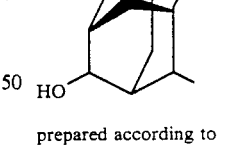 prepared according to Example X, bulked fractions 4 and 5. | A spicy, ginger root, rosemary and camphoraceous aroma with green, woody and ginger root topnotes. |
| The compound having the structure: 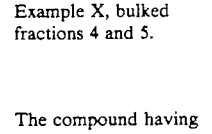 prepared according to Example XI, bulked fractions 5-9. | A woody, ambery, vetiver, cedarwood, piney and chrysanthemum-like aroma with woody, amber and olibanum topnotes. |

TABLE A-continued

| Composition of Matter | Perfumery Properties |
|---|---|
| The compound having the structure: 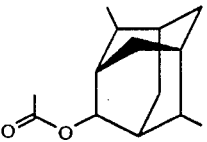 prepared according to Example XIII, bulked fractions 2-18. | A woody, amber, vetiver, cedarwood, piney and chrysanthemum-like aroma with woody, amber and olibanum topnotes. |
| The mixture of compounds having the structures: 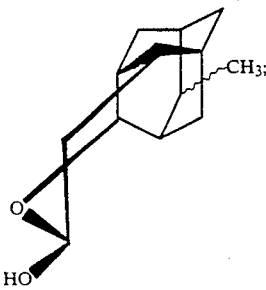 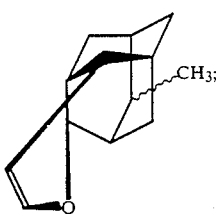 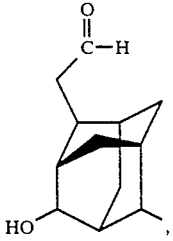 and 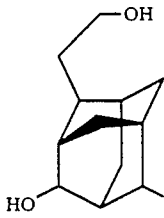 prepared according to Example XIV, fraction 6. | A green, woody and fir balsam-like aroma profile. |
| The mixture of compounds having the structures: 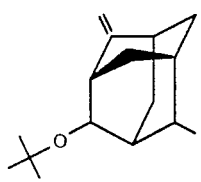 | A camphoraceous aroma with sweet camphoraceous topnotes. |

TABLE A-continued

| Composition of Matter | Perfumery Properties |
|---|---|
|     and  prepared according to Example XV. | |
| The compound having the structure:  bulked fractions 4-6 produced according to Example XII. | A fresh, camphoraceous, sage-like and woody aroma profile with camphoraceous and woody topnotes |

BACKGROUND OF THE INVENTION

This invention relates to adamantane derivatives which have the structure:

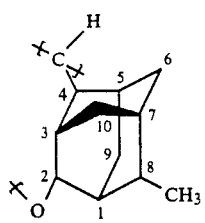

substituted at least at the "2", "4" and "8" positions, thusly:

(a) at the "2" position with an oxygen atom;
(b) at the "4" position with a carbon atom; and
(c) at the "8" position with a methyl group and uses thereof in augmenting or enhancing the aroma or taste of consumable materials.

There has been considerable work performed relating to substances which can be used to impart (modify, augment or enhance) fragrances to (or in) various consumable materials. These substances are used to diminish the use of natural materials some of which may be in short supply and to provide more uniform properties in the finished product.

Long-lasting, substantive and intense sandelwood, woody, patchouli, rhubarb, ginger, minty, amyris, camphoraceous, cardamon, earthy, cedarwood-like, vetiver, peppery, grapefruit peel-like, rose-like, ambery, spicy, ginger root, rosemary, piney, chrysanthemon-like, green and fir balsam-like aromas with sweet, amyris, camphoraceous, patchouli, woody, piney, cedarwood, sandalwood, herbaceous, incense, olibanum, vetiver, grapefruit peel-like, floral, sweet pea, rose, peony, fruity, early morning forest path, green, ginger root and amber topnotes are desirable in several types of perfume compositions, perfumed articles, colognes, deodorizing compositions and odor maskant materials.

The use of tricyclic alcohol derivatives in perfumery for augmenting or enhancing the aromas of perfume compositions, perfumed articles and colognes is well known in the art. Thus, Inamoto, et al in U.S. Pat. No. 4,036,893 discloses the use in perfumery of the compound having the structure:

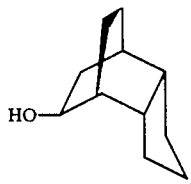

Inamoto, et al in U.S. Pat. No. 4,169,958 also discloses the use of the tricyclic alcohol having the structure:

in perfumery. Light, et al in U.S. Pat. No. 3,996,169 discloses the use of compound having the structure:

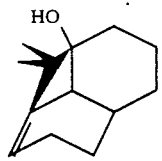

in perfumery. Inamoto, et al in U.S. Pat. No. 4,169,958 also discloses the use of the tricyclic alcohol having the structure:

in perfumery. Light, et al in U.S. Pat. No. 3,996,169 discloses the use of the compound having the structure:

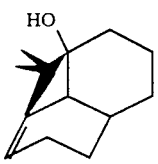

in perfumery. Inamoto, et al in U.S. Pat. No. 4,036,892 discloses the use of the compound having the structure:

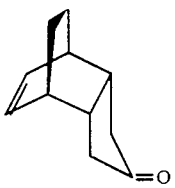

and in U.S. Pat. No. 4,036,892 discloses the use in perfumery of the compound having the structure:

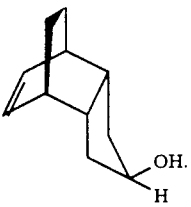

The use in perfumery of the compound having the structure:

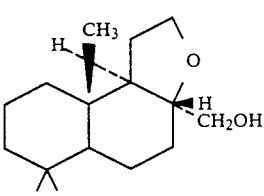

is disclosed in Chemical Abstracts, Volume 109, 9, 1988, No. 6759v (abstract of Koltsa, et al Zh.Obshch.Khim., 1987, 57 (11) 2620–9.

Light, et al at U.S. Pat. No. 4,439,354 discloses the genus of compounds defined according to the structure:

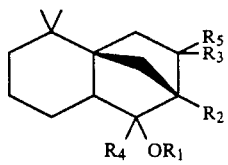

for use in perfumery wherein $R_1$ represents hydrogen, methyl or acetyl and $R_2$, $R_3$, $R_4$ and $R_5$ each represent hydrogen, methyl or ethyl.

Light, et al at U.S. Pat. No. 3,996,169 discloses the genus of compounds defined according to the structure:

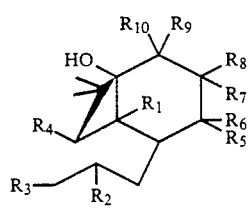

where one or more of the R groups represents hydrogen or methyl.

Adamantane derivatives and adamantane itself are known for use in augmenting or enhancing the aroma of perfume compositions, perfumed articles and colognes. Thus, the perfume use of compounds having the structures:

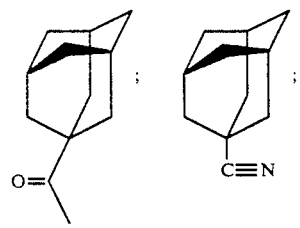

and

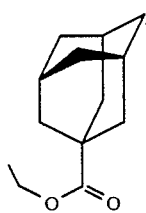

is disclosed in Chemical Abstracts, Volume 71, No. 94695w (abstract of Netherlands Published Application 6715903, May 28, 1969). Japan Kokai 75/25742 Published on Mar. 18, 1975 and abstracted at Chem.Abstracts, Volume 84, No. 35214j and Japan Kokai Tokkyo Koho 78:145920 Published on Dec. 19, 1978 and abstracted at Chem.Abstracts, Volume 90, No. 142085p discloses the perfume use of adamantane itself having the structure:

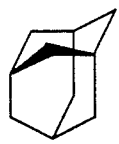

Synthesis of various oxygen-substituted adamantane derivatives is well known in the prior art.

Mlinaric'-Magerski and Magerski, J. Am. Chem. Soc., 1983, 105, pages 7389–7395 discloses the compound having the structure:

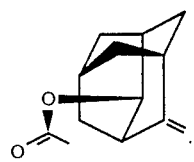

at page 7390 and discloses the reaction squence:

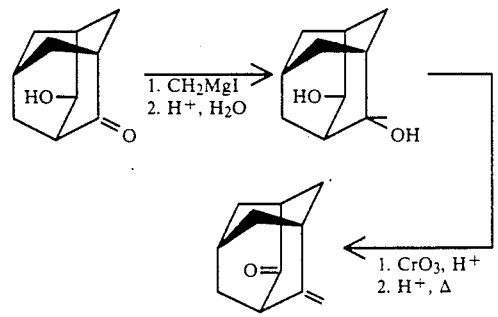

at page 7389.

Hallden-Aberton, J. Org. Chem., Volume 46, No. 3, 1981, pages 538–546 discloses the reaction sequence:

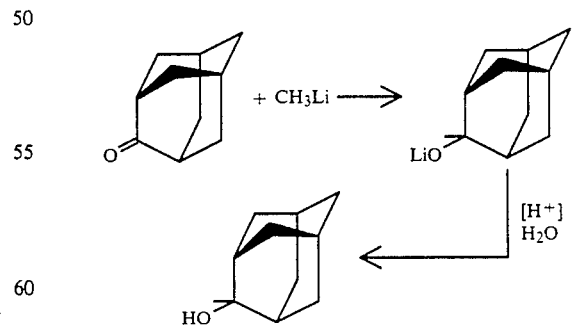

at pages 539 and 544.

Drivas & Mison, Tetrahedron Letters, Volume 22, 1981, at pages 641–644 discloses at page 643 the reaction sequence:

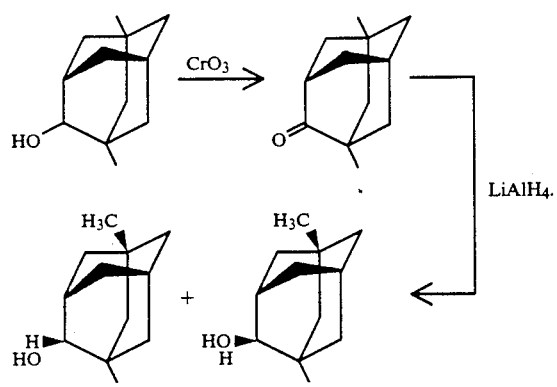

Kovalev, et al, Chem. Abstracts, Volume 109, 1988, No. 22553d (abstract of Zh.Org.Khim., 1987, 23(9), 1882-6 discloses the compounds having the structures:

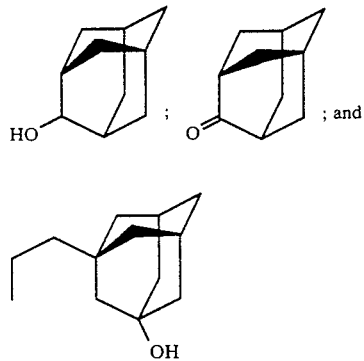

and discloses the reaction sequence:

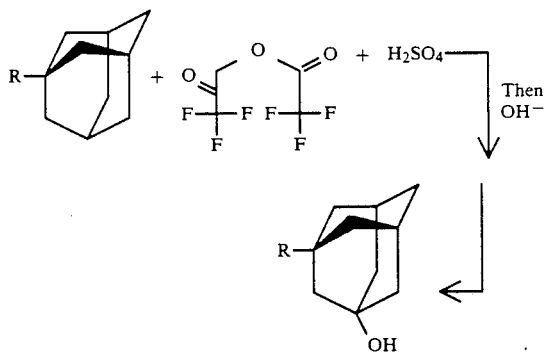

However, the adamantane derivatives of our invention have unexpected, unobvious and advantageous properties with respect to the compounds of the prior art. Nothing in the prior art explicitly or implicitly sets forth the adamantane derivatives of our invention or their uses.

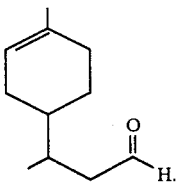

Figure 1:
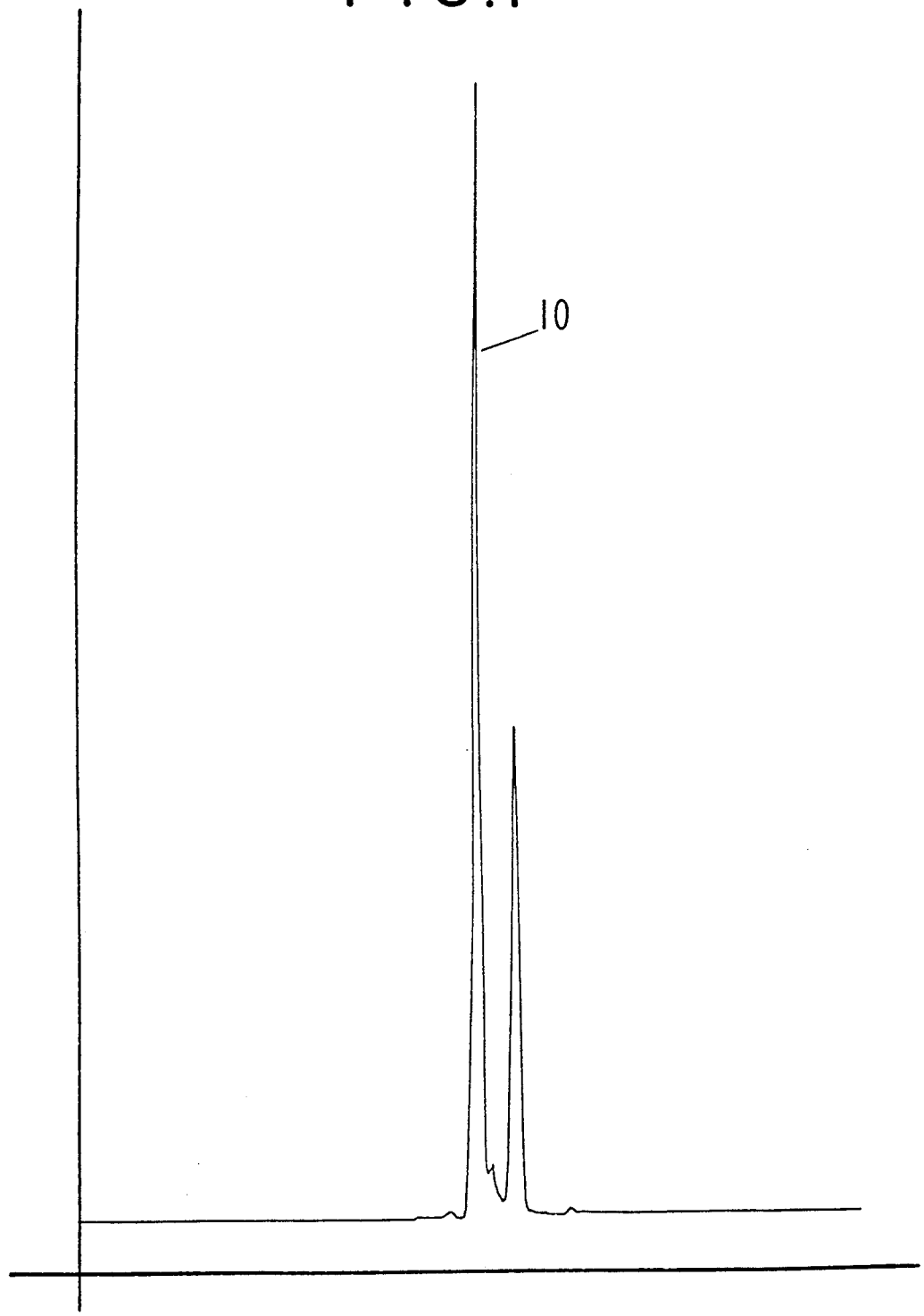

FIG. 1 is the GLC profile for the reaction product of Example I containing the compound having the structure:

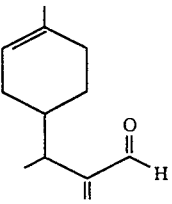

(Conditions: K-20M column programmed at 100°-220° C. at 8° C. per minute).

Figure 2:
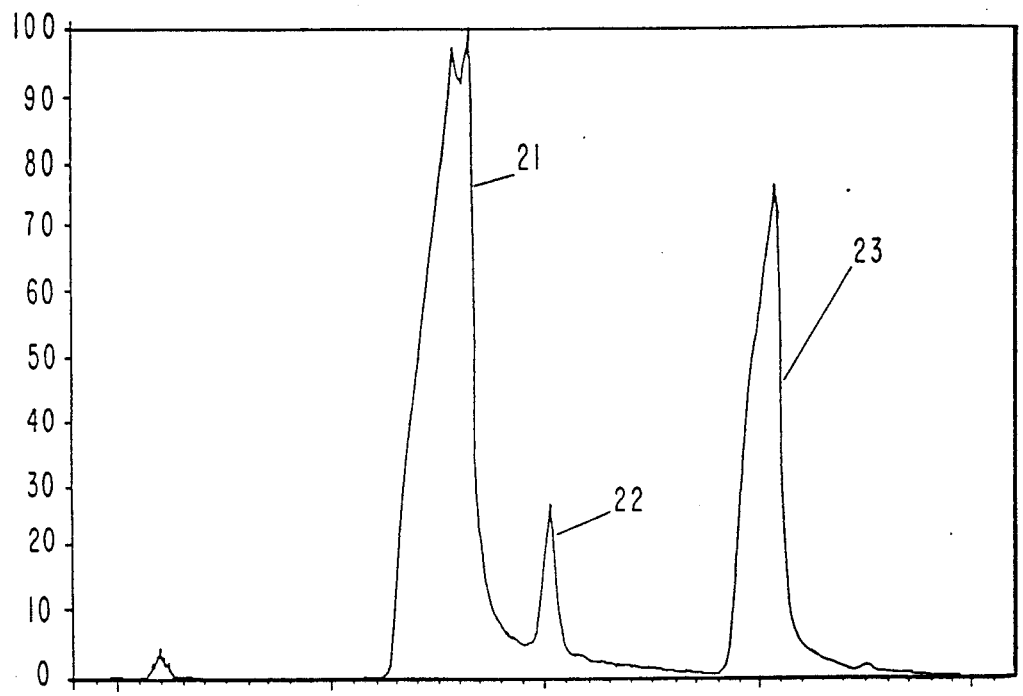

FIG. 2 is another GC scan for the reaction product of Example I containing the compound having the structure:

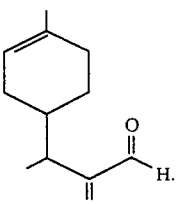

Figure 3:
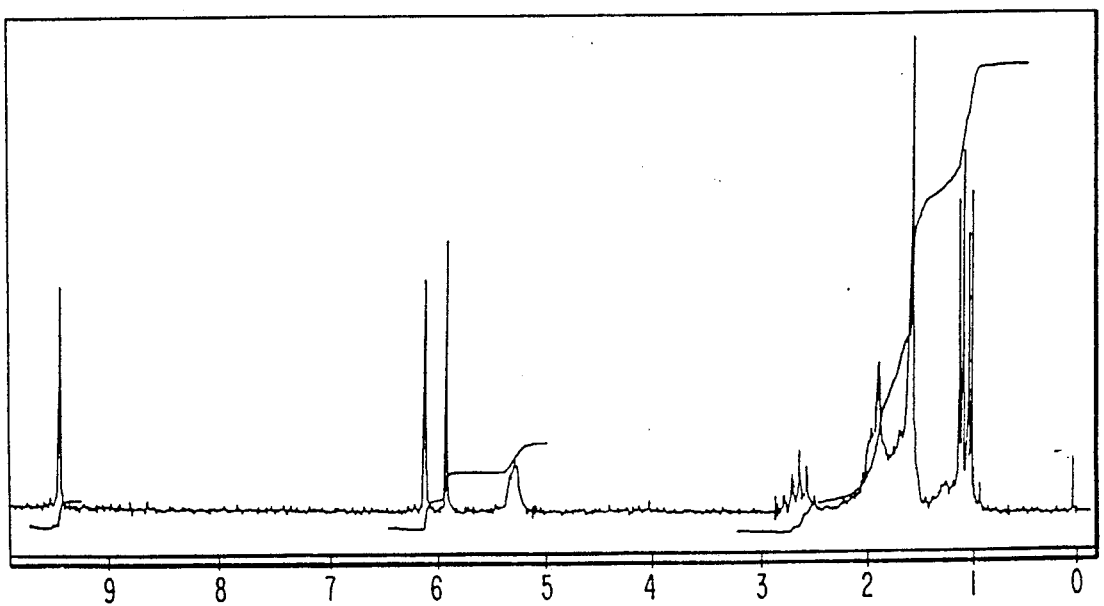

FIG. 3 is the NMR spectrum for the compound having the structure:

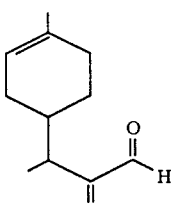

prepared according to Example I.

Figure 4:
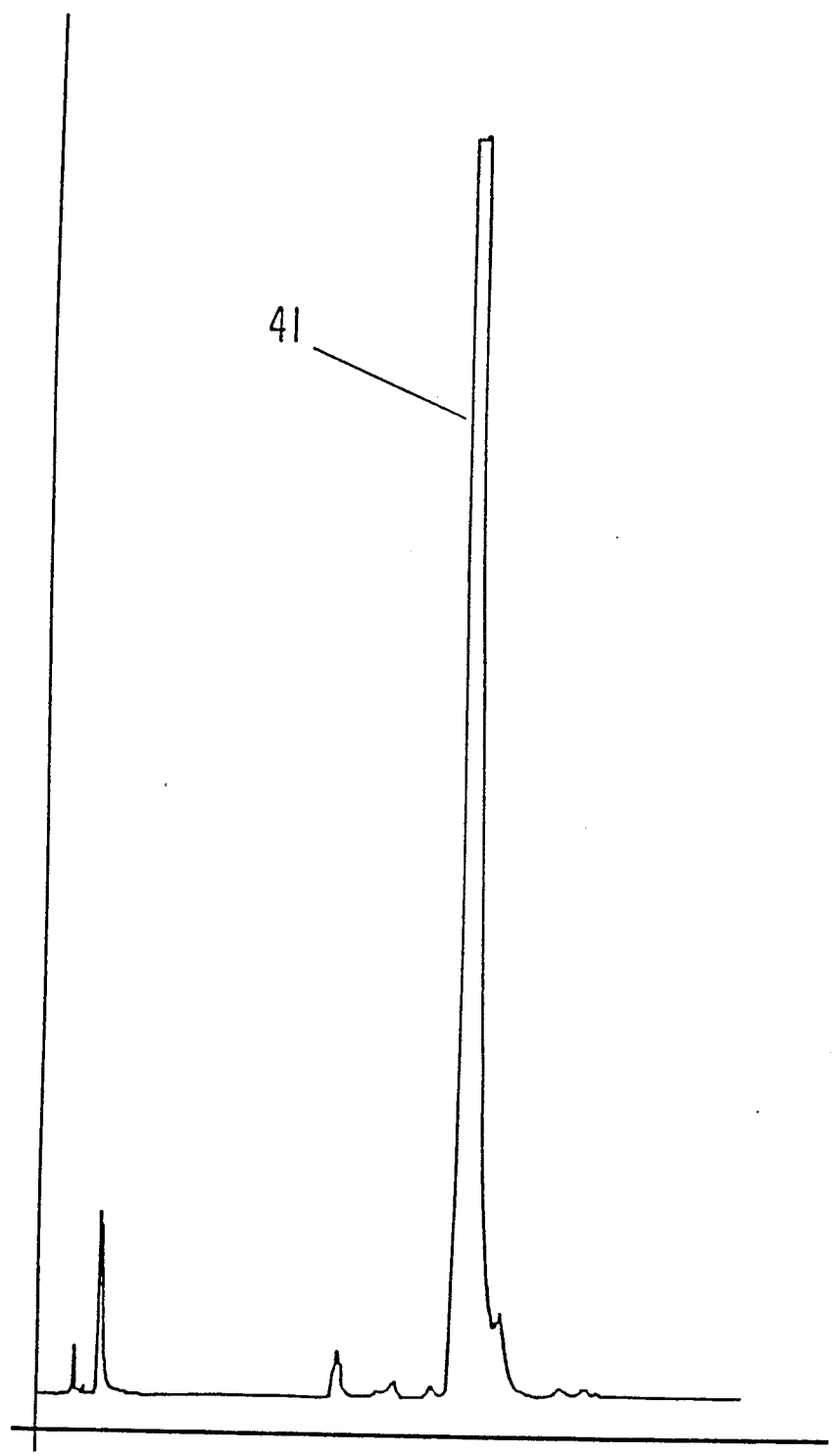

FIG. 4 is the GLC profile for fraction 4 of the distillation product of the reaction product of Example II containing the compound having the structure:

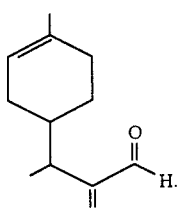

Figure 5:
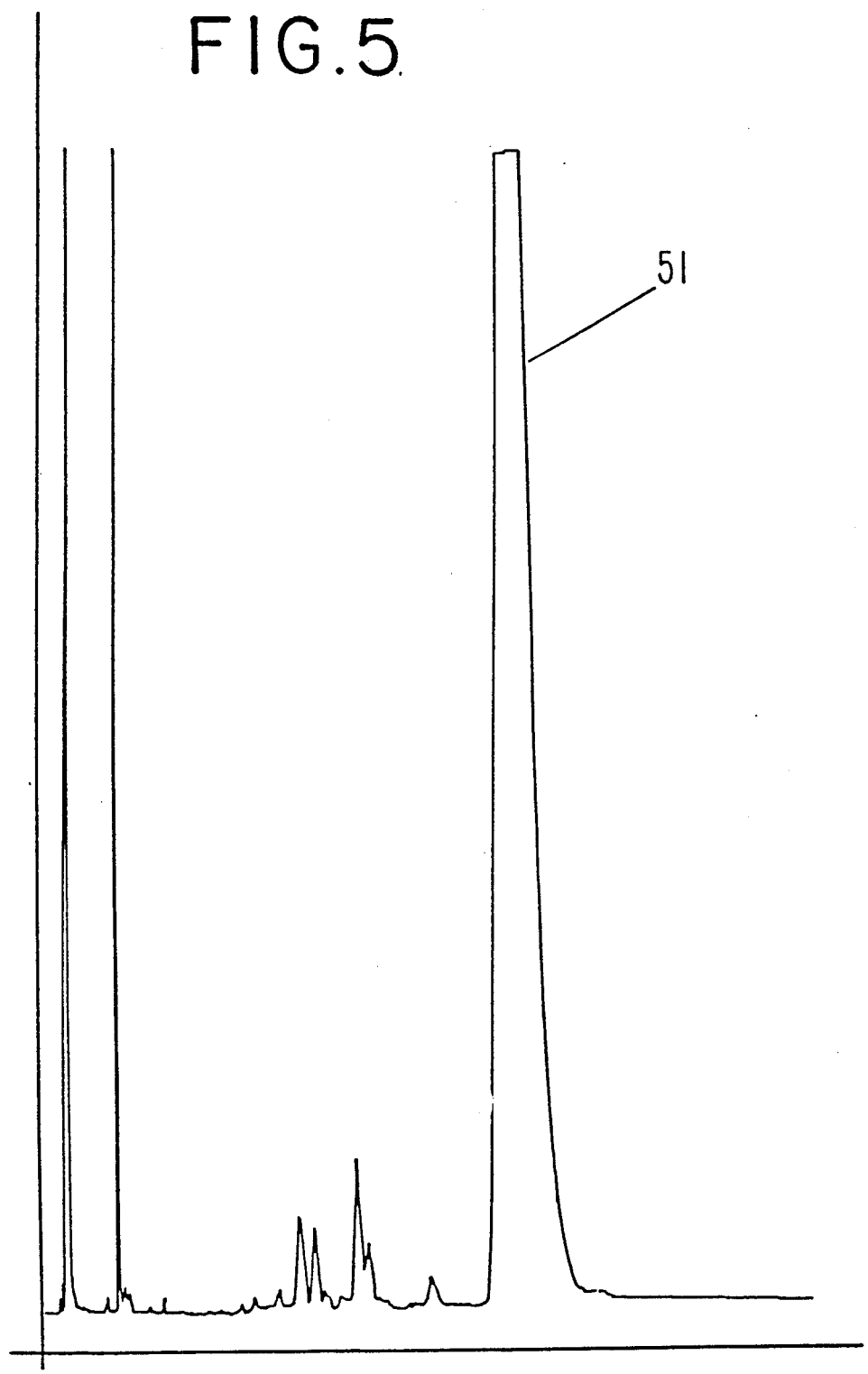

FIG. 5 is the GLC profile for the reaction product of Example III containing the compound having the structure:

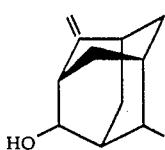

(Conditions: Carbowax column programmed at 130°-220° C.).

FIG. 5A is the GLC profile for the crude reaction product of Example III(A) containing the compound having the structure:

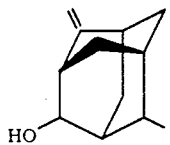

and, (in addition, the compounds having the structures:

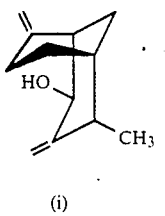 and 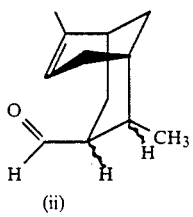

(i) (ii)

wherein each of the representations of the foregoing structures shows mixtures and wherein in the mixtures in each of the compounds one of the dashed lines is a carbon-carbon double bond and the other of the dashed lines is a carbon-carbon single bond.

FIG. 5B is the NMR spectrum for the compound having the structure:

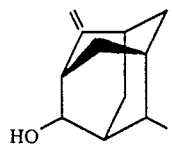

FIGS. 5C, 5D and 5E are each NMR spectra for epimers of the compound having the structure:

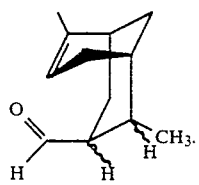

Figure 6:
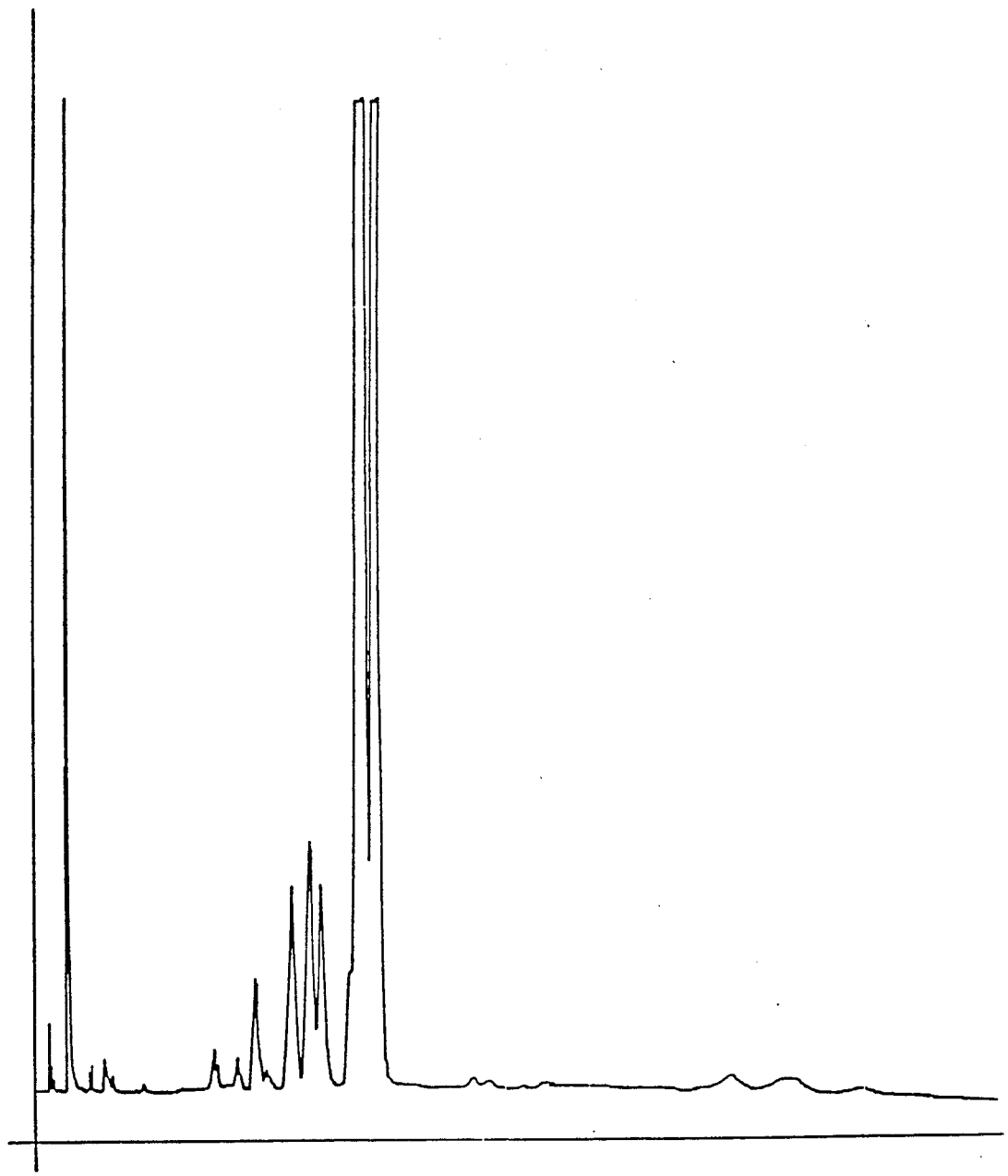

FIG. 6 is the GLC profile for the crude reaction product of Example IV containing the compound having the structure:

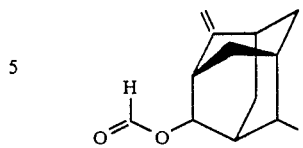

(Conditions: Carbowax column programmed at 130°-220° C.).

FIG. 7 is the NMR spectrum for the compound having the structure:

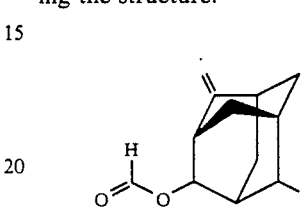

prepared according to Example IV.

FIG. 8 is the GLC profile for the crude reaction product of Example V(A) containing the compound having the structure:

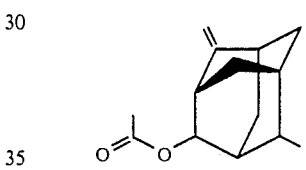

(Conditions: Carbowax column programmed at 130°-220° C.).

Figure 9:
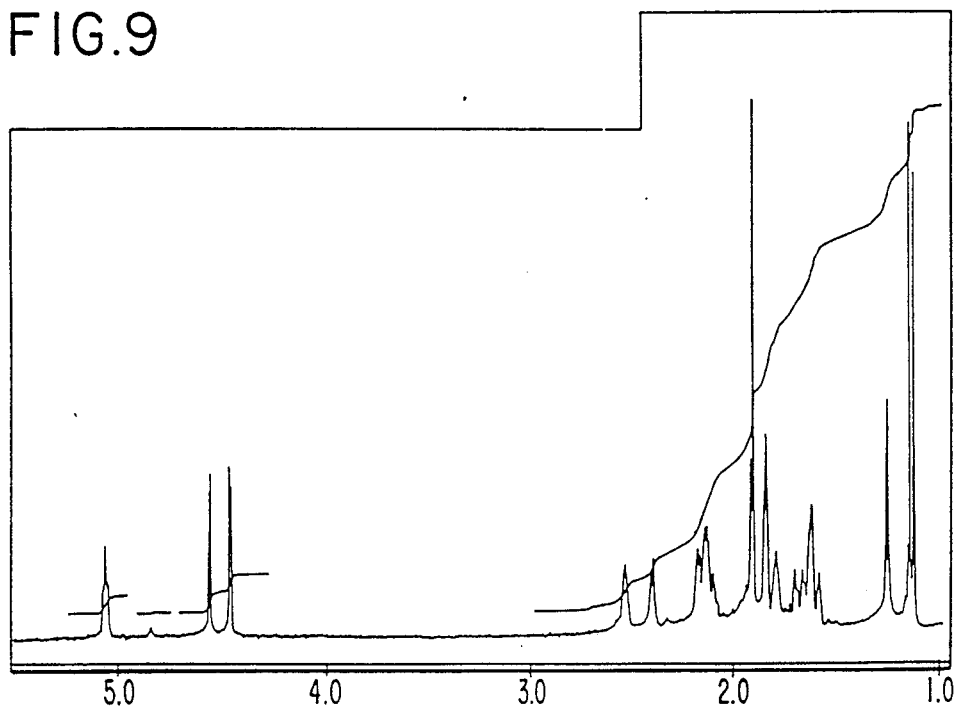

FIG. 9 is the NMR spectrum for the isomer having the structure:

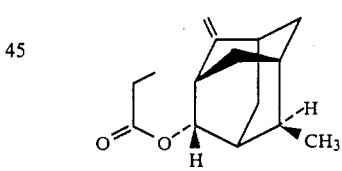

prepared according to Example V(A).

Figure 10:
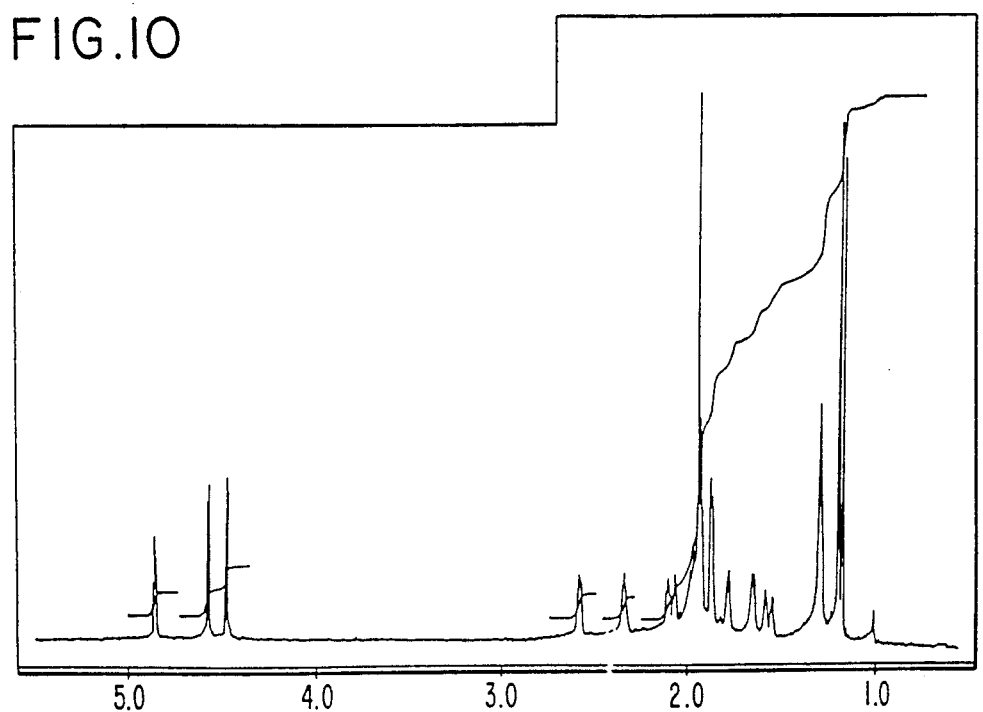

FIG. 10 is the NMR spectrum for the isomer having the structure:

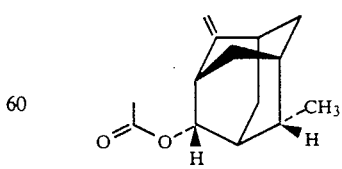

prepared according to Example V(A).

Figure 11:
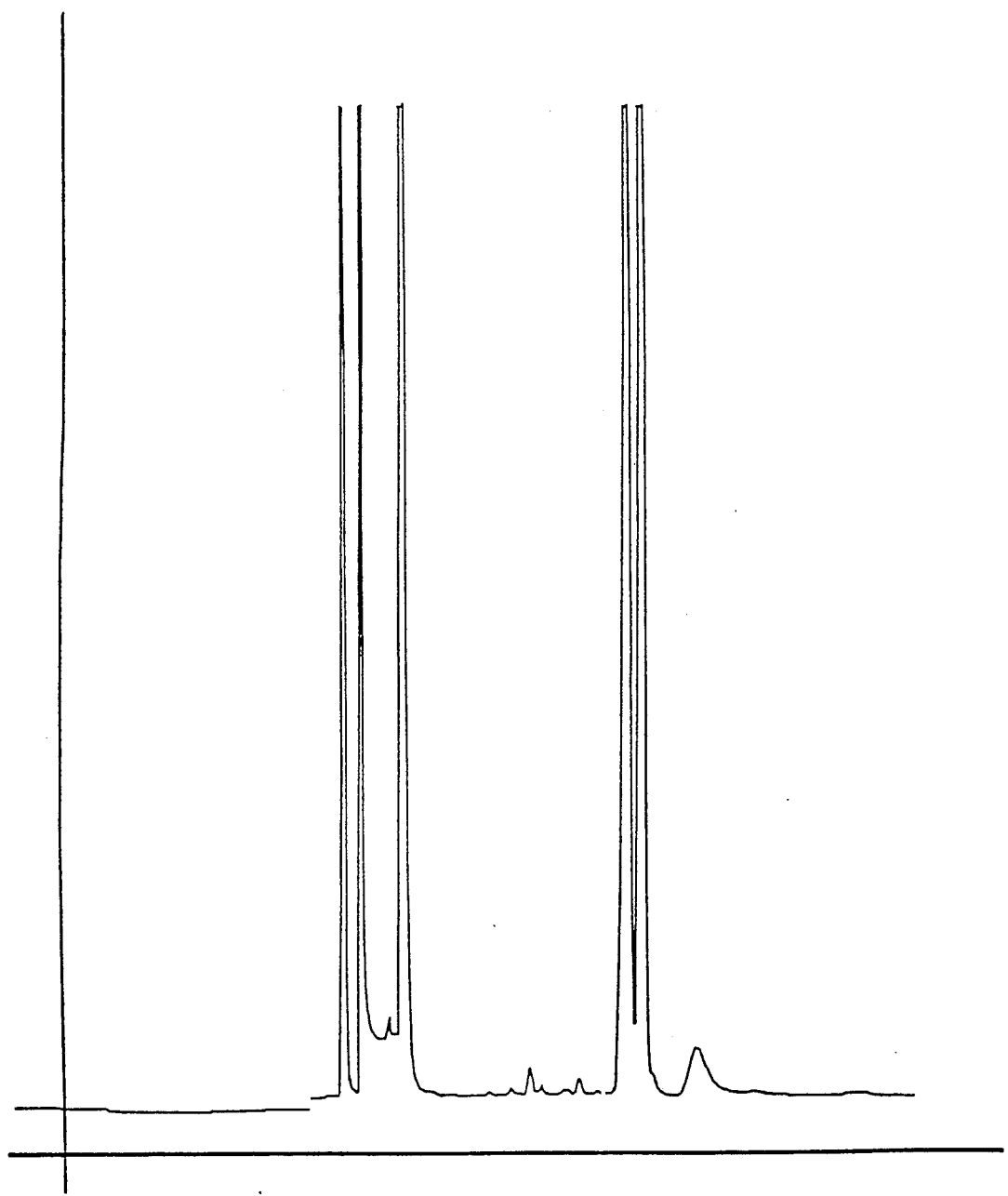

FIG. 11 is the GLC profile for the crude reaction product of Example V(B) containing the compound having the structure:

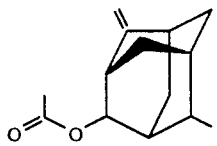

(Conditions: Carbowax column programmed at 130°-220° C.).

Figure 12:
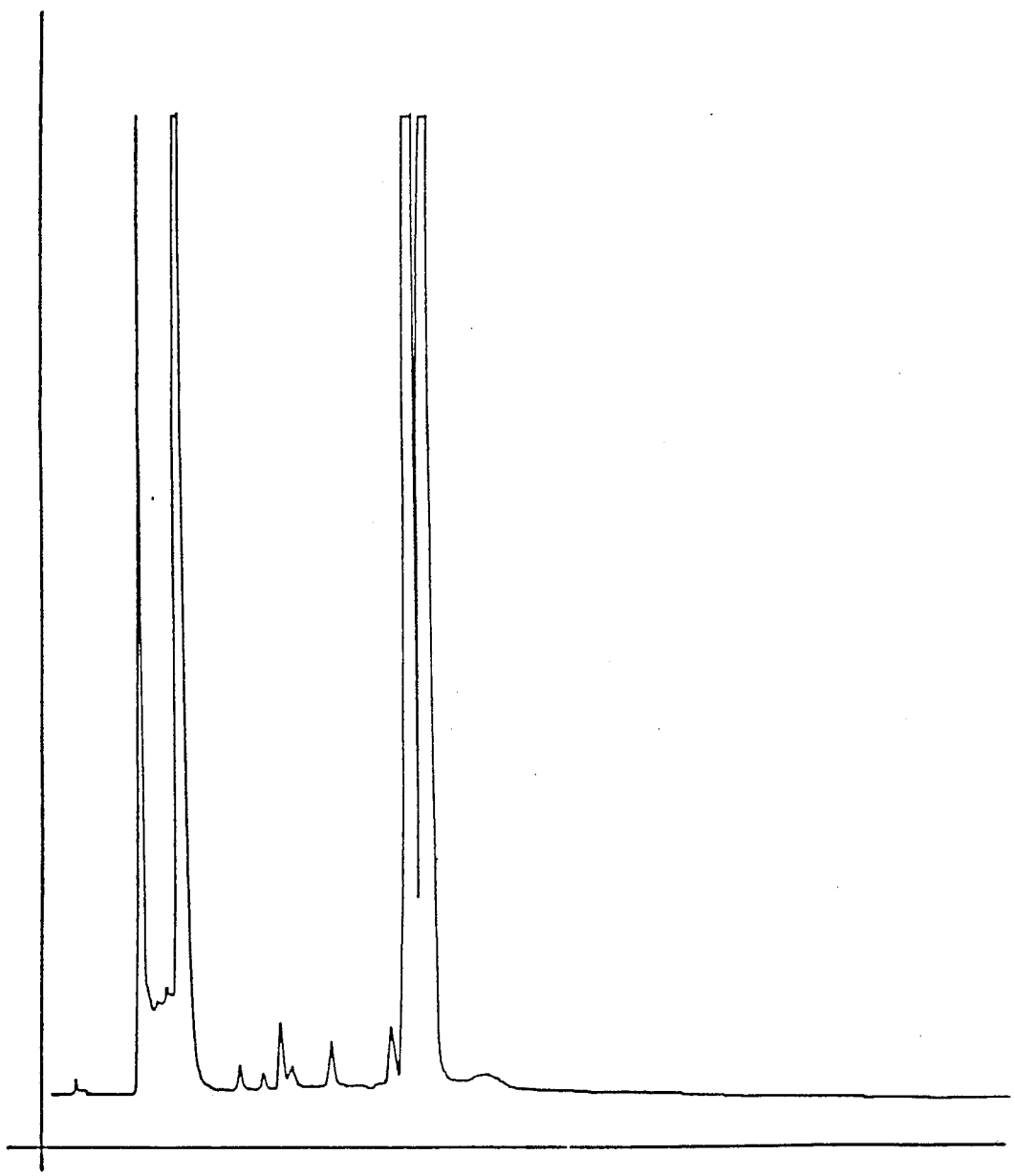

FIG. 12 is the GLC profile for the crude reaction product of Example VI containing the compound having the structure:

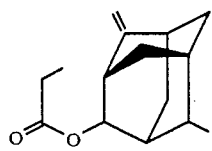

(Conditions: Carbowax column programmed at 130°-220° C.).

Figure 13:
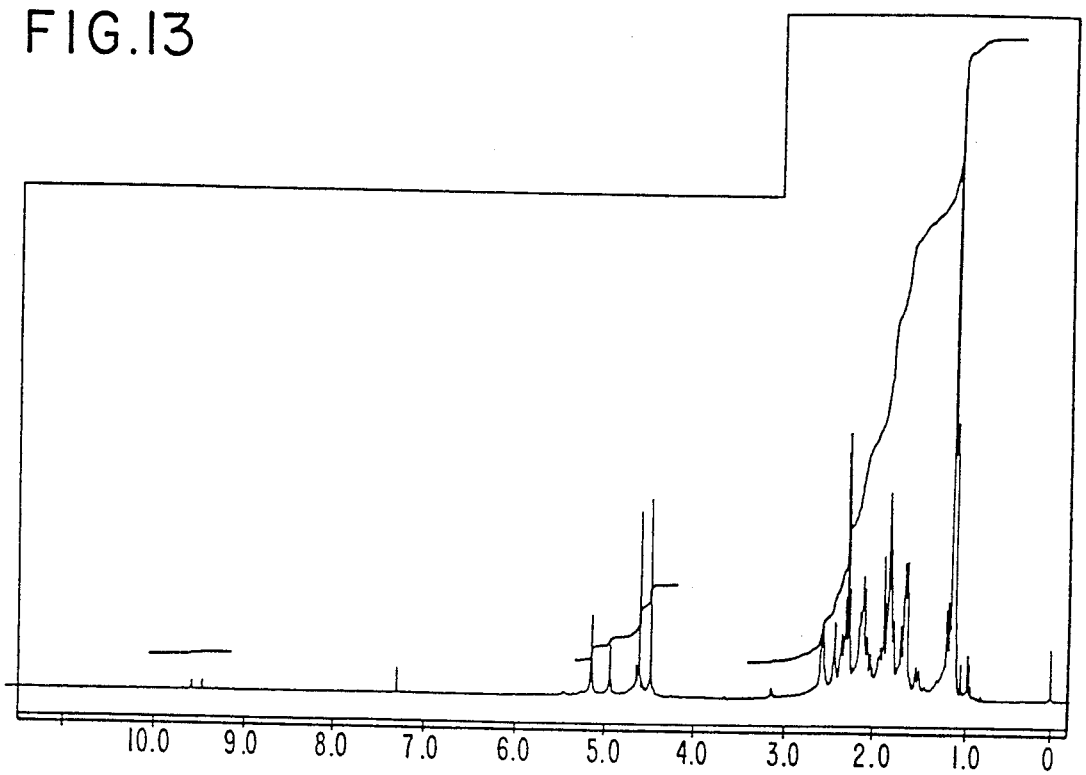

FIG. 13 is the NMR spectrum for the compound having the structure:

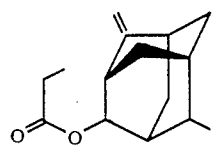

prepared according to Example VI.

Figure 14:
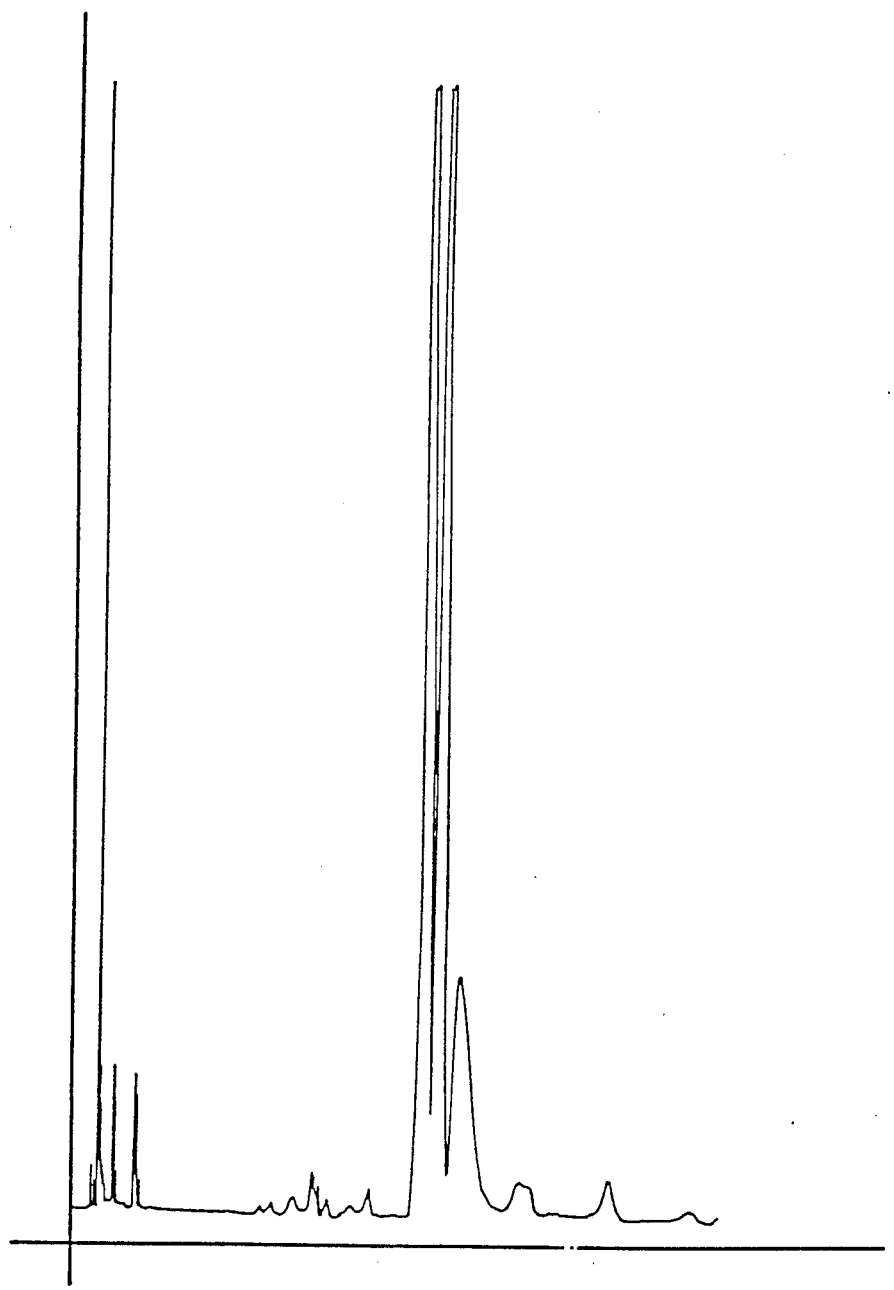

FIG. 14 is the GLC profile for the crude reaction product of Example VII containing the compound having the structure:

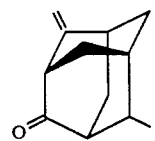

(Conditions: Carbowax column programmed at 130°-220° C.).

Figure 15:
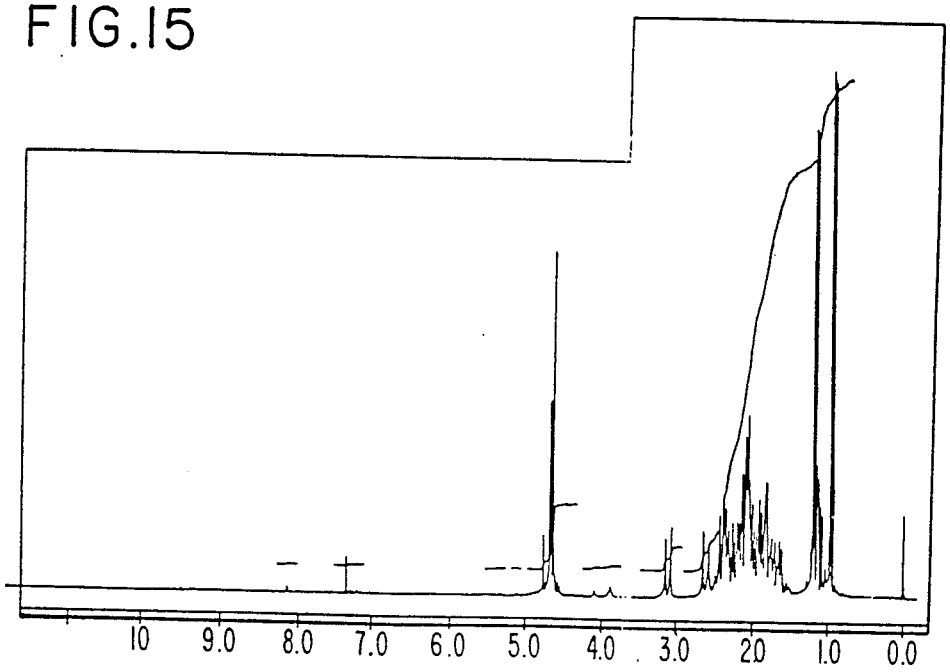

FIG. 15 is the NMR spectrum for the compound having the structure:

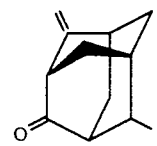

prepared according to Example VII.

Figure 16:
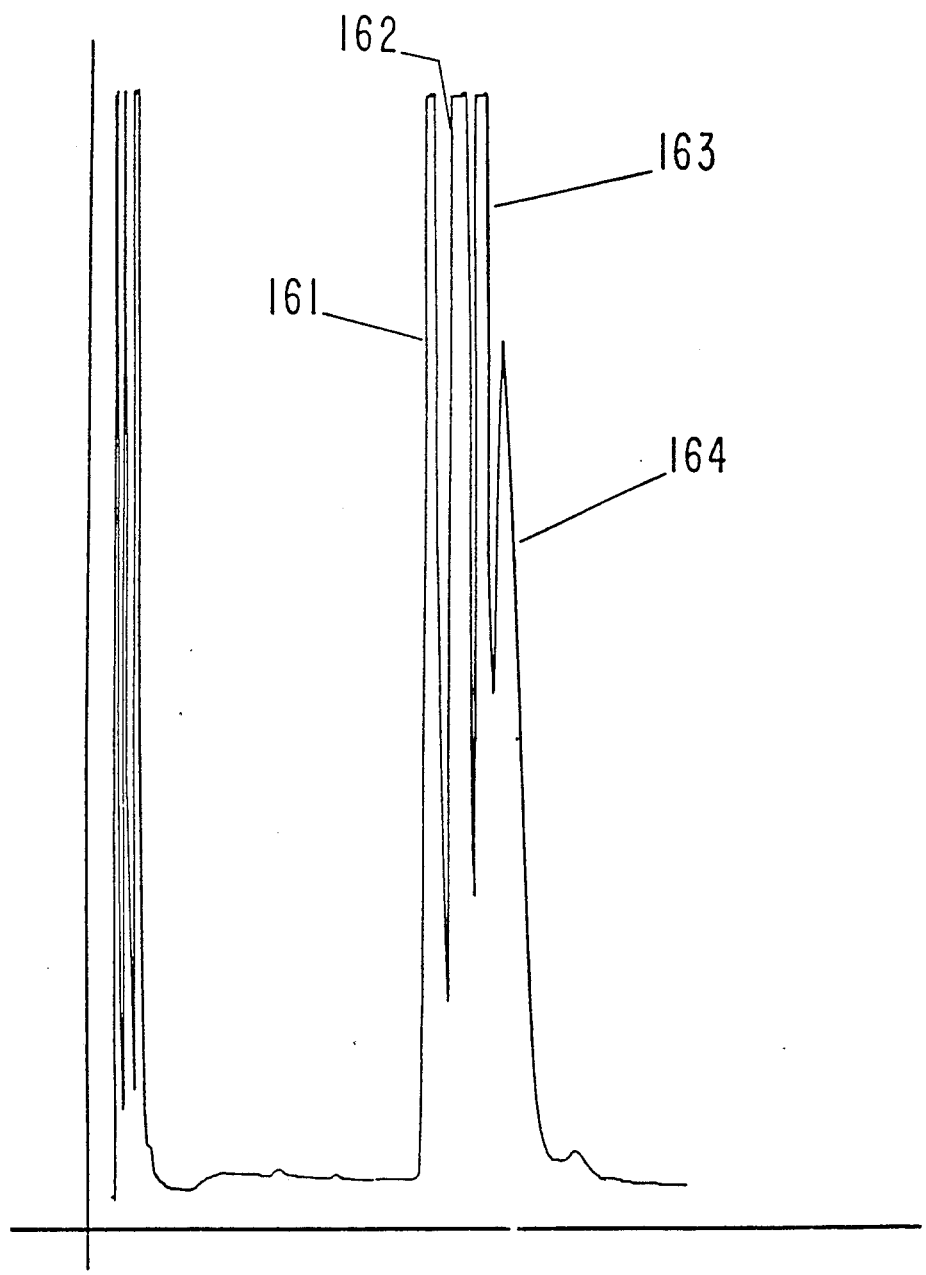

FIG. 16 is the GLC profile for the crude reaction product of Example VIII containing the compound having the structure:

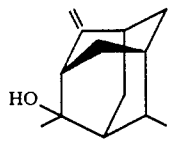

Figure 17:
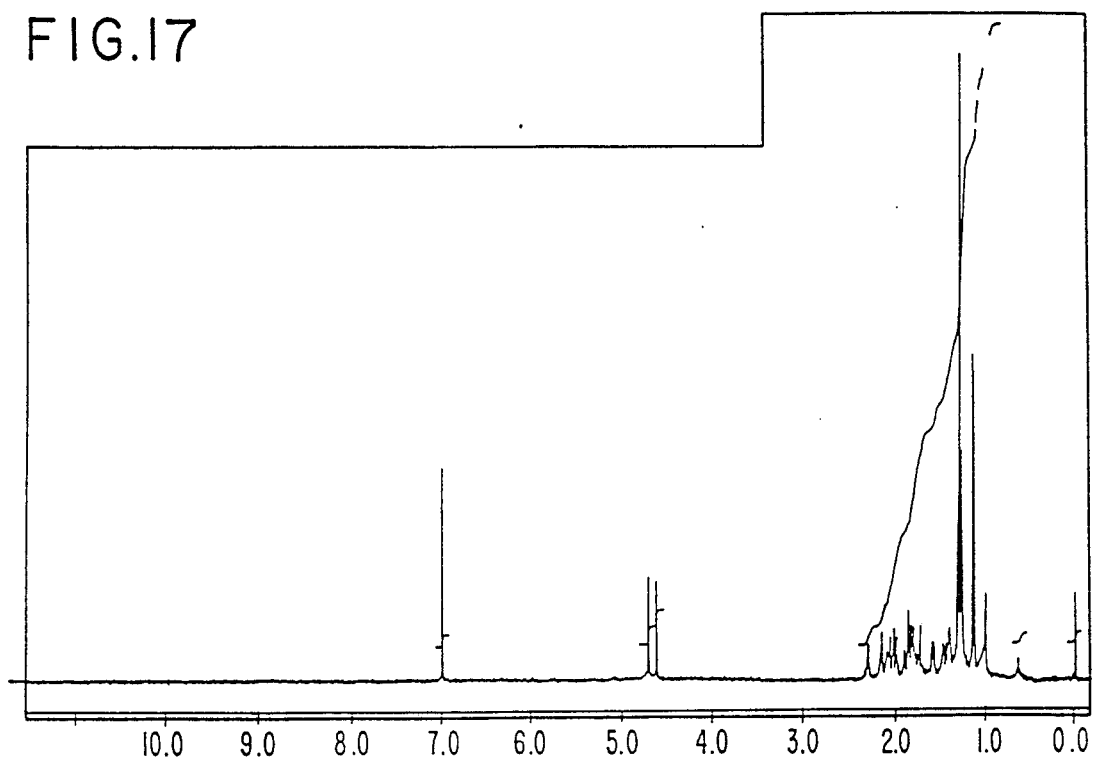

FIG. 17 is the NMR spectrum for the peak indicated by reference numeral 161 in FIG. 16, the compound having the structure:

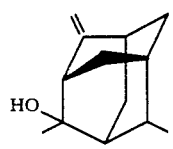

Figure 18:
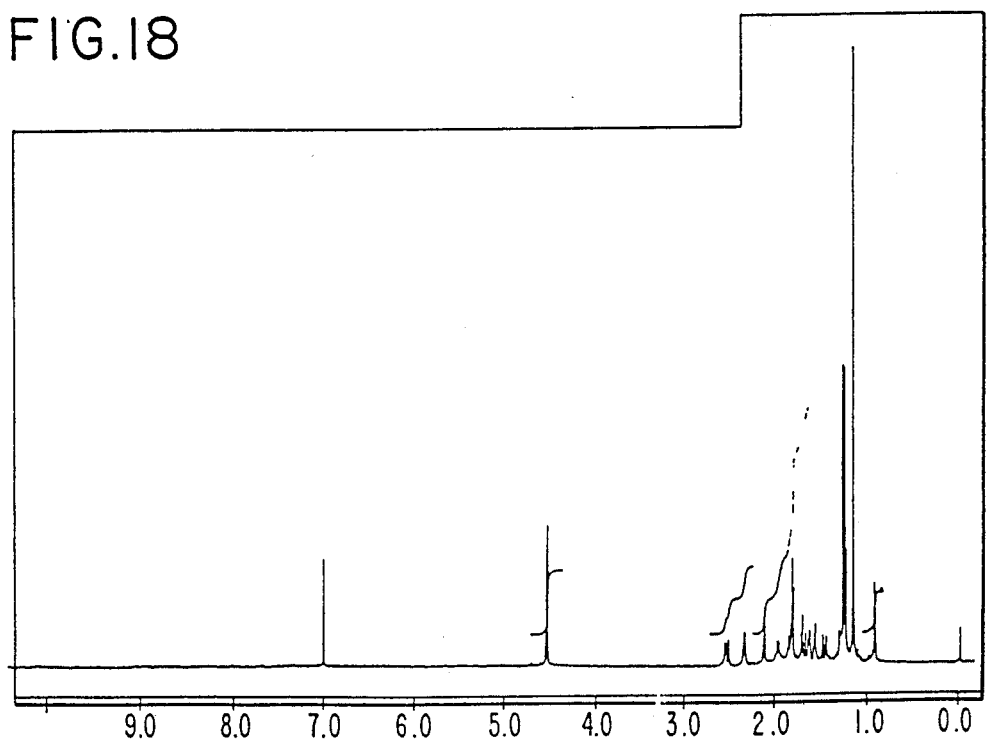

FIG. 18 is the NMR spectrum for the peak indicated by reference numeral 162 in FIG. 16; the compound having the structure:

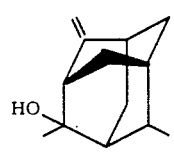

Figure 19:
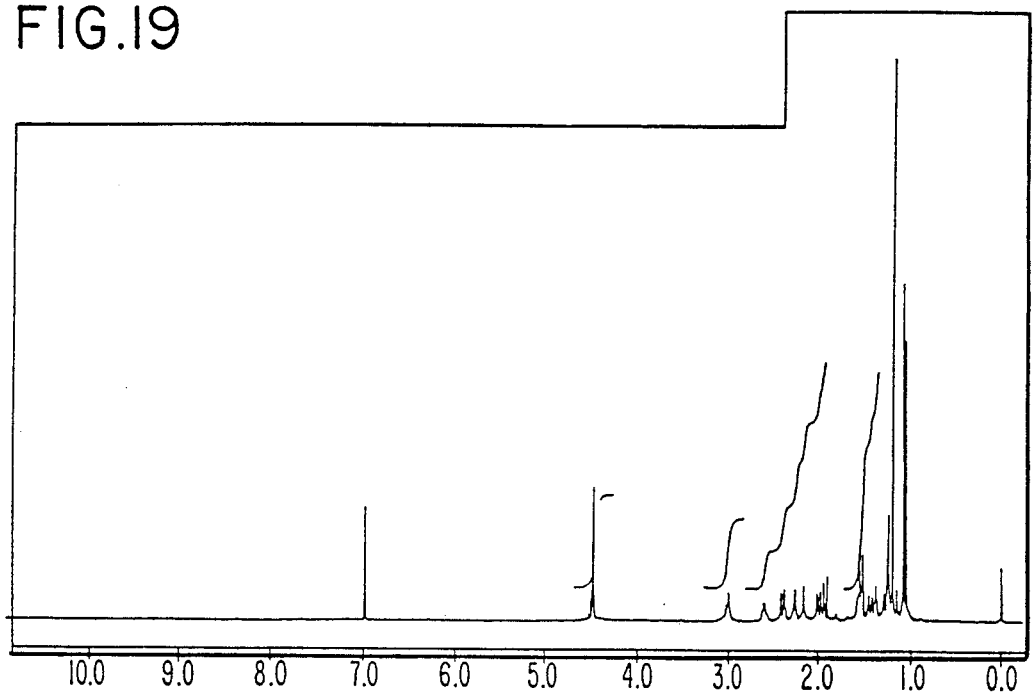

FIG. 19 is the NMR spectrum for the peak indicated by reference numeral 163 in FIG. 16 for a compound produced according to Example VIII.

Figure 20:
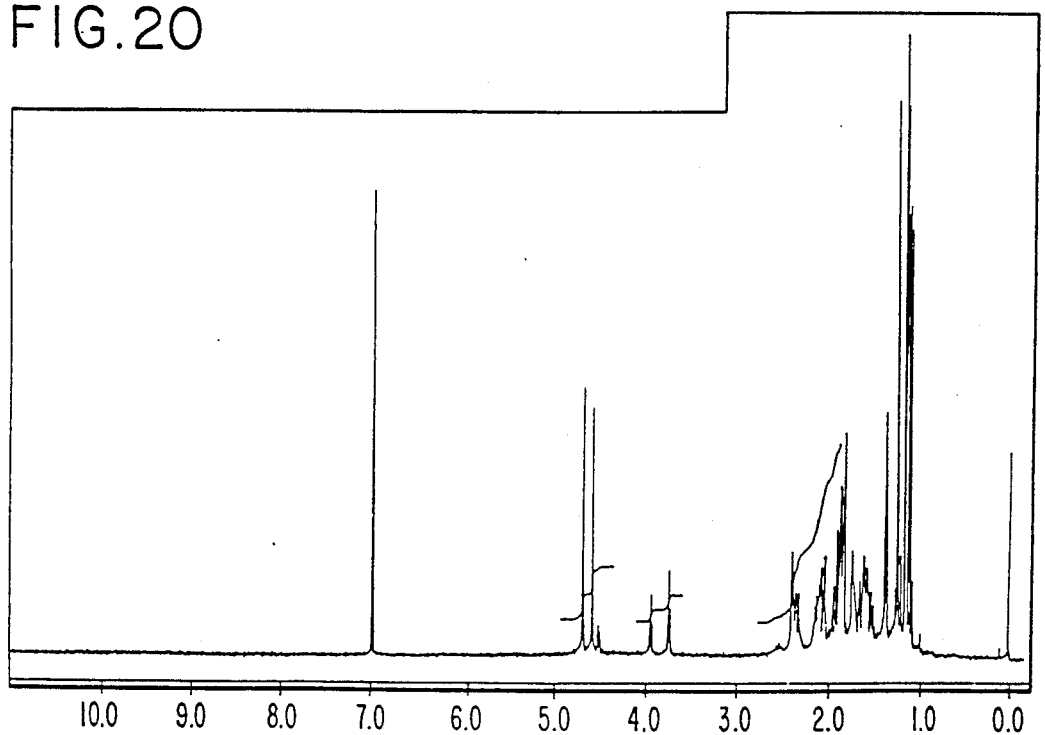

FIG. 20 is the NMR spectrum for the peak indicated by reference numeral 164 in FIG. 16; the compound having the structure:

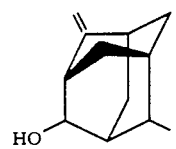

Figure 21:
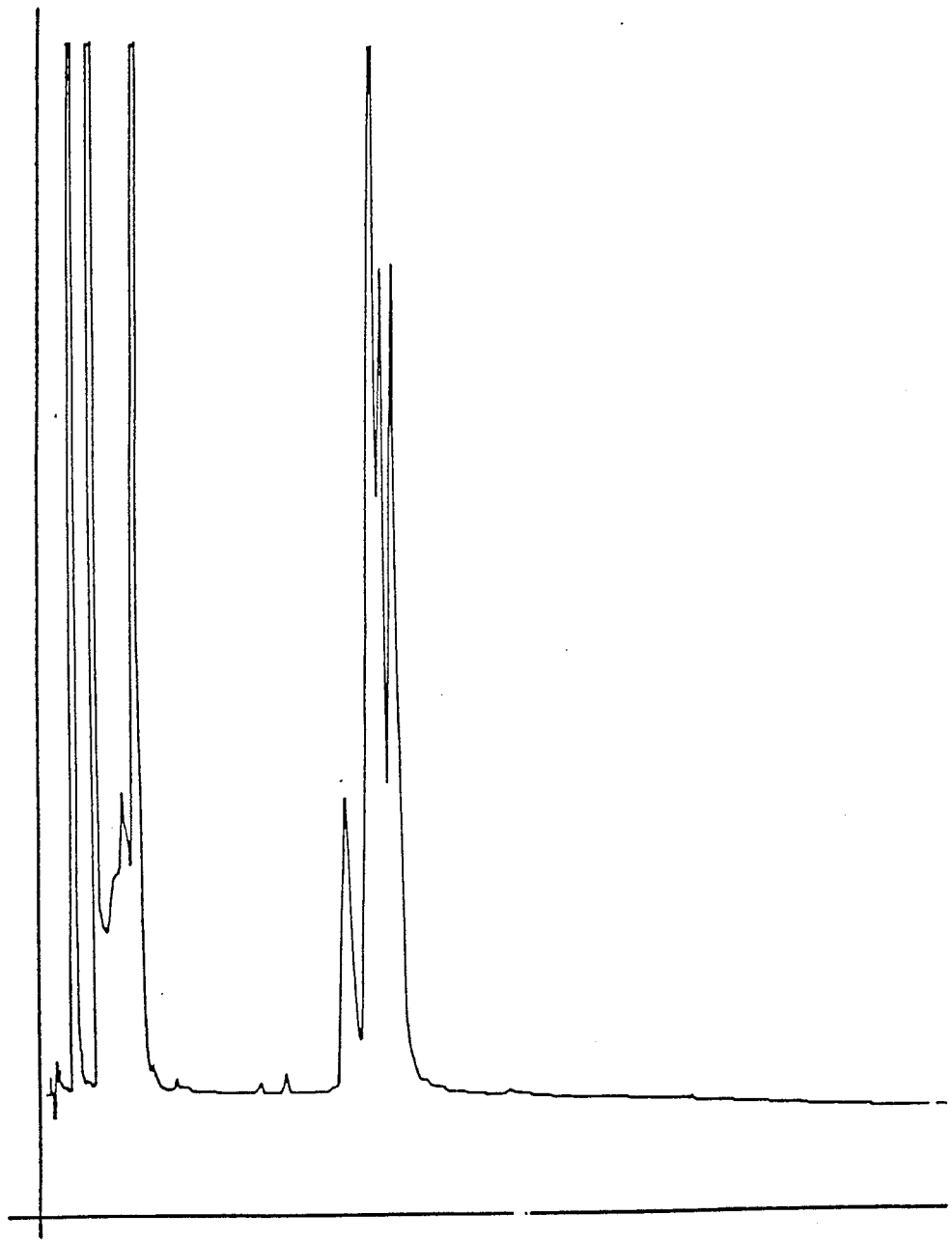

FIG. 21 is the GLC profile for the crude reaction product of Example IX containing the compound having the structure:

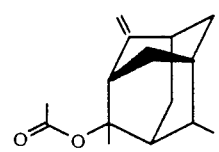

Figure 22:
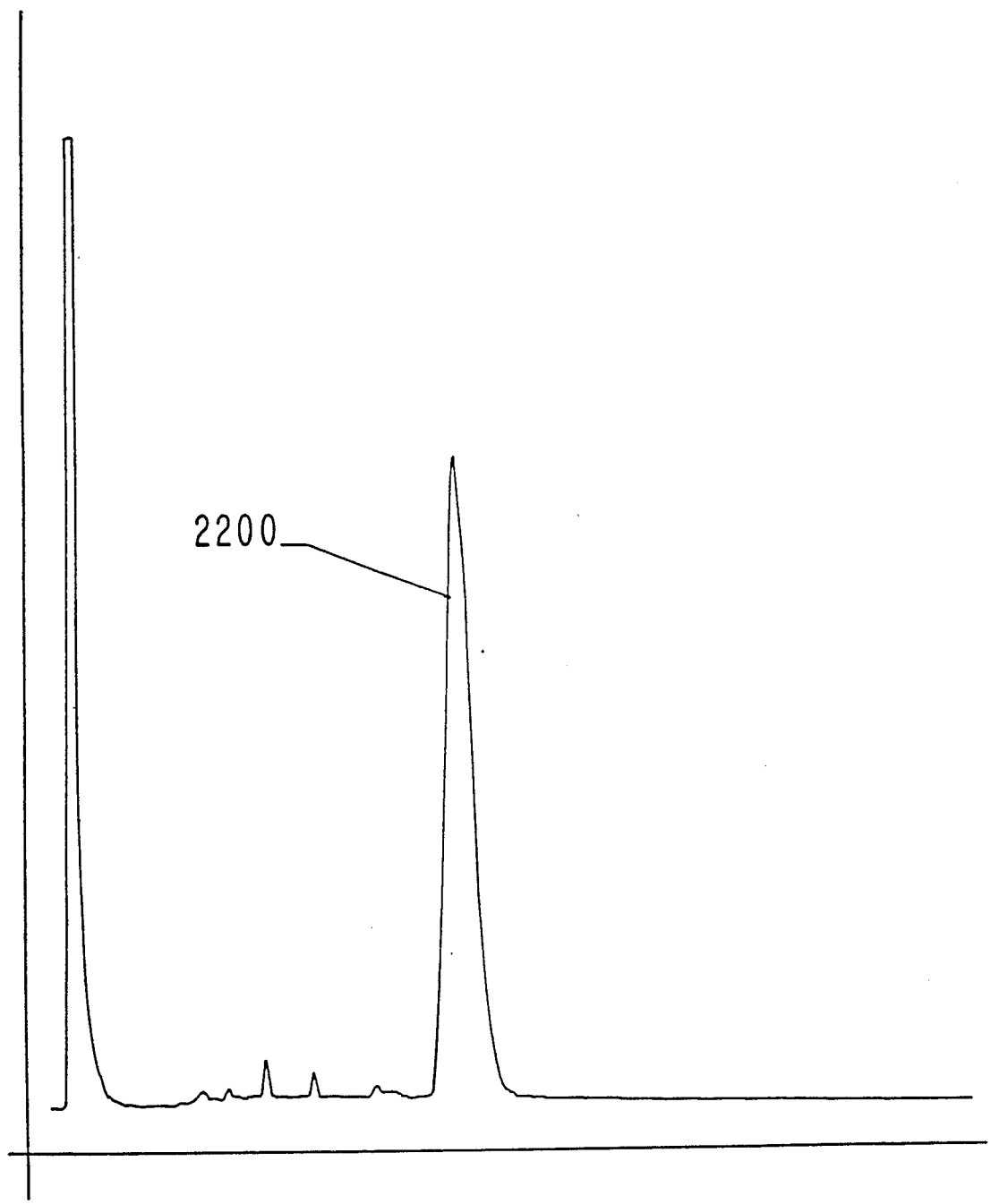

FIG. 22 is the GLC profile for the crude reaction product of Example X containing the compound having the structure:

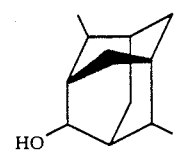

(Conditions: Carbowax column programmed at 130°-220° C.).

Figure 23:
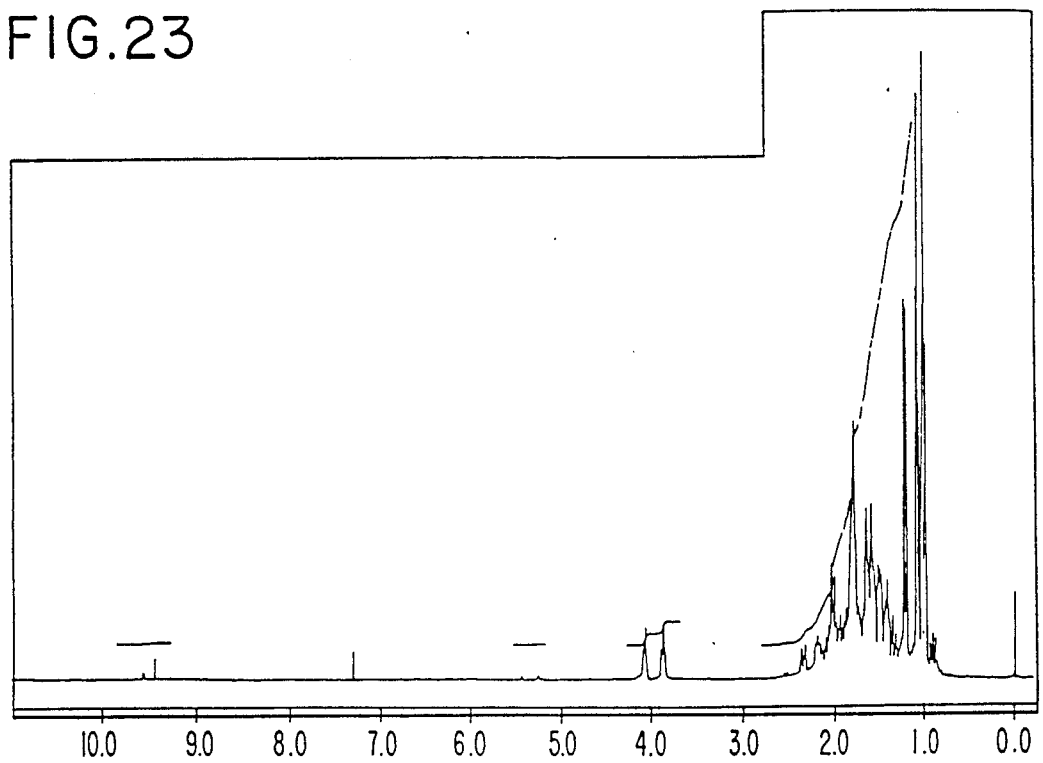

FIG. 23 is the NMR spectrum for the compound having the structure:

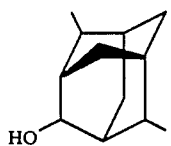

produced according to Example X.

Figure 24:
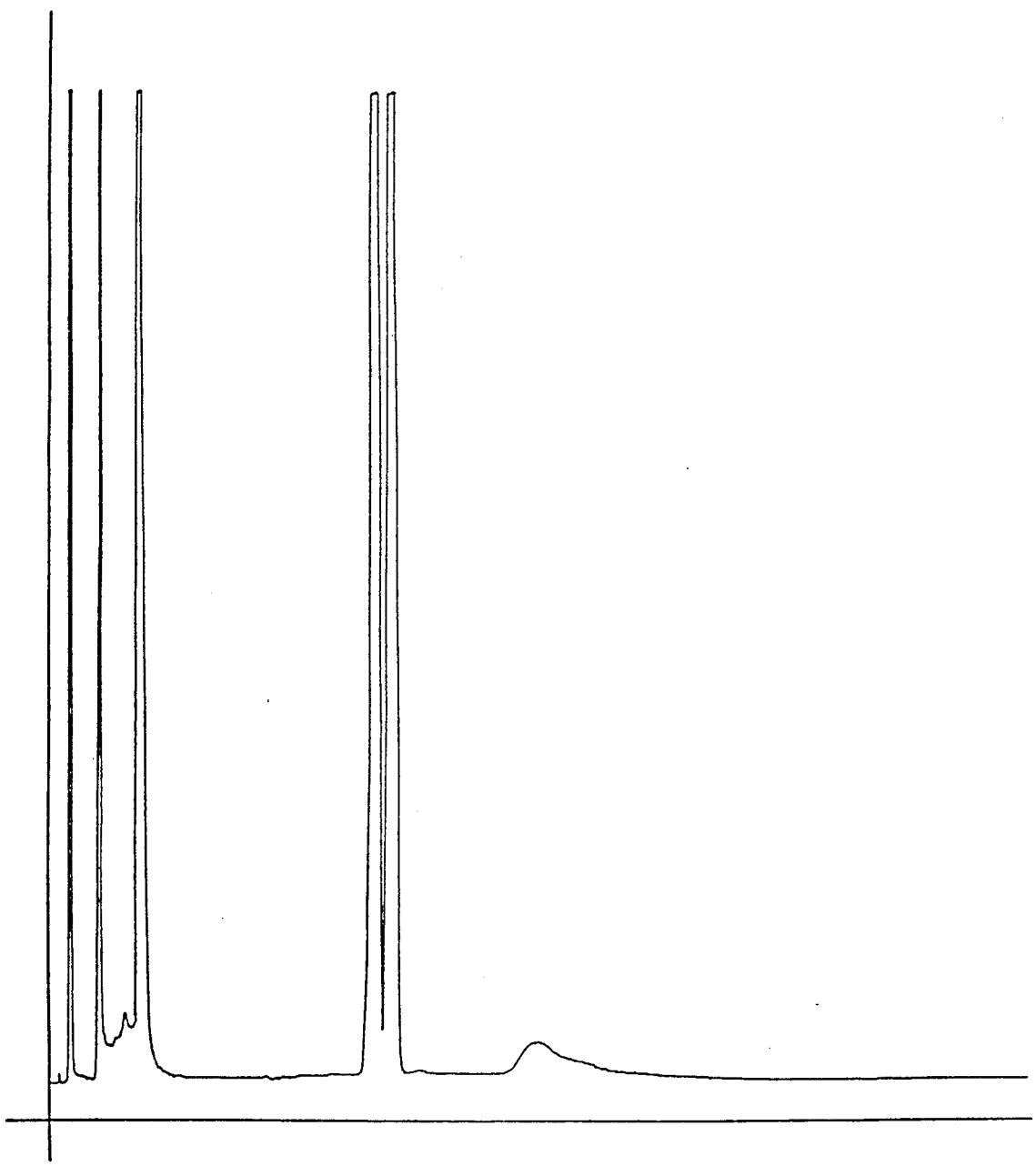

FIG. 24 is the GLC profile for the crude reaction product produced according to Example XI containing the compound having the structure:

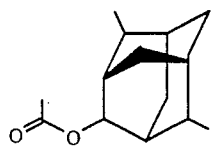

(Conditions: Carbowax column programmed at 130°-220° C.).

Figure 25:
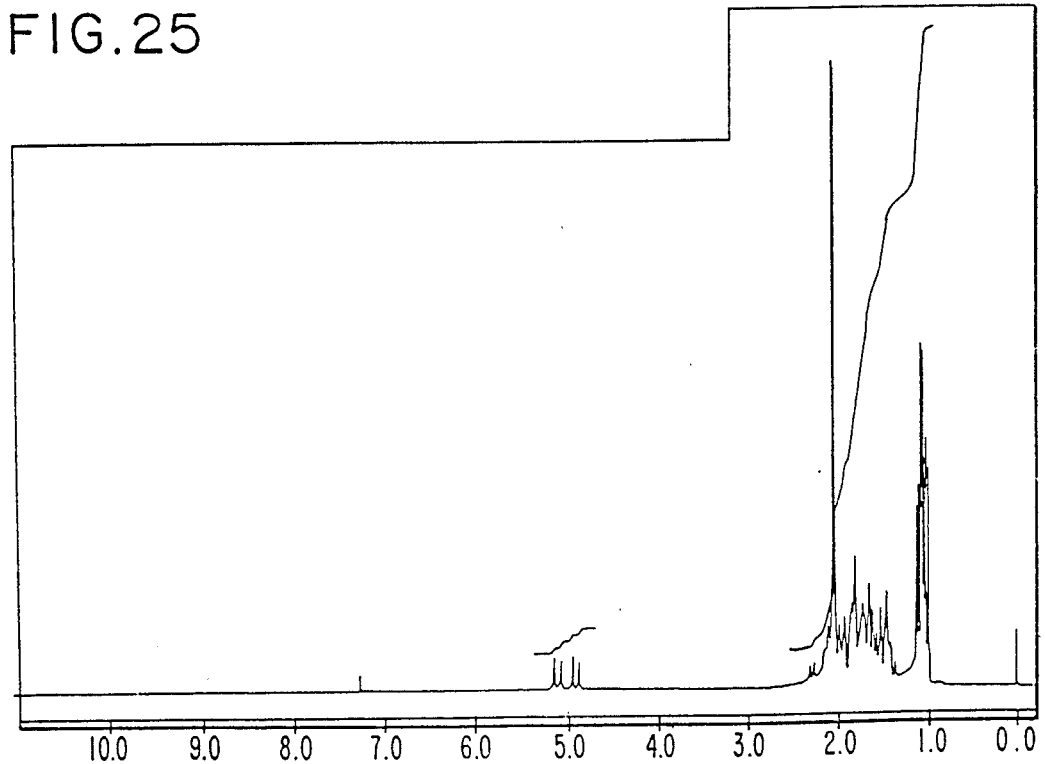

FIG. 25 is the NMR spectrum for the compound having the structure:

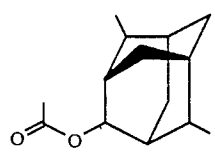

produced according to Example XI.

FIG. 26 is a partial side elevation and partial sectional view of an apparatus for forming polymer pellets containing at least one of the adamantane derivatives of our invention.

FIG. 27 is a section taken along line 27-27 of FIG. 26.

Figure 28:
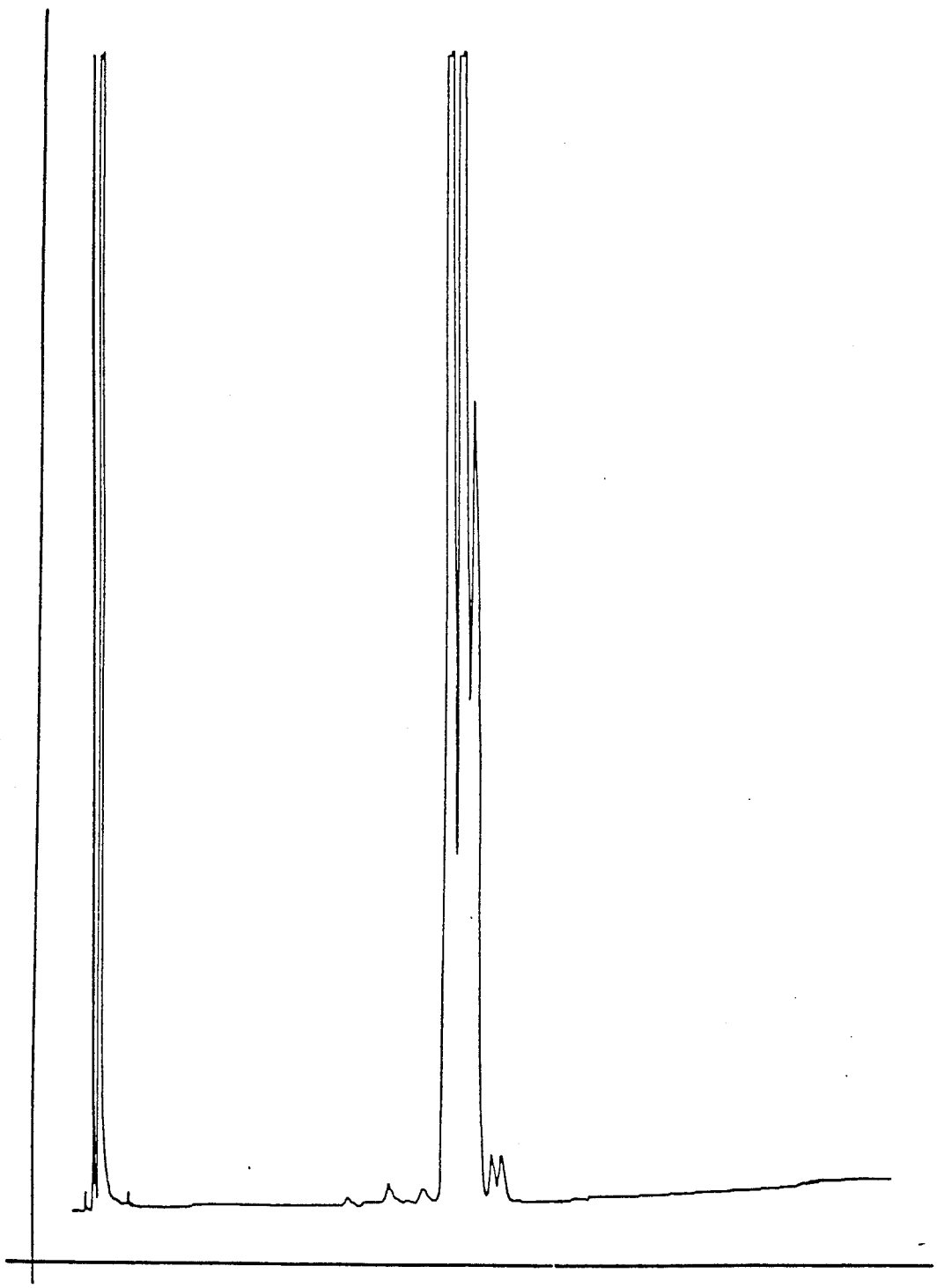

FIG. 28 is the GLC profile for the crude reaction product of Example XII containing the compound having the structure:

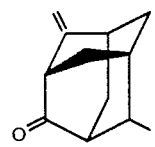

(Conditions: SE-30 column programmed at 130°-220° C. at 8° C. per minute).

Figure 29:
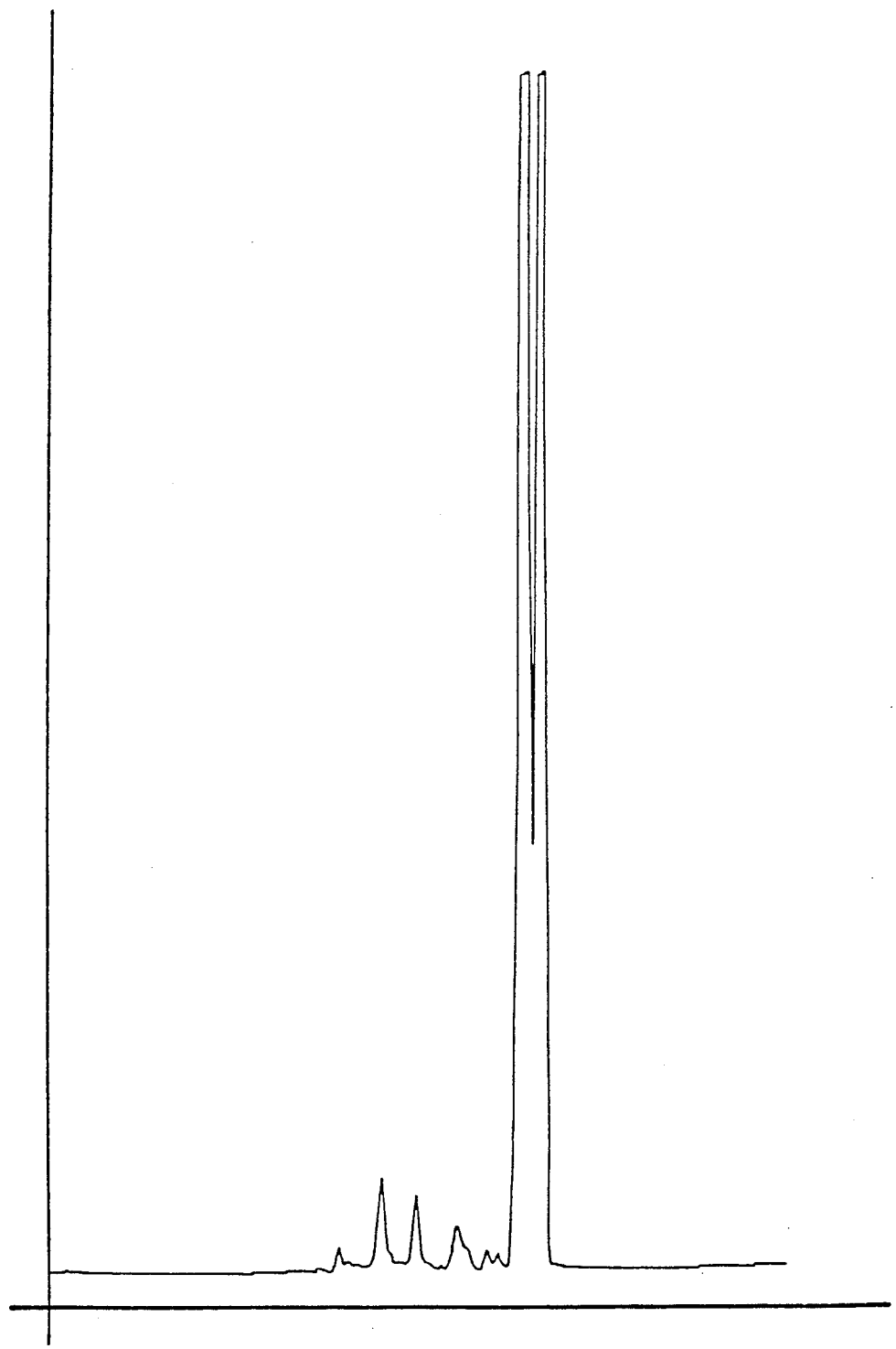

FIG. 29 is the GLC profile for the crude reaction product of Example XIII containing the compound having the structure:

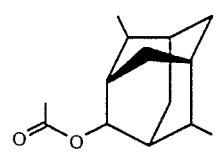

(Conditions: SE-30 column programmed at 130°-220° C. at 8° C. per minute).

Figure 30:
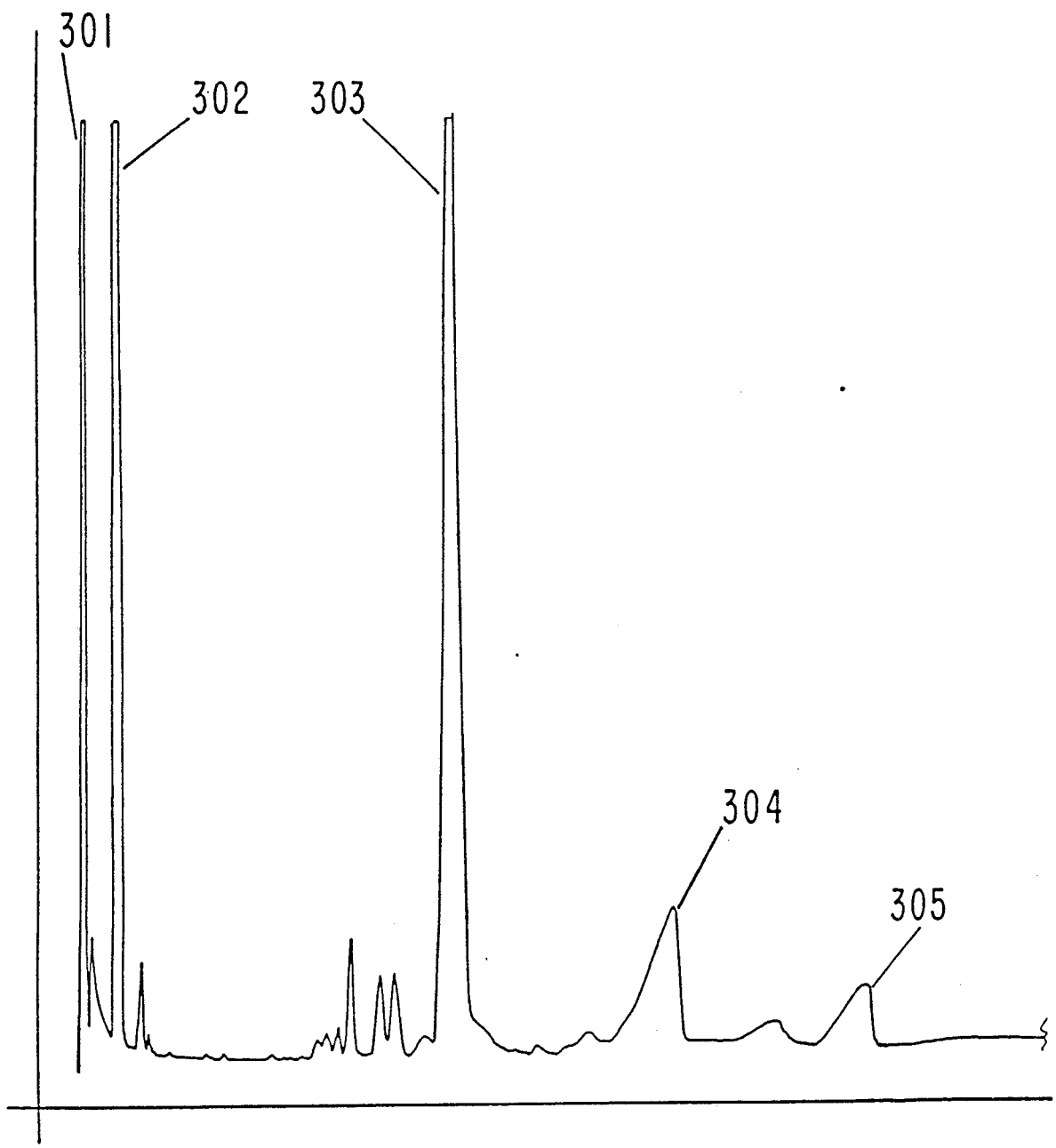

FIG. 30 is the GLC profile for the crude reaction product of Example XIV containing the compounds having the structures:

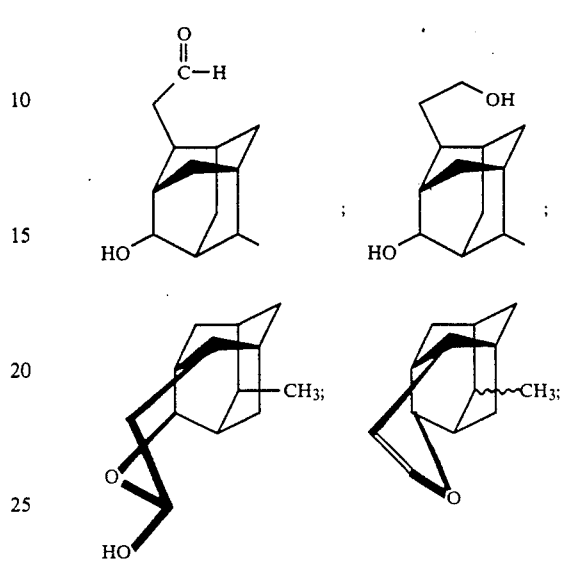

(Conditions: SE-30 column programmed at 130°-220° C. at 8° C. per minute).

Figure 31:
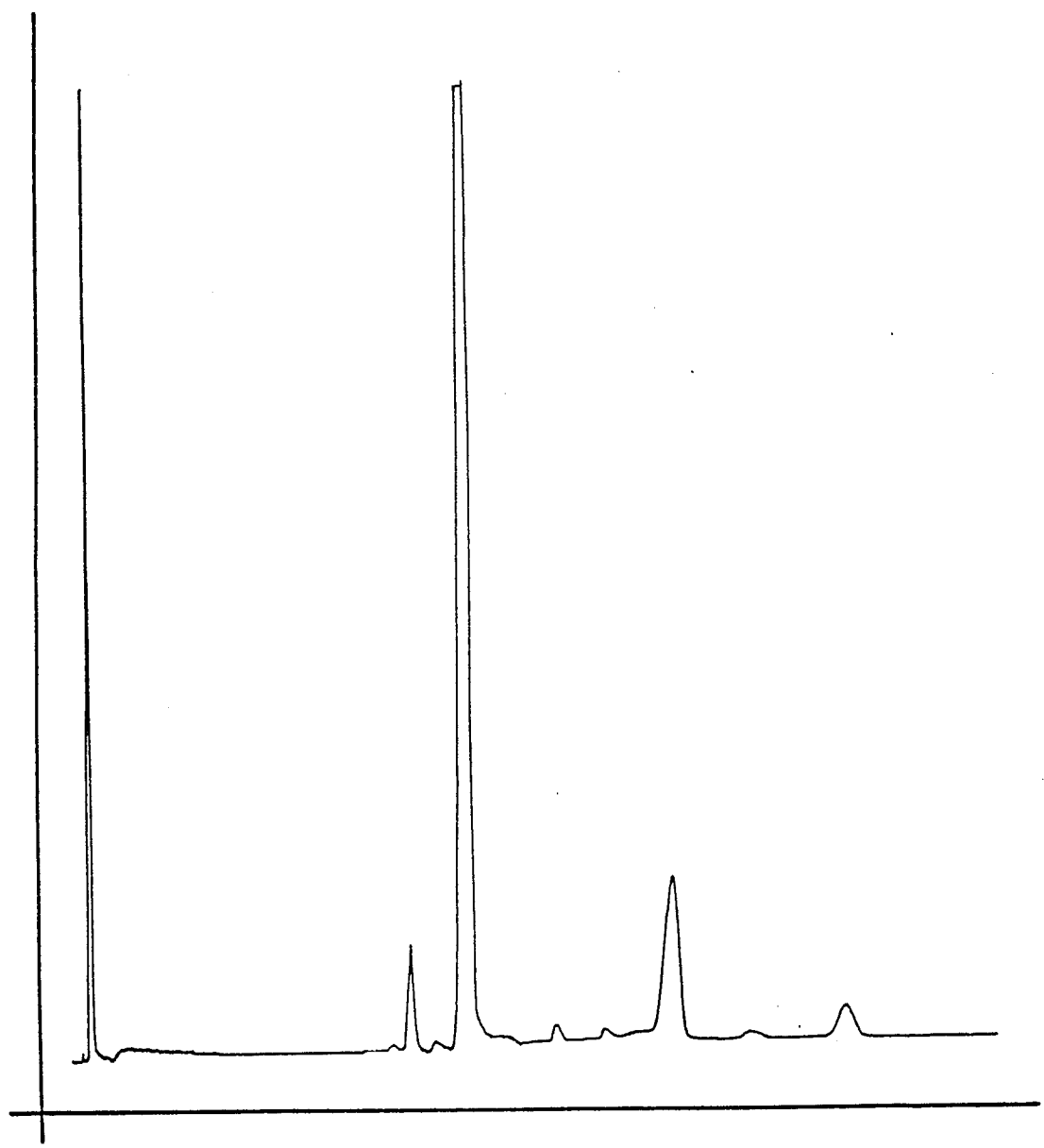

FIG. 31 is the GLC profile for distillation fraction 6 of the distillation product of the reaction product of Example XIV.

Figure 32:
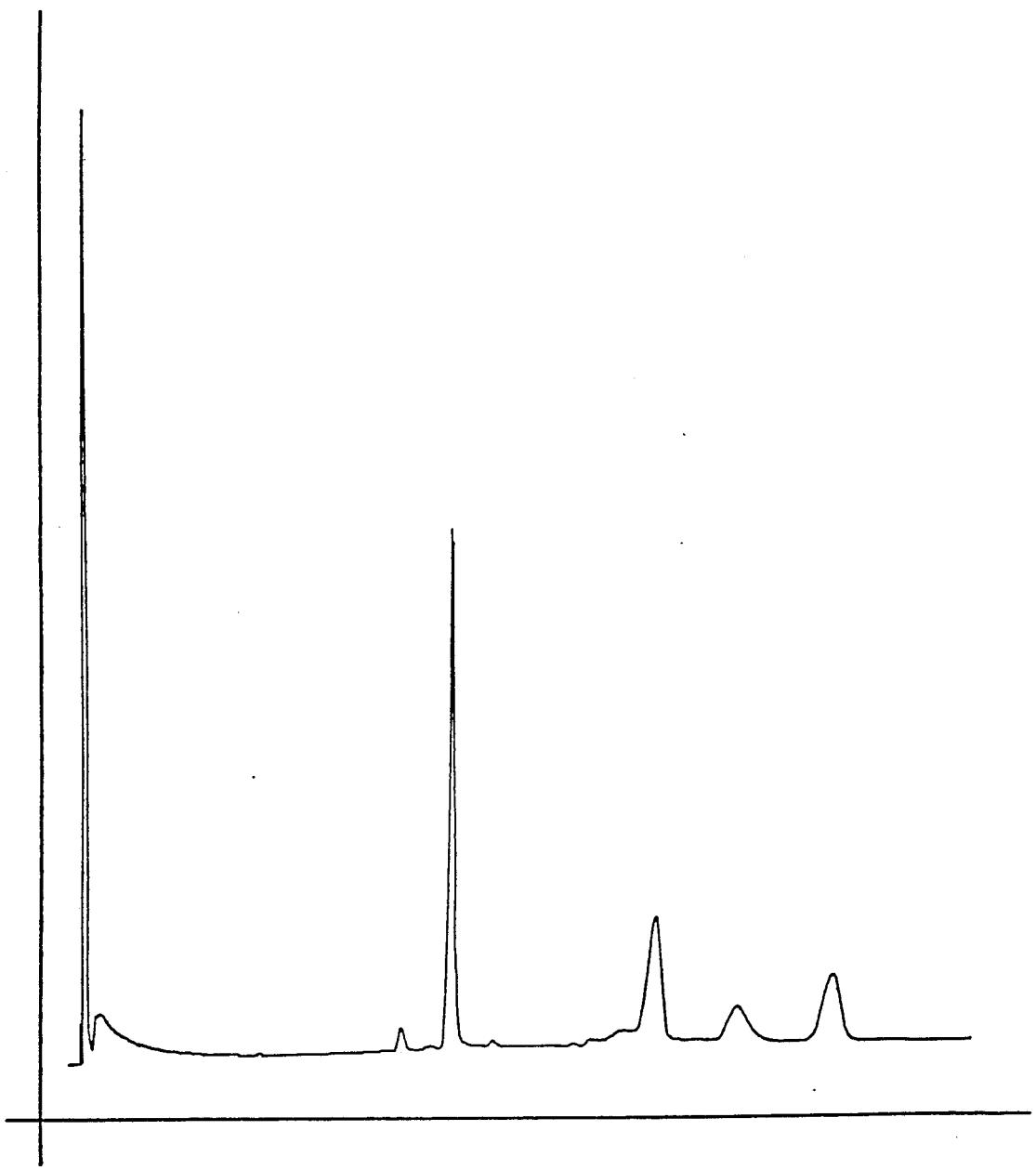

FIG. 32 is the GLC profile for distillation fraction 7 of the distillation product of the reaction product of Example XIV (Conditions: SE-30 column programmed at 130°-220° C. at 8° C. per minute).

Figure 33:
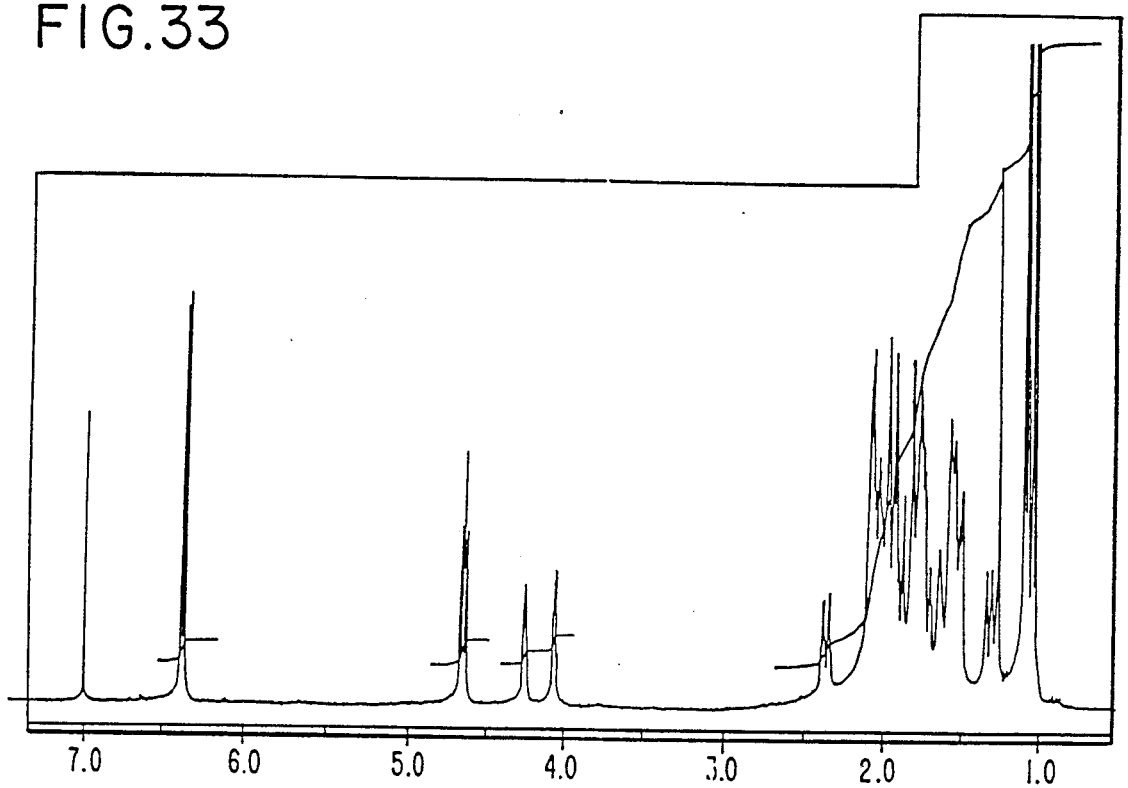

FIG. 33 is the NMR spectrum for the peak indicated by reference numeral 303 of the GLC profile of FIG. 30; the compound having the structure:

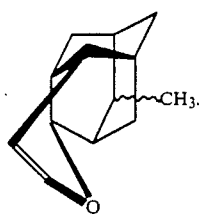

Figure 34:
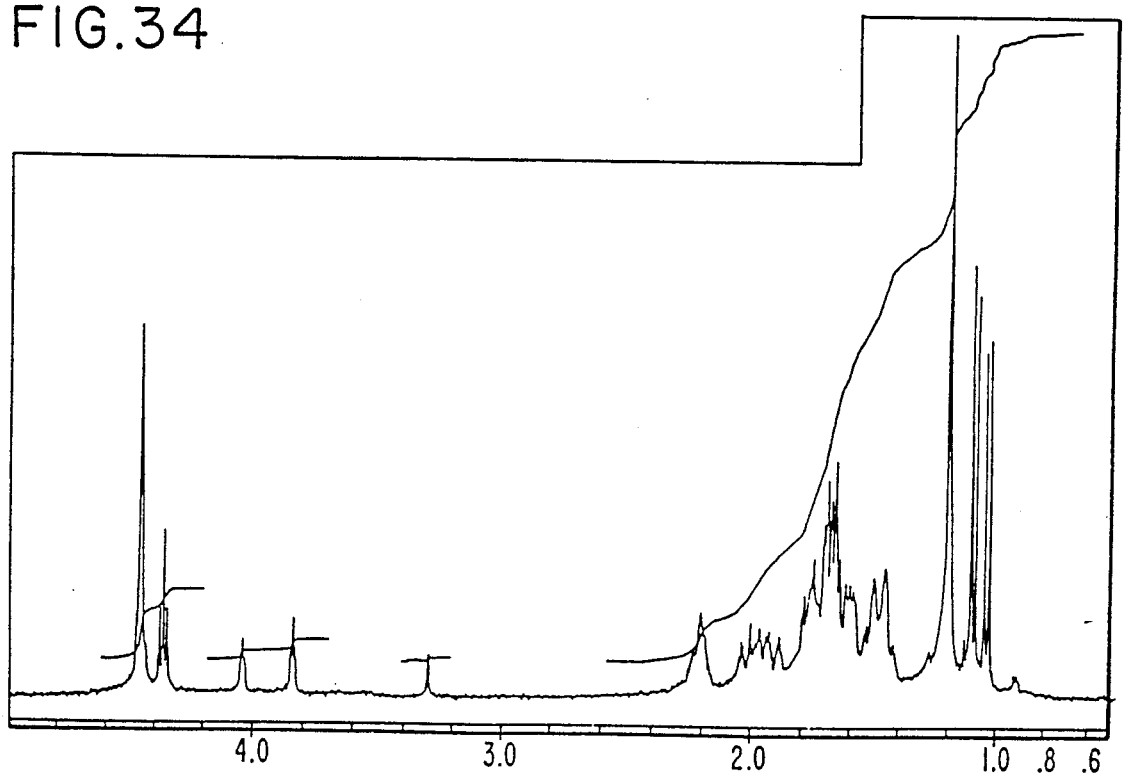

FIG. 34 is the NMR spectrum for the compound having the structure:

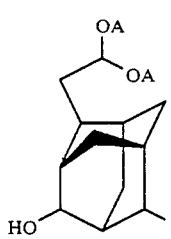

wherein A is the methyladamantyloxy moiety.

Figure 35:
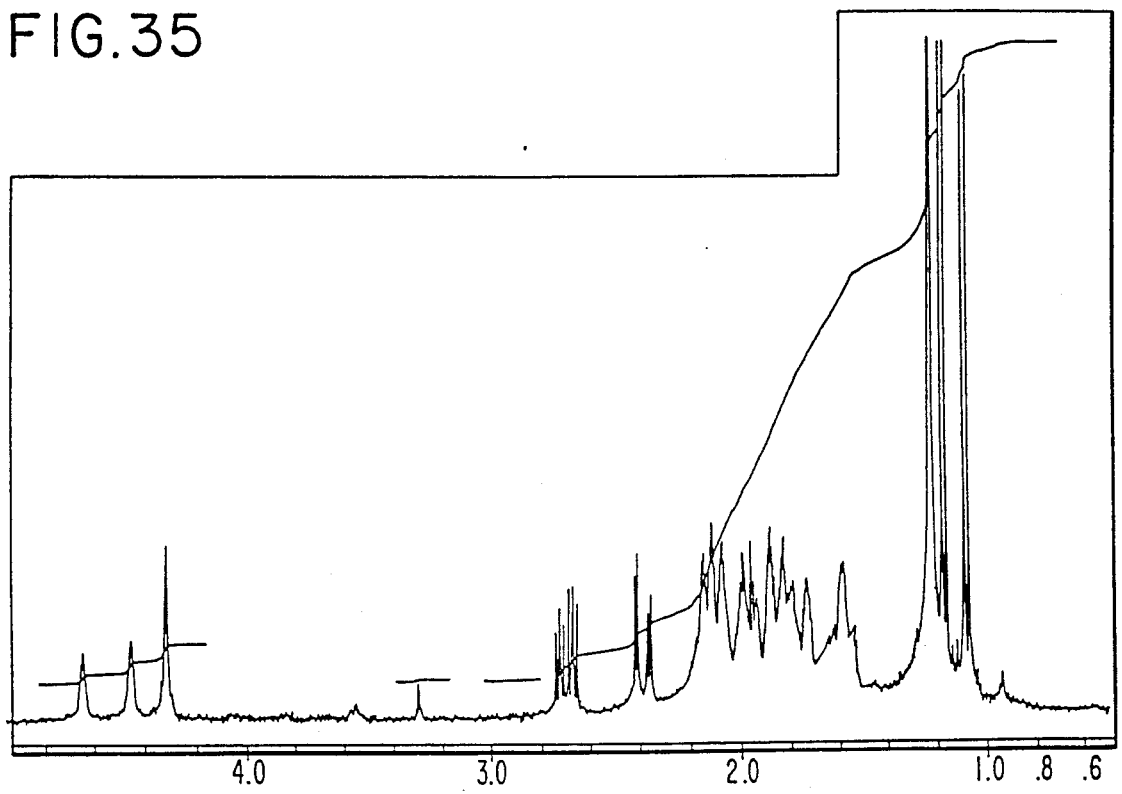

FIG. 35 is the NMR spectrum for the peak indicated by reference numeral 305 on the GLC profile of FIG. 30; for the compound having the structure:

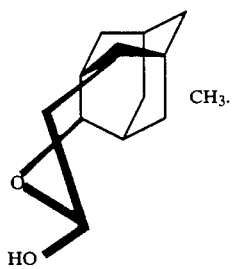

Figure 36:
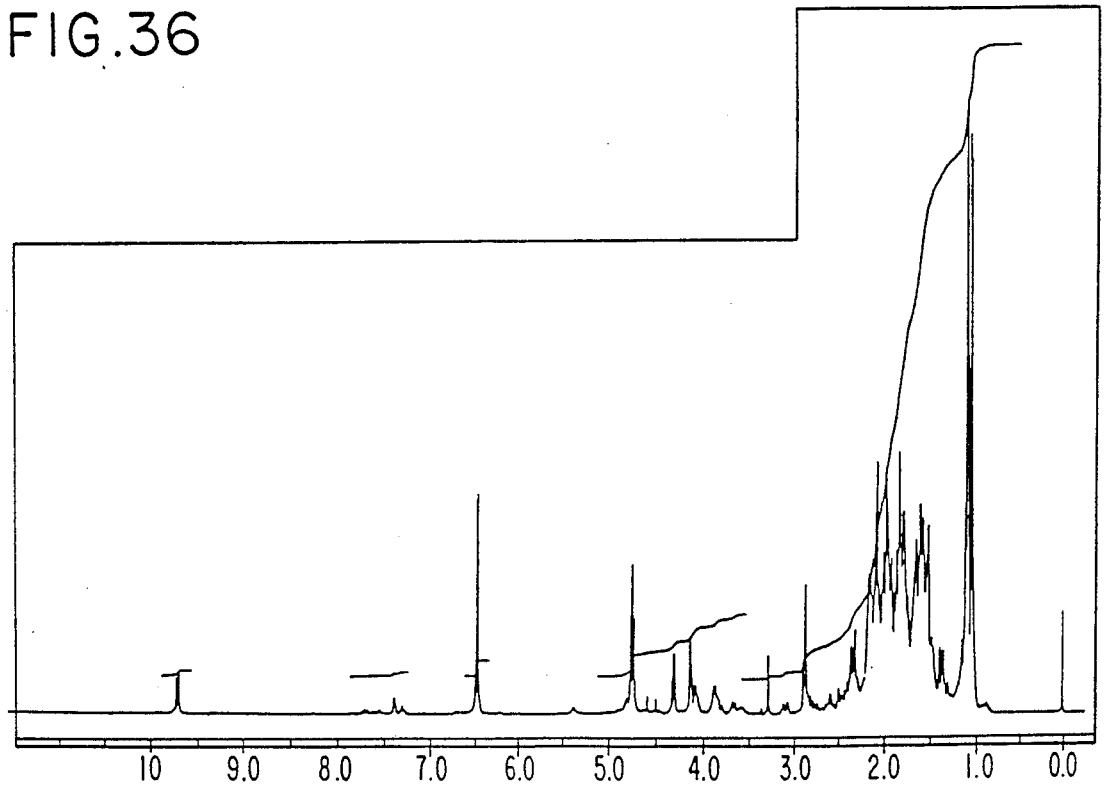

FIG. 36 is the NMR spectrum for distillation fraction 6 of the distillation product of the reaction product of Example XIV containing the compounds having the structures:

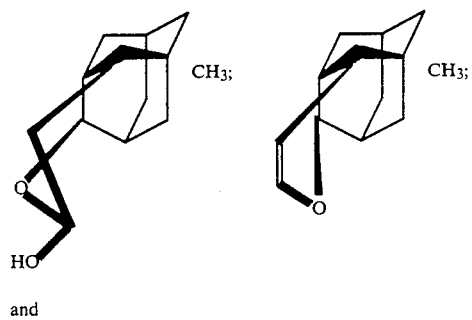

Figure 37:
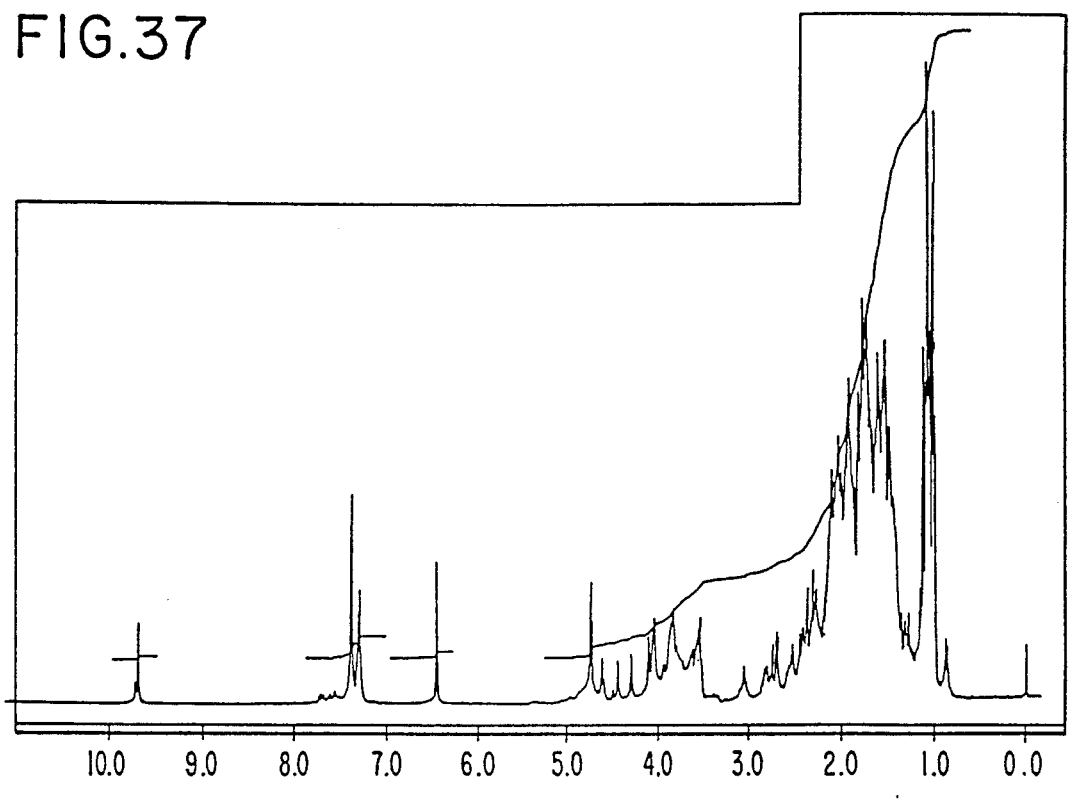

FIG. 37 is the NMR spectrum for distillation fraction 8 of the distillation product of the reaction product of Example XIV containing the compounds having the structures:

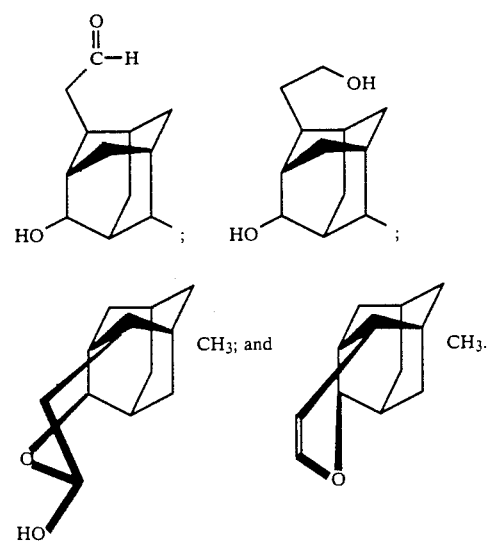

FIG. 37A is the GLC profile for the crude reaction product of Example XV containing the compounds having the structures:

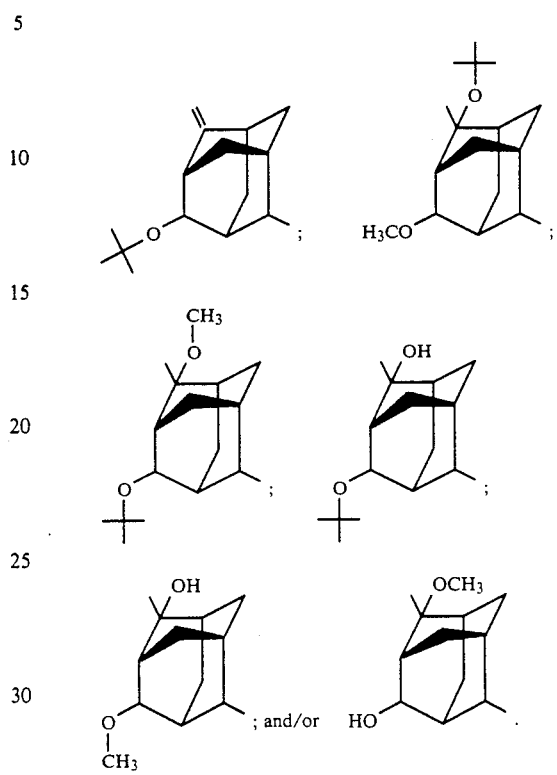

FIG. 37B is the GLC profile for distillation fraction 3 of the distillation product of the reaction product of Example XV containing the structures:

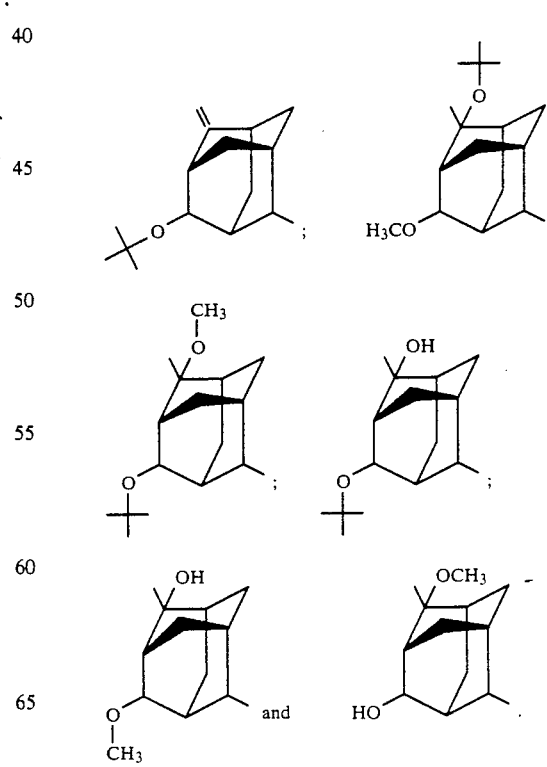

FIG. 37C is another GLC profile of distillation fraction 3 of the distillation product of the reaction product of Example XV.

Figure 38:
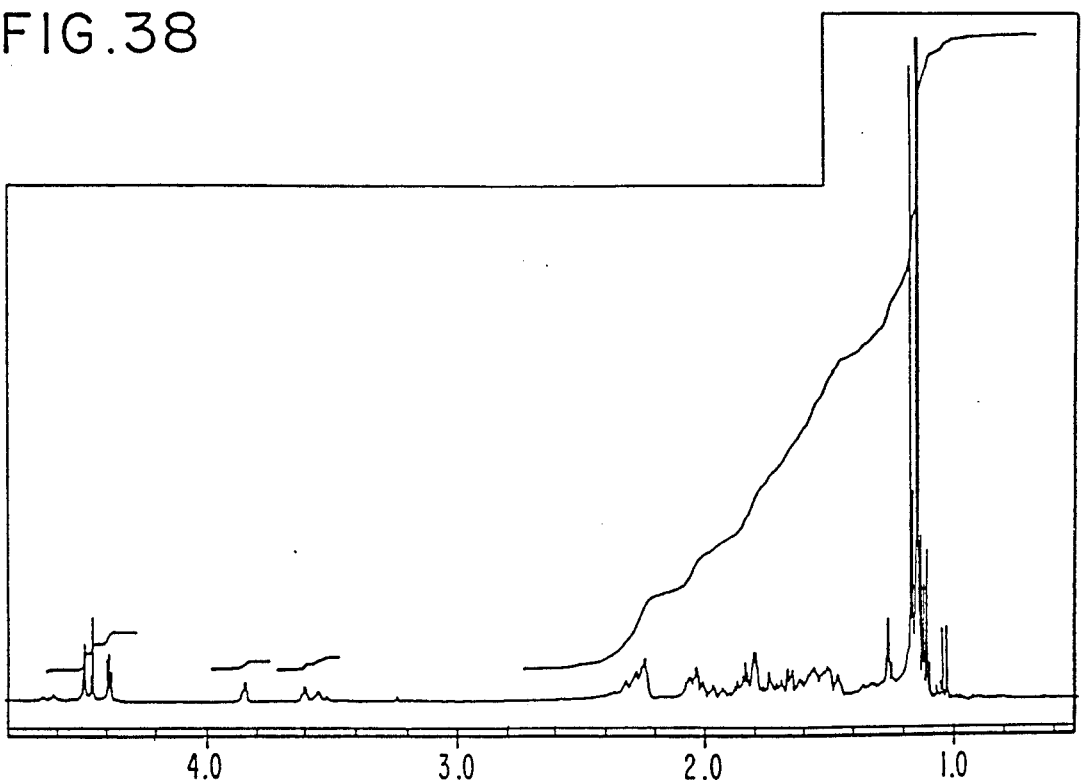

FIG. 38 is the NMR spectrum for peak group 371 of the GLC profile of FIG. 37B of distillation fraction 3 of the distillation product of the reaction product of Example XV for the compound having the structure:

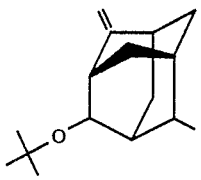

Figure 39:
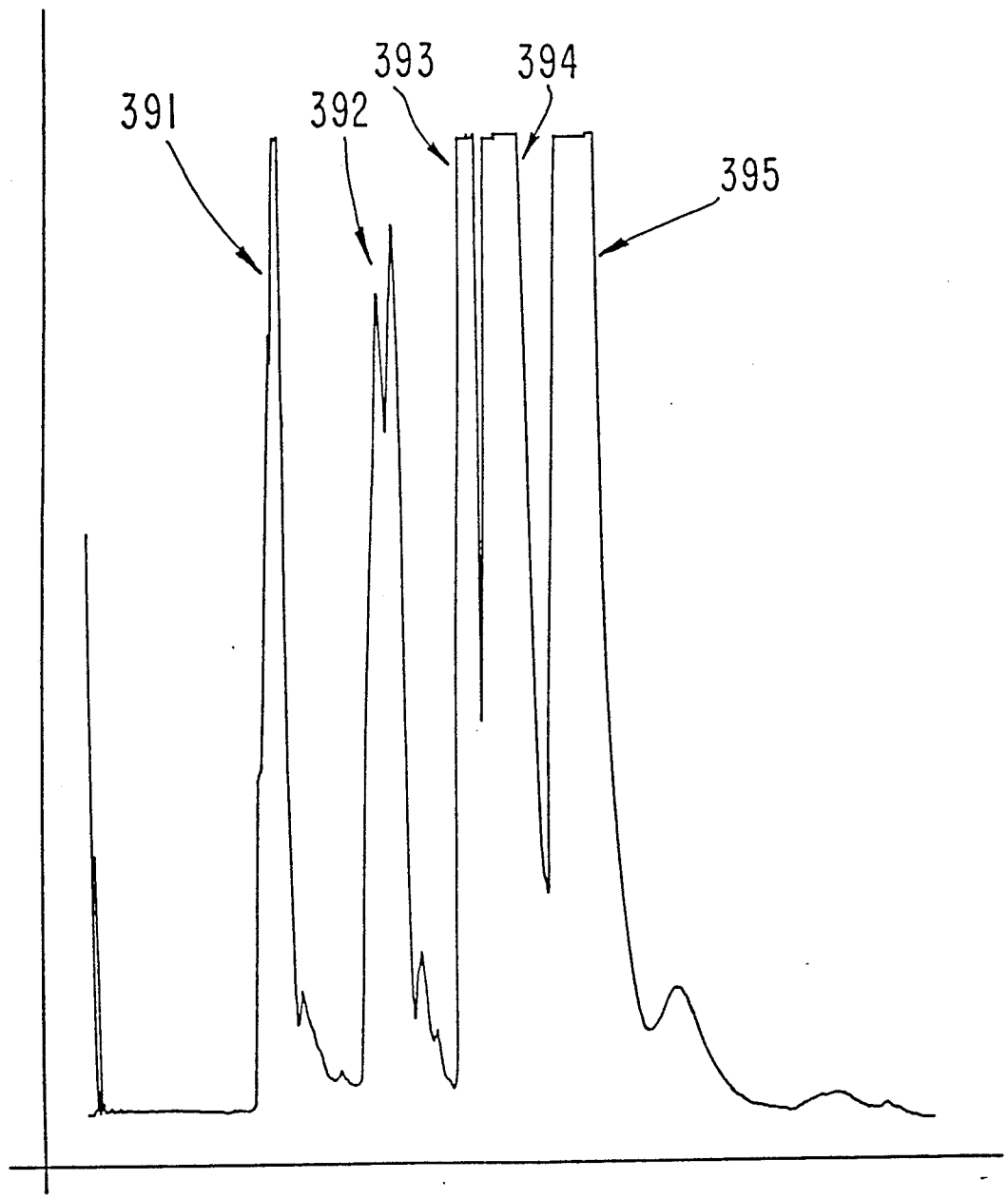

FIG. 39 is the GLC profile for distillation fraction 6 of the distillation product of the reaction product of Example XV containing the compounds having the structures:

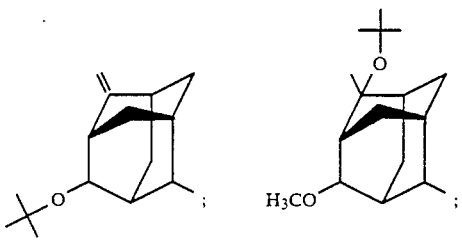

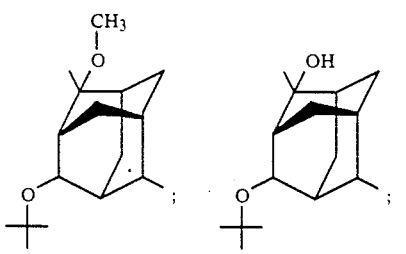

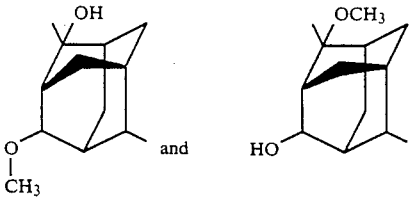

Figure 40:
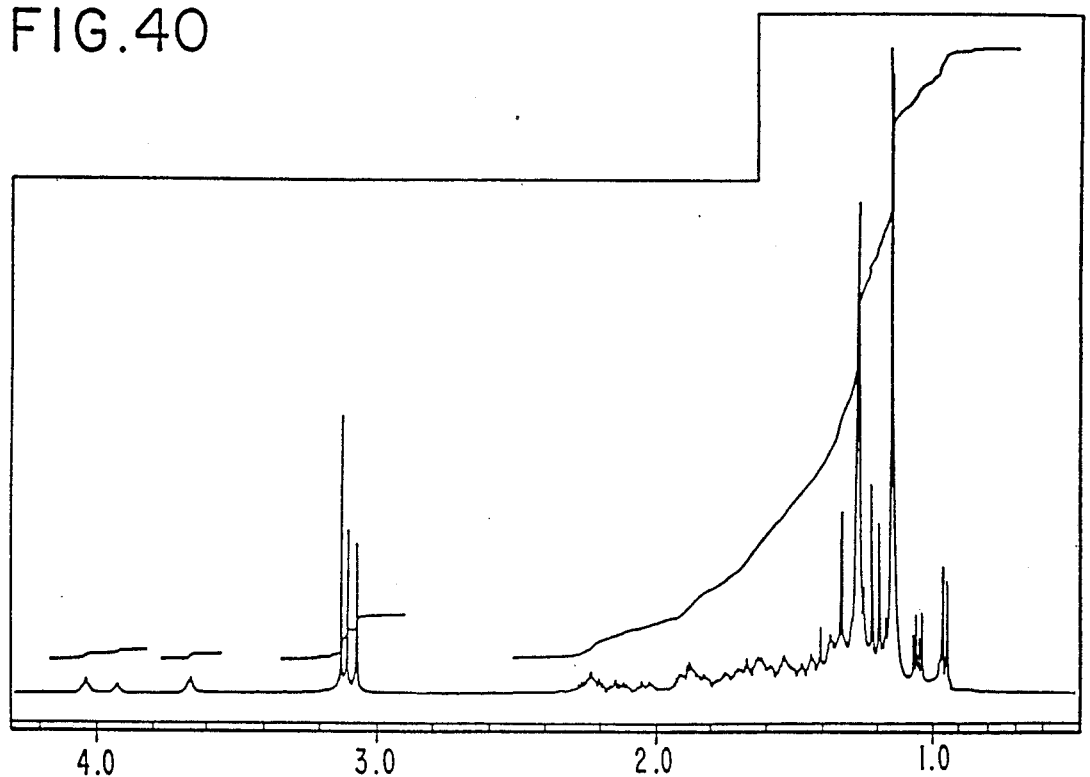

FIG. 40 is the NMR spectrum for peak group 392 of the GLC profile of FIG. 39 for distillation fraction 6 of the distillation product of the reaction product of Example XV; one or a mixture of the compounds having the structures:

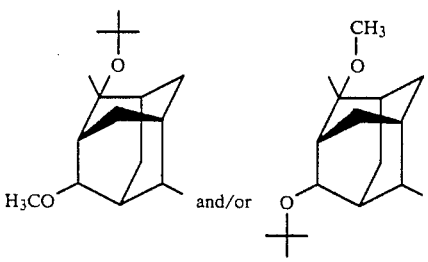

Figure 41:
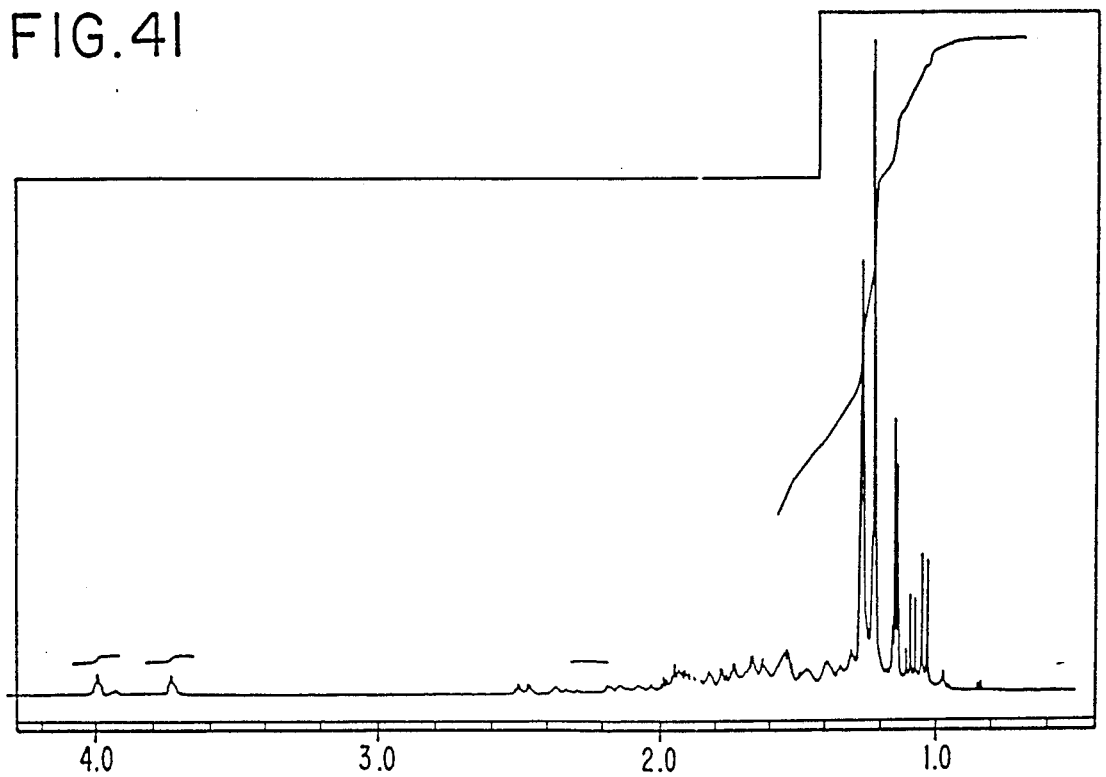

FIG. 41 is the NMR spectrum for the peak group 393 of the GLC profile of FIG. 39 of the distillation fraction 6 of the distillation product of Example XV and is for the compound having the structure:

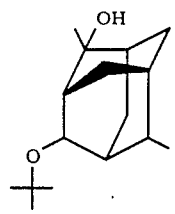

Figure 42:
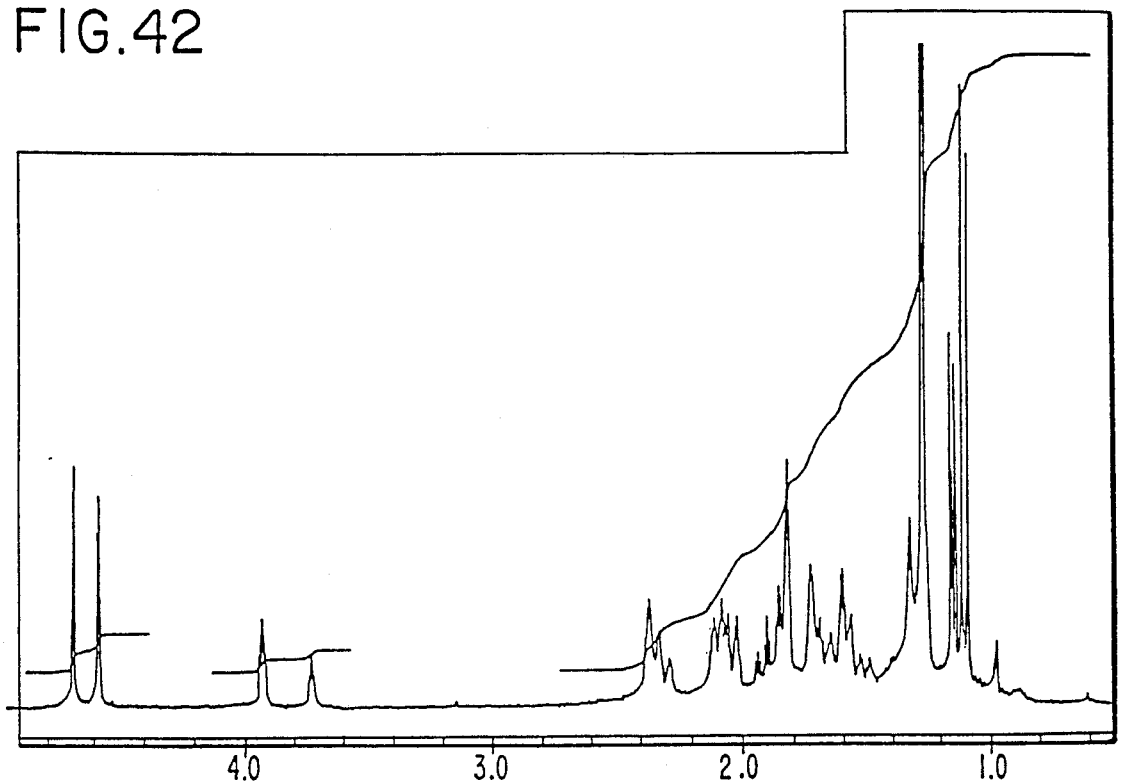

FIG. 42 is the NMR spectrum of peak group 394 of the GLC profile of FIG. 39 for distillation fraction 6 of the distillation product of the reaction product of Example XV; and is for the compound having the structure:

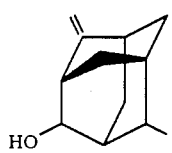

the starting material for the reaction.

Figure 43:
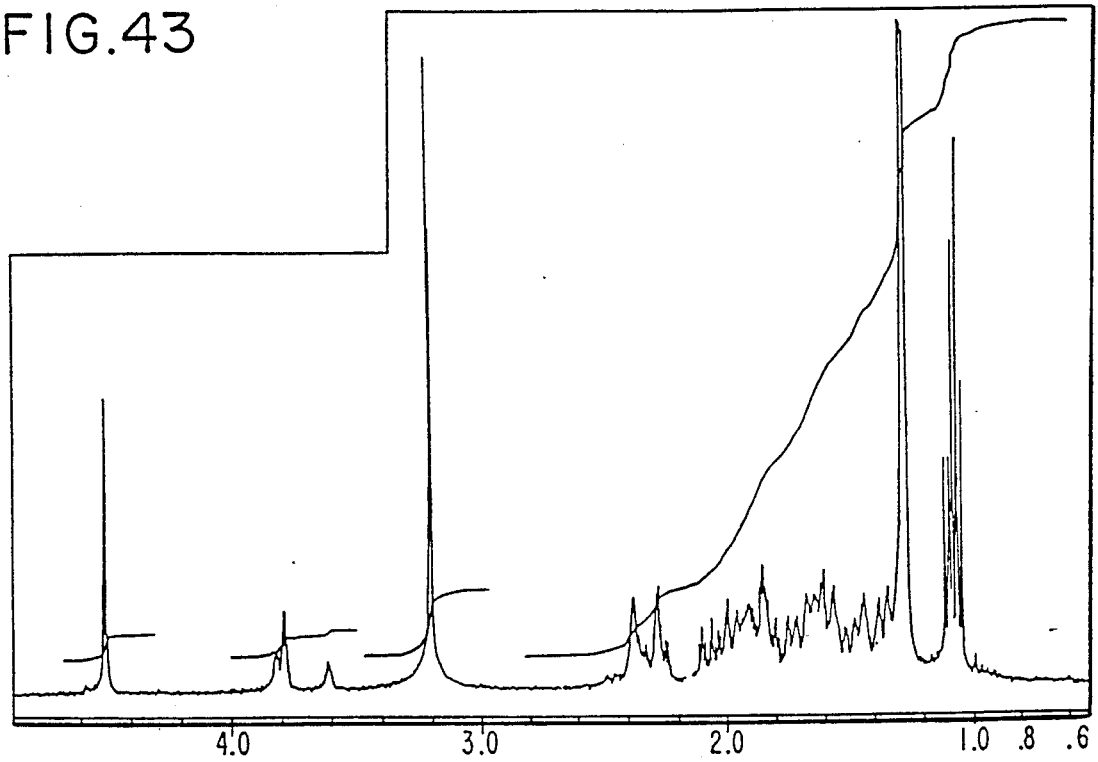

FIG. 43 is the NMR spectrum for the peak indicated by reference numeral 395 of the GLC profile of FIG. 39 for distillation fraction 6 of the distillation product of the reaction product of Example XV; and is for one or both of the compounds having the structures:

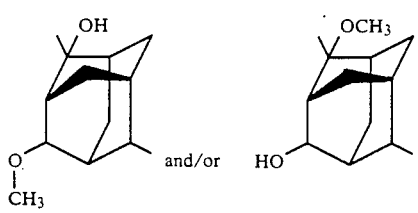

Figure 44:
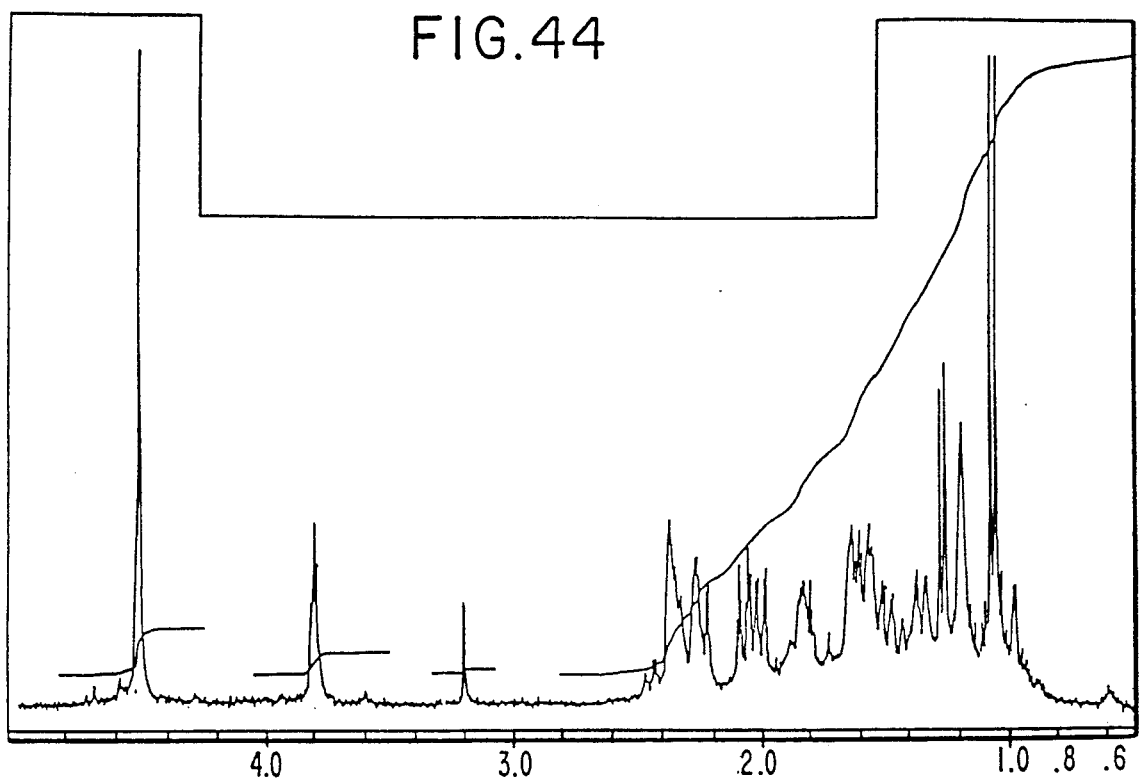

FIG. 44 is the NMR spectrum for the peak indicated by reference numeral 372 of the GLC profile of FIG. 37C; and is for one or both of the epimers having the structures:

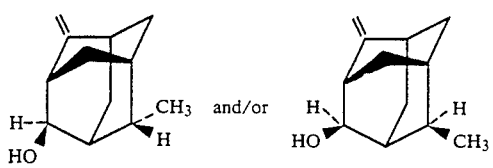

Figure 45:
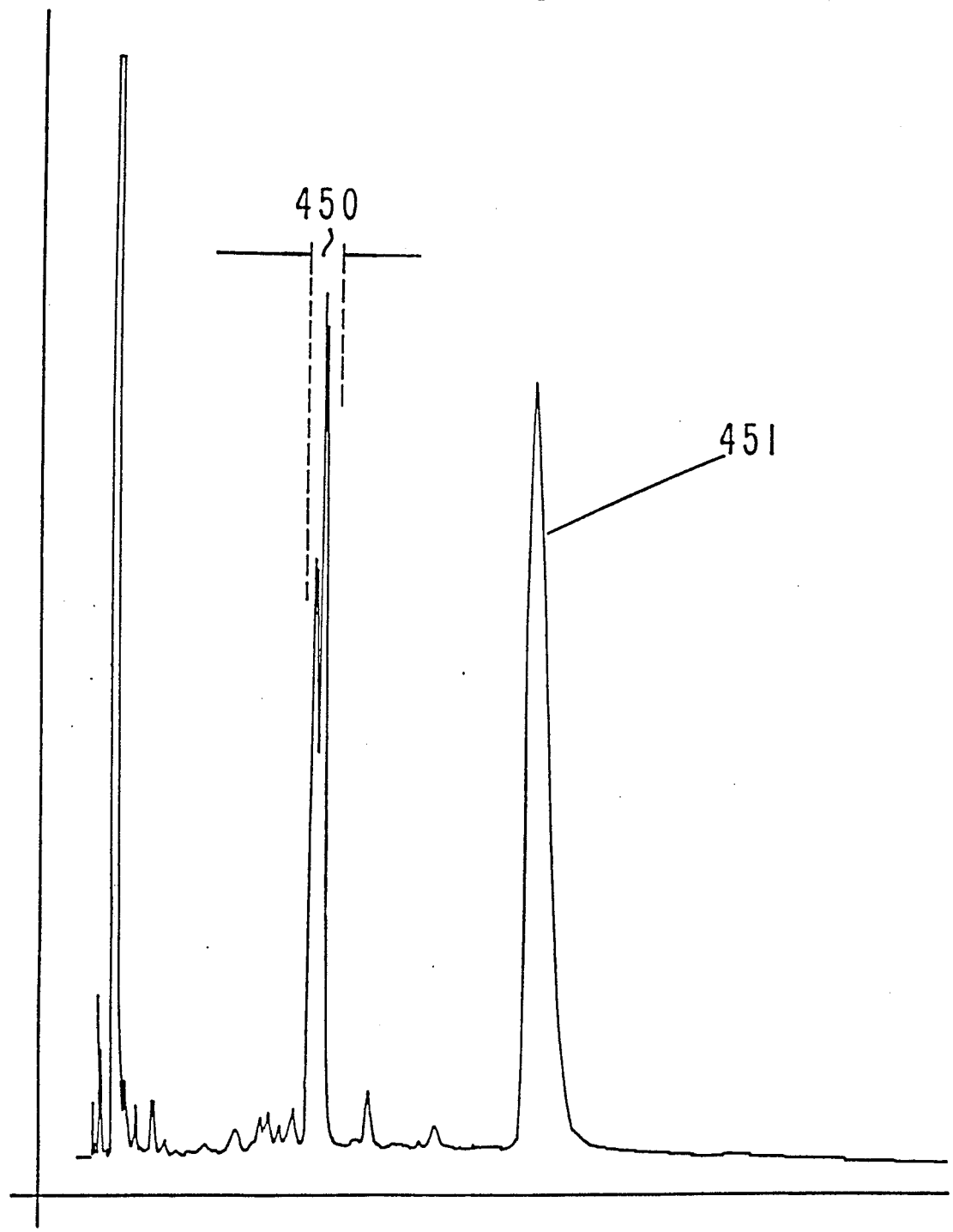

FIG. 45 is the GLC profile for the crude reaction product of Example XVI containing the compound having the structure:

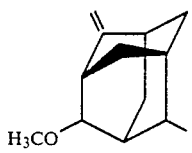

Figure 46:
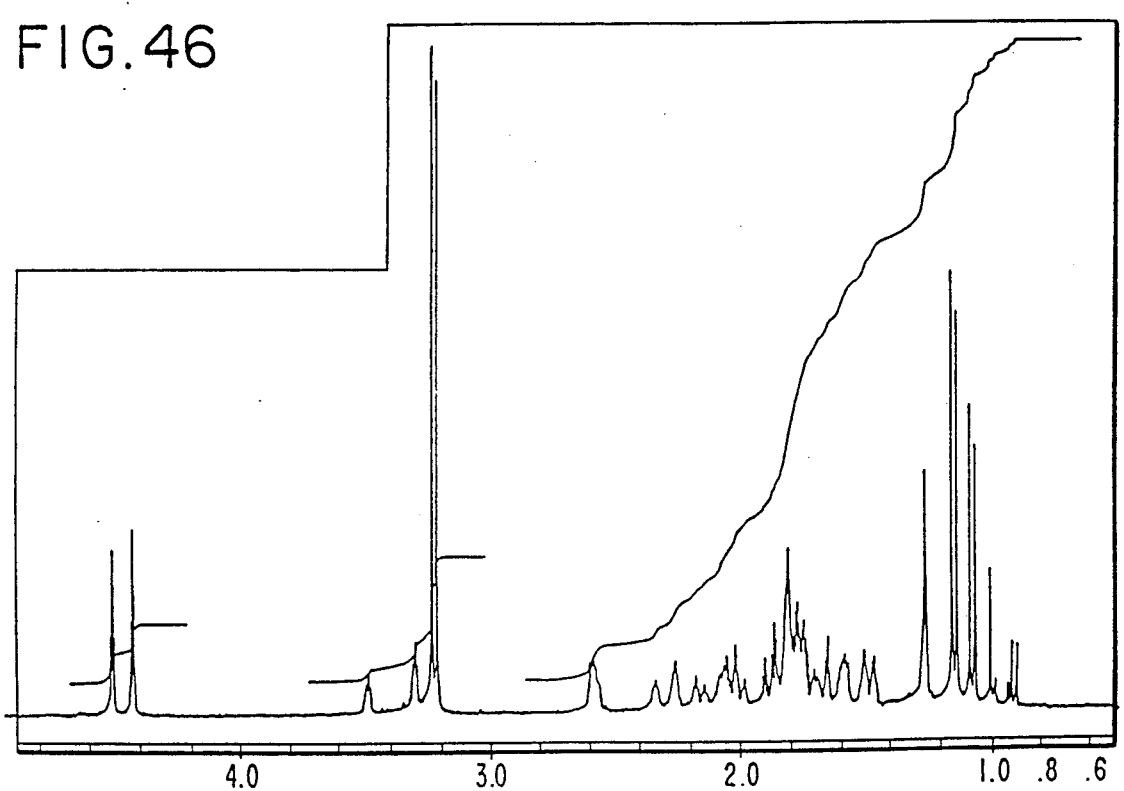

FIG. 46 is the NMR spectrum for the compound having the structure:

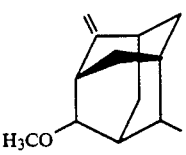

according to Example XVI.

DETAILED DESCRIPTION OF THE DRAWINGS

Figure 47:
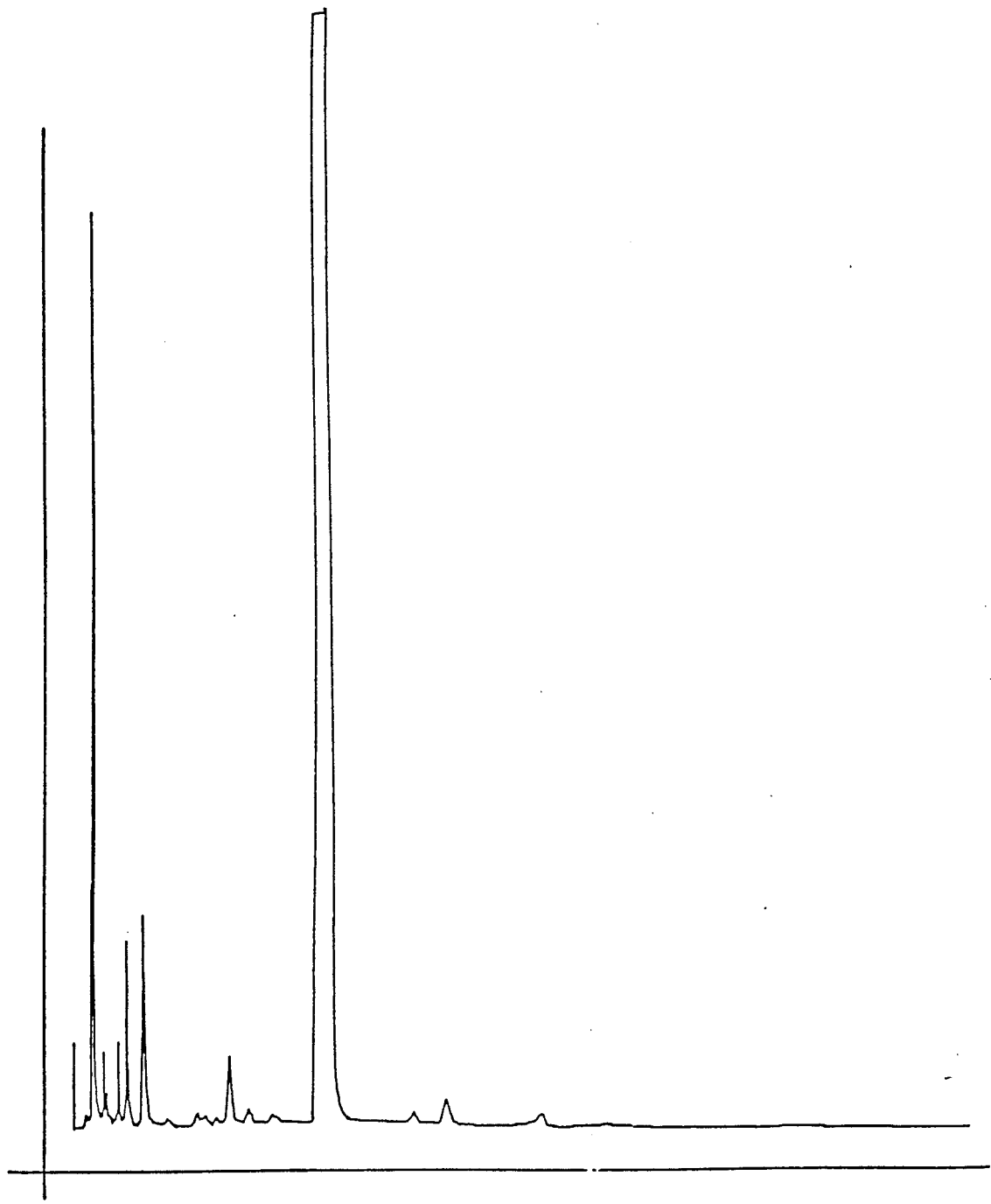
FIG. 47 is the GLC profile for the reaction product of Example A containing the compound having the structure.

FIG. 47 is the GLC profile for the crude reaction product of Example A containing the compound having the structure:

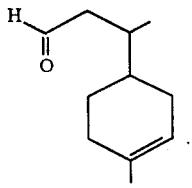

The peak indicated by reference numeral 5 is the peak for the compound having the structure:

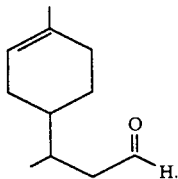

FIG. 1 is the GLC profile for the crude reaction product of Example A containing the compound having the structure:

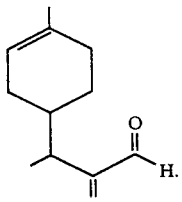

(Conditions: K-20M column programmed at 100°-220° C. at 8° C. per minute). The peak indicated by reference numeral 10 is the peak for the compound having the structure:

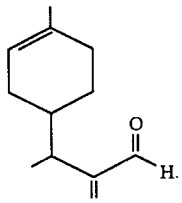

FIG. 2 is another GLC profile for the reaction product of Example I (Conditions: Carbowax column programmed at 130°-220° C.). The peak indicated by reference numeral 21 is the peak for the compound having the structure:

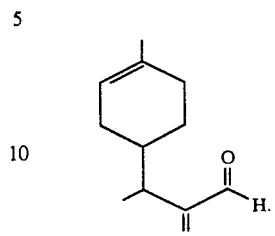

The peaks indicated by reference numerals 22 and 23 are for the compounds having the structures:

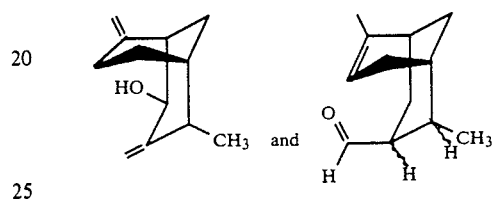

wherein these structures are representative of mixtures and in the mixture in each of the compounds one of the dashed lines is a carbon-carbon double bond and the other of the dashed lines is a carbon-carbon single bond.

FIG. 4 is the GLC profile for fraction 4 of the distillation product of the reaction product of Example II (Conditions: K-20M column programmed at 100°-220° C. at 8° C. per minute). The peak indicated by reference numeral 41 is the peak for the compound having the structure:

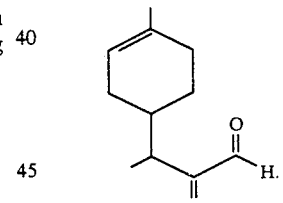

FIG. 5 is the GLC profile for the crude reaction product of Example III. The peak indicated by reference numeral 51 is the peak for the compound having the structure:

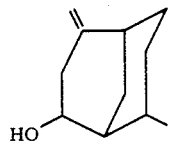

The peak indicated by reference numerals 52 and 53 are for the solvent used in the reaction mass. (Conditions: Carbowax column programmed at 130°-220° C. at 8° C. per minute).

FIG. 5A is the GLC profile for the crude reaction product of Example IIIA. The peak indicated by reference numeral 55 is the peak for the compound having the structure:

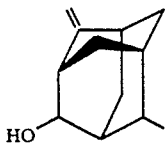

The peak indicated by reference numeral 54 is the peak for the mixture of compounds defined according to the structure:

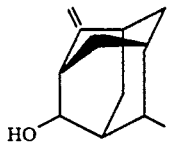

representative of a mixture of compounds wherein in the mixture in each of the compounds one of the dashed lines is a carbon-carbon double bond and the other of the dashed lines is a carbon-carbon single bond. The peak indicated by reference numeral 56 and 57 is for a mixture of compounds defined according to the structure:

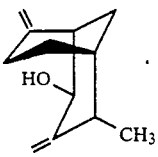

wherein in the mixture one of the dashed lines is a carbon-carbon double bond and the other of the dashed lines is a carbon-carbon single bond. (Conditions: Carbowax column programmed at 130°–220° C. per minute).

FIG. 8 is the GLC profile for the crude reaction product of Example V(A) (Conditions: Carbowax column programmed at 130°–220° C. at 8° C. per minute). The peak indicated by reference numeral 81 is the peak for the compound having the structure:

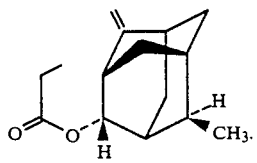

The peak indicated by reference numeral 82 is the peak for the compound having the structure:

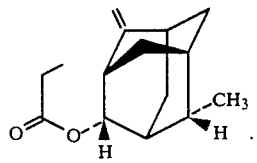

FIG. 16 is the GLC profile for the crude reaction product of Example VIII (Conditions: Carbowax column programmed at 130°–220° C. at 8° C. per minute).

The peak indicated by reference numeral 161 is for one of the isomers having the structure:

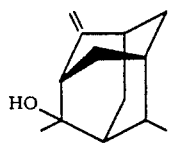

The peak indicated by reference numeral 162 is for another isomer having the structure:

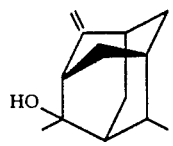

The peak indicated by reference numeral 163 is the peak for another isomer of the compound having the structure:

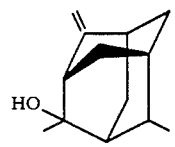

The peak indicated by reference numeral 164 is for isomers of the compound having the structure:

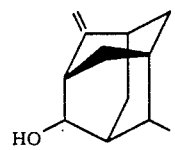

FIG. 22 is the GLC profile for the crude reaction product of Example X. The peak indicated by reference numeral 2200 is the peak for the compound having the structure:

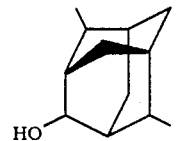

(Conditions: Carbowax column programmed at 130°–220° C. at 8° C. per minute).

Referring to FIGS. 26 and 27 in particular, the apparatus used in producing polymeric fragrances containing one or more of the adamantane derivatives comprises a device for forming scented polyolefin (for example) pellets, which comprises a vat or container 212 into which a mixture of polyolefins such as polyethylene and an aromatic substance or scented material is placed (in this case at least one of the adamantane derivatives of our invention). The container is closed by an airtight lid 228 and clampled to the container by bolts 265. A stirrer 273 traverses the lid or cover 228 in airtight manner and is rotated in a suitable manner. A surrounding cylinder 212 having heating coils 212A which are supplied with electric current through cable 224 from a rheostat or control 216 is operated to maintain a temperature inside the container 212 such that polyethylene or other thermoplastic polymer in the container will be maintained in the molten or liquid state. It has been found advantageous to employ a colorless odorless polymer (e.g., polyethylene) with viscosity ranging between 180 and 220 saybolt seconds and having a melting point in the range of 200°-280° F. The heater 212A is operated to maintain the upper portion of the container 212 within a temperature range of from 250°-350° F. The bottom portion of the container is heated by means of heating coils 212A heated through a control 220 connected thereto through a connecting wire 222 to maintain the lower portion of the container within a temperature range of from 250°-350° F.

Thus, polymer (e.g., polyethylene) is added to container 212 and is heated from 10-12 hours whereafter a scemted aroma imparting material (at least one of the adamantane derivatives of our invention) is added quickly to the melt. The material must be compatible with the polyolefin and forms a homogeneous liquid melt therewith. The scented material is of a type for the particular aroma desired and formulated specifically for the scenting purpose for which the polyolefin will be employed.

Generally about 5-30% by weight of the scented material (containing at least one of the adamantane derivatives of our invention) are added to the polyolefin.

After the scent imparting material (e.g., a composition containing one of the adamantane derivatives of our invention) is added to the container 212, the mixture is stirred for a few minutes, for example, 5-15 minutes and maintained within the temperature range as indicated previously by heating coils 212A. The controls 216 and 220 are connected, respectively, through cables 214 and 222, respectively, to heating coils 212A. The said cotnrols 216 and 220 are also connected through cables 224 and 226, respectively, to a suitable power supply of electric current for supplying the electric power to the heating coils 212A for heating purposes.

Thereafter the valve "V" is opened permitting the mass to flow outwardly through conduit 218/232 having a multiplicity of orifices 234 adjacent to the lower side therof. The outer end of the conduit 218/232 is closed so that the liquid polymer (e.g., polyolefin) and aroma imparting material (e.g., at least one of the adamantane derivatives of our invention) will continuously drop through orifices 234 downwardly from conduit 232. During this time the temperature of the polymer (e.g., polyethylene or polyolefin) and scent imparting material (e.g., at least one of the adamantane derivatives of our invention) is accurately controlled so that a temperature in the range of from about 2100°-275° F. will exist in the conduit 218/232. The regulation of the temperature through the controls 216 and 220 is essential in order to insure temperature balance to provide for the continuous dropping or dripping of molten polymer (e.g., polyethylene) and scenting material (e.g., one or more of the adamantane derivatives of our invention) mixture through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238 they form pellets 244 which harden almost instantaneously and fall off the end of the conveyor 238 into a container 245 and ultized in processes as illustrated, infra.

A feature of this aspect of the process of our invention is the provision for moistening of the conveyor belt 238 to insure rapid formation of the solid polymeric (e.g., polyolefin) scented pellets 244 without sticking to material which will not normally stick to a melted plastic. A moistening means 248 insures a sufficiently cold temperature of the belt surface for adequate formation of the pellets 244. The adequate moistening means comprises a container 250 which is continuously fed with water 254 to maintain a level for moistening a sponge element 256 which bears against the exterior of the belt 238.

FIG. 30 is the GLC profile for the crude reaction product of Example XIV ((Conditions: SE-30 column programmed at 130°-220° C. at 8° C. per minute).

The peak indicated by reference numeral 303 is the peak for the mixture of compounds defined according to the structure:

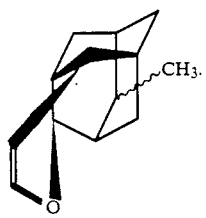

The peak indicated by reference numeral 304 is the peak for the compound having the structure:

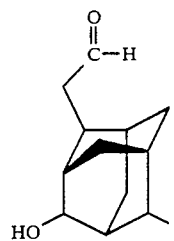

The peak indicated by reference numeral 305 is the peak for the mixture of compound having the structure:

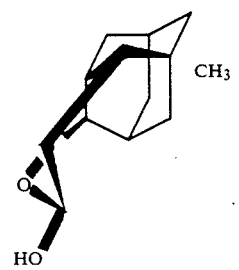

The peak indicated by reference numeral 301 is the peak for the methanol solvent. The peak indicated by reference numeral 302 is the peak for the toluene solvent. (Conditions: SE-30 column programmed at 130°-220° C.).

FIG. 37A is the GLC profile for the crude reaction product of Example XV (Conditions: Carbowax column programmed at 130°-220° C. at 8° C. per minute). The peak group indicated by reference numeral 370 is for the compound having the structure:

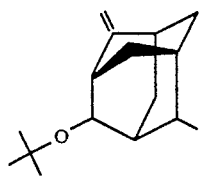

FIG. 37B is the GLC profile for distillation fraction 3 of the distillation product of the reaction product of Example XV. The peak group indicated by reference numeral 371 is for the compound having the structure:

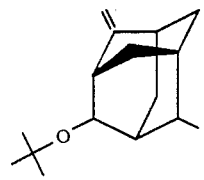

(Conditions: Carbowax column programmed at 130°-220° C. at 8° C. per minute).

FIG. 37C is the GLC profile for distillation fraction 3 of the distillation product of the reaction product of Example XV. The peak indicated by reference numeral 372 is the peak for the isomer or mixture of isomers of epimers having the structures:

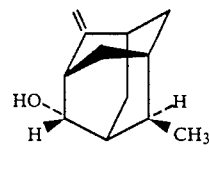

and/or

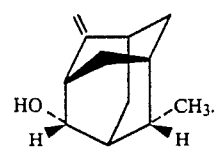

FIG. 39 is the GLC profile for distillation fraction 6 of the distillation product of the reaction product of Example XV. The peak indicated by reference numeral 395 is the peak for one or both of the epimers having the structures:

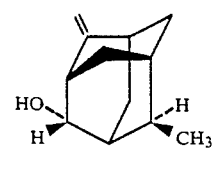

and/or

-continued

The peak indicated by reference numeral 394 is the peak for a starting material having the structure:

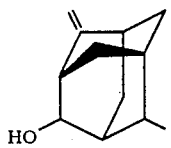

The peak indicated by reference numeral 393 is the peak for the compound having the structure:

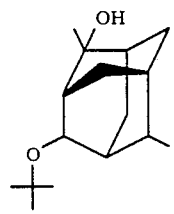

The peak indicated by reference numeral 392 is the peak for one or both of the compounds having the structures:

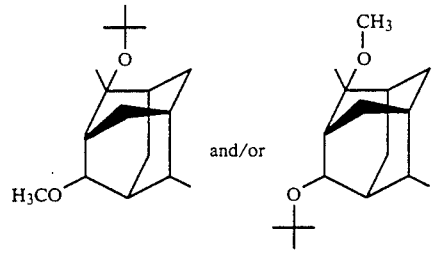

and/or

The peak indicated by reference numeral 391 is the peak for the compound having the structure:

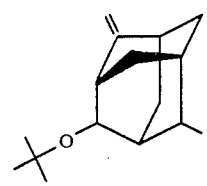

FIG. 45 is the GLC profile for the crude reaction product of Example XVI (Conditions: Carbowax column programmed at 130°-220° C. at 8° C. per minute). The peak indicated by reference numeral 450 is the peak for the compound having the structure:

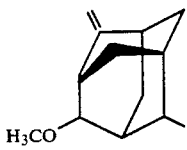

The peak indicated by reference numeral 451 is the peak for the compounds defined according to the structure:

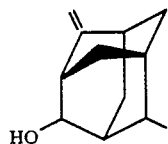

SUMMARY OF THE INVENTION

Our invention concerns adamantane derivatives defined according to the basic structure:

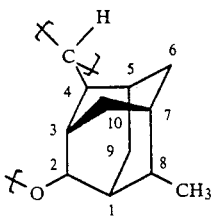

substituted at least at the "2", "4" and "8" positions, thusly:
(a) at the "2" position with a oxygen atom;
(b) at the "4" position with a carbon atom; and
(c) at the "8" position with a methyl group.

More specifically, our invention concerns adamantane derivatives defined according to the generic structure:

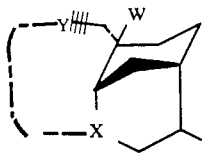

wherein X is a moiety selected from the group consisting of the structures:

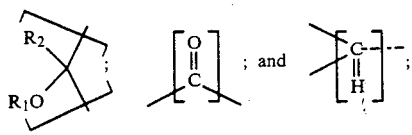

wherein Y is a moiety selected from the group consisting of the structures:

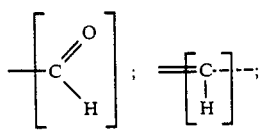

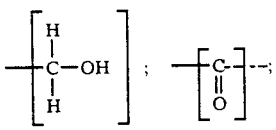

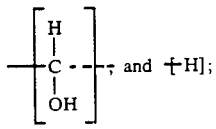

wherein W is no moiety or is selected from the group consisting of hydrogen, hydroxy and lower alkoxy; wherein the dashed line represented by:

is a carbon-carbon single bond or a carbon carbon double bond; wherein the dashed line represented by:

is no bond or is an ether moiety having the structure:

$-\!\!+\!O\!+\!\!-$;

wherein the line represented, thusly:

is a carbon-carbon single bond, a carbon-carbon double bond or a carbon-hydrogen single bond; wherein $R_1$ is selected from the group consisting of hydrogn, lower alkyl and lower acyl; and wherein $R_2$ is selected from the group consisting of hydrogen and lower alkyl; with the provisos that:
(1) when the dashed line:

---- is a carbon-carbon double bond then Y is hydrogen, the line

is a single bond; W is no moiety and X is selected from the group consisting of:

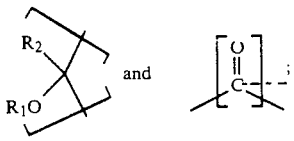

(2) when the dashed line:

---- is a carbon-carbon single bond and the line:

is a carbon-carbon single bond then either:
(1) Y is selected from the group consisting of:

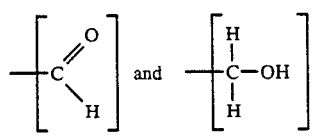

and X is selected from the group consisting of:

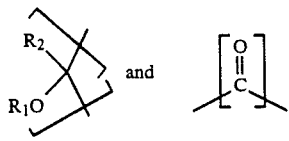

or
(2) the moiety:

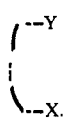

represents a moiety selected from the group consisting of an enol ether moiety having the structure:

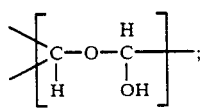

and a lactone moiety having the structure:

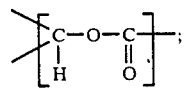

(3) when the line:

is a carbon-carbon double bond and the dashed line:

- - - - is a carbon-carbon single bond then the moiety:

is an ether moiety having the structure:

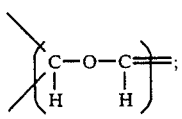

and
(4) when the dashed line:

- - - - is a carbon-carbon single bond and the line:

is a carbon-hydrogen bond and Y is:

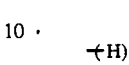

then W is selected from the group consisting of hydrogen, hydroxy and lower alkoxy;

and uses thereof in augmenting or enhancing the aroma or taste of consumable materials including perfume compositions, perfumed articles (e.g., solid or liquid anionic, cationic, nonionic or zwitterionic detergents, fabric softeners, fabric softener articles, cosmetic powders, hair preparations and perfumed polymers), colognes, smoking tobacco compositions, smoking tobacco articles, deodorizing articles and compositions and malodor maskants.

Our invention also relates to processes for preparing such adamantane derivatives using the terpene having the structure:

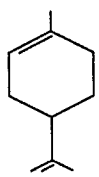

as a starting material and producing by means of "oxo" reaction the aldehyde having the structure:

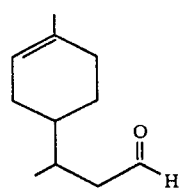

and producing therefrom the intermediate having the structure:

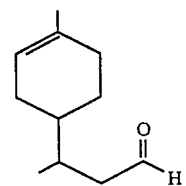

by means of reaction of the compound having the structure:

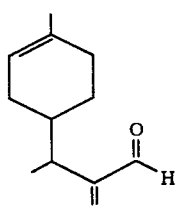

with formaldehyde via a "formylation" reaction as more specifically set forth in United Kingdom Pat. No. 2,054,557 published on Feb. 18, 1981 the specification of which is incorporated by reference herein.

The compound having the structure:

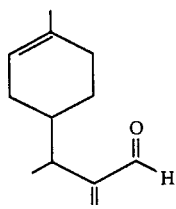

is further reacted by means of heating in the absence of acid and in the presence of a basic material such as sodium bicarbonate or an amine according to the reaction mechanism:

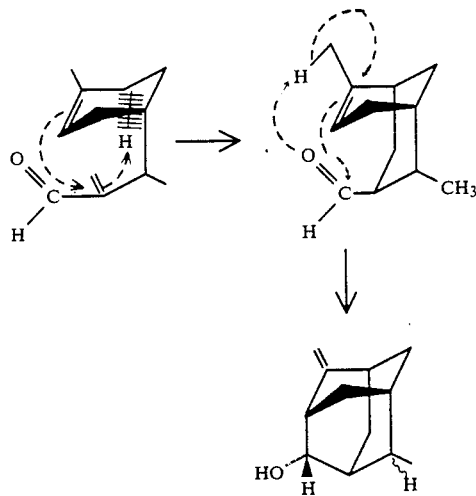

or according to the actual reaction:

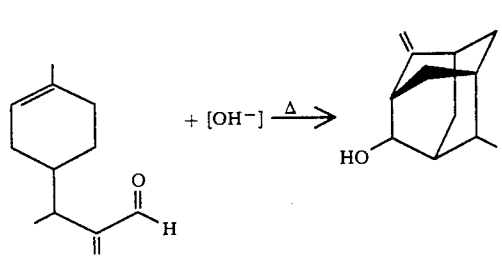

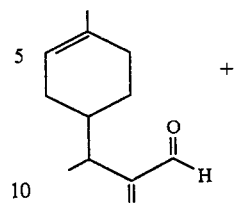

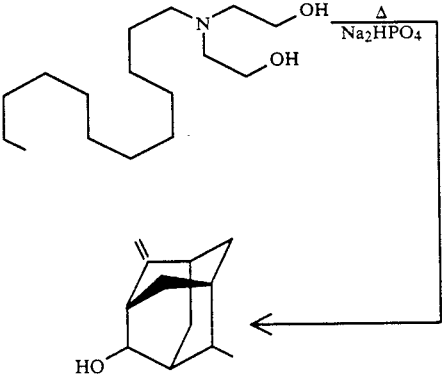

or more broadly:

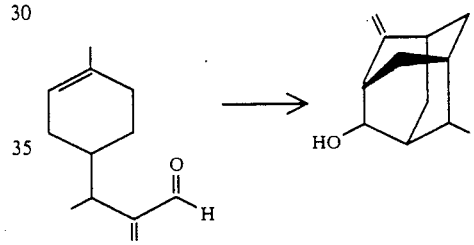

The reactions to prepare the compound having the structure:

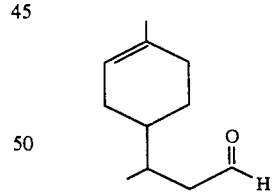

are as follows:

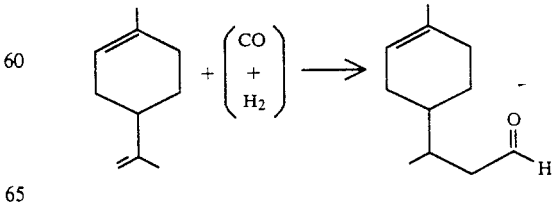

and

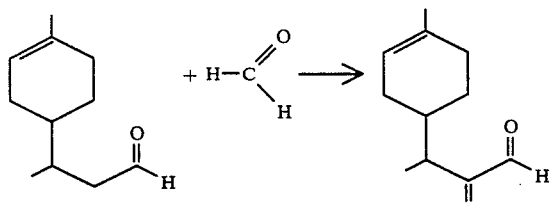

the resulting compounds defined according to the structure:

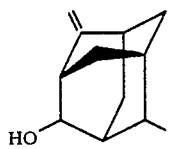

may then be further reacted to form a ketone by means of oxidation having the structure:

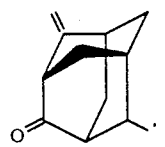

according to the reaction:

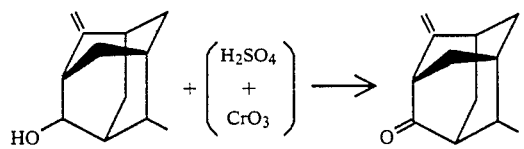

The resulting ketone may be used "as is" for its fragrance, deodorancy or tabacco flavorant properties or it may be reacted with hydrogen whereby the methylene group is reduced to a methyl group to form the saturated ketone having the structure:

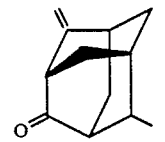

according to the reaction:

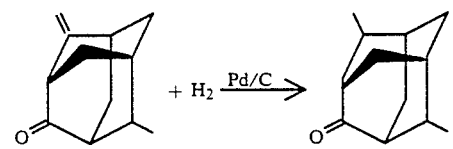

Either ketone may be used "as is" or may be further reacted with a grignard reagent or an alkyl lithium compound to produce tertiary alcohols according to the reaction:

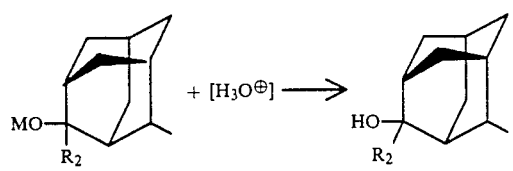

followed by the hydrolysis reaction:

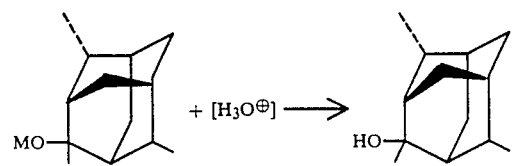

wherein the dashed line is a carbon-carbon double bond or a carbon-carbon single line; wherein M represents Li, MgBr, MgCl or MgI and where $R_2$ represents lower alkyl.

The resulting tertiary alcohol may be then further reacted with an acylating compound or with any etherifying compound according to the reaction:

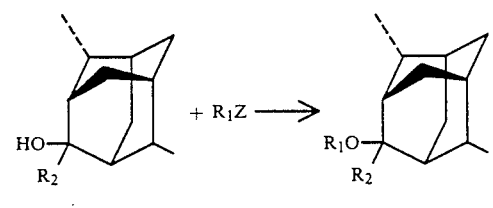

wherein $R_1$ is an acyl moiety or an alkoxy moiety and Z represents a halogen or sulfate moiety.

In the alternative, the compound having the structure:

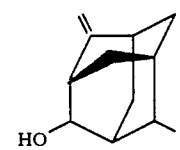

may be reacted via an "oxo" reaction with carbon monoxide and hydrogen at standard oxo reaction conditions to form a mixture of compounds according to the reaction:

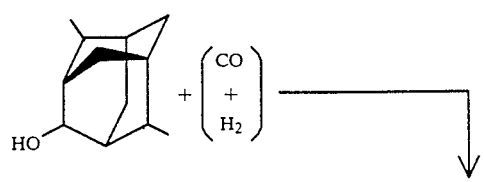

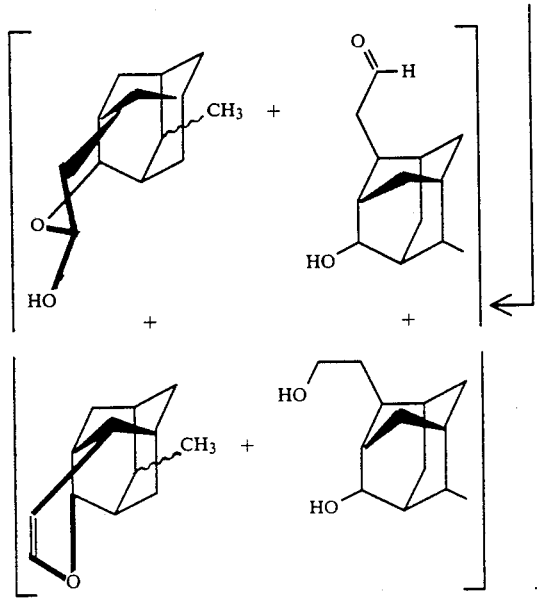

The resulting mixture may be separated by means of fractional distillation to form individual compounds, e.g., compounds having the structures:

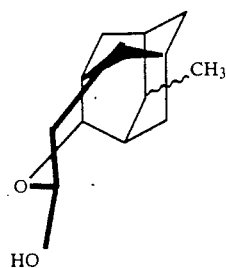

and

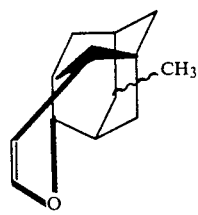

and

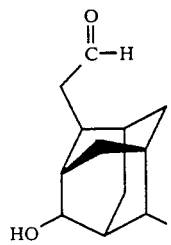

and

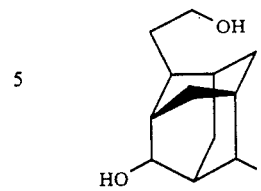

The compound having the structure:

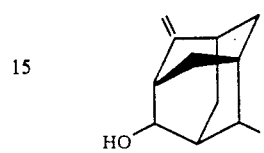

may, in the alternative, be etherified by means of etherification reactions such as by means of the reaction of the compound having the structure:

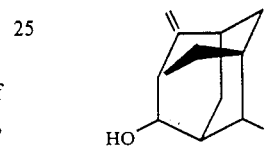

with dimethyl sulfate subsequent to reaction with base according to the reactions:

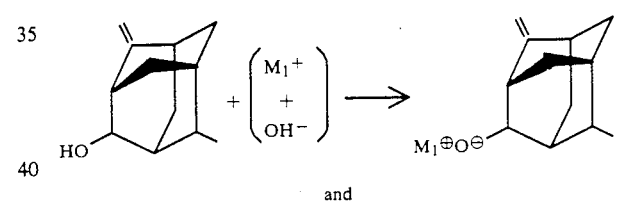

and

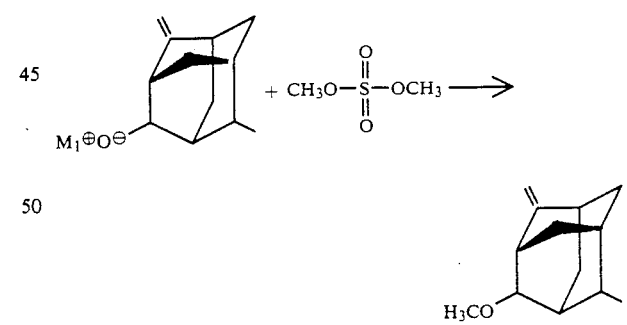

wherein $M_1$ represents alkali metal such as sodium, potassium or lithium. In the alternative, the etherification reactions which can be utilized involve the use of isobutylene and methyl tertiary butylether according to the reaction:

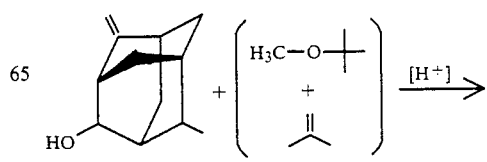

-continued

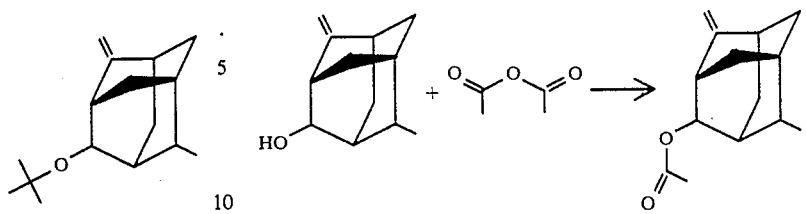

wherein byproducts are formed, that is, the compounds having the structures:

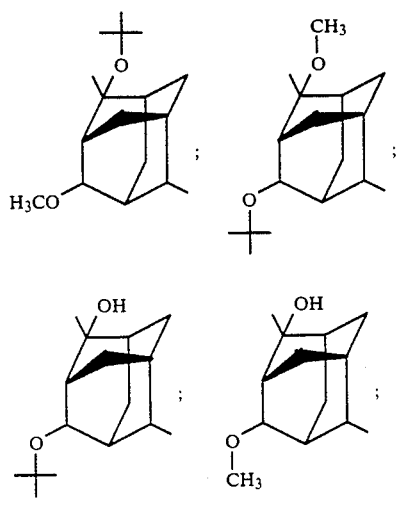

and

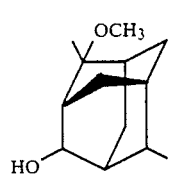

The compound having the structure:

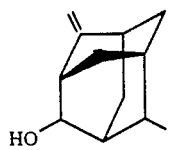

may also be acylated as with formic acid according to the reaction:

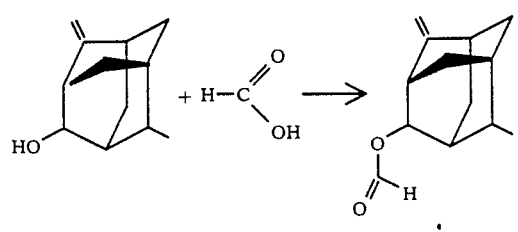

or acetic anhydride according to the reaction:

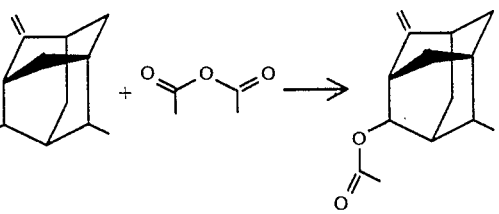

or the compound having the structure:

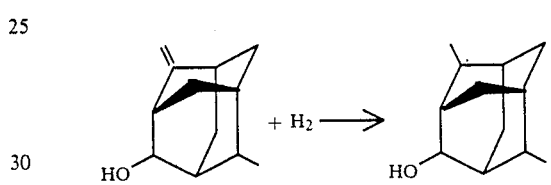

may be first hydrogenated according to the reaction:

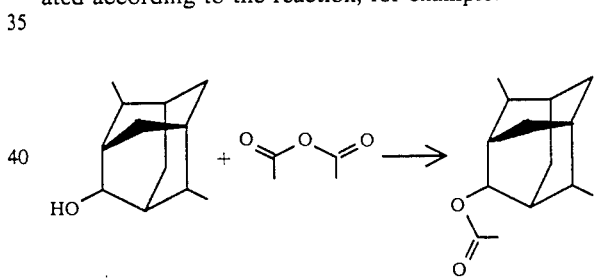

and that resulting hydrogenation product may be acylated according to the reaction, for example:

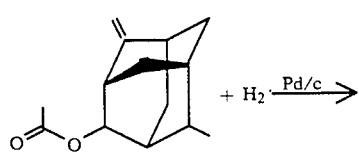

In the alternative, the acylation product may be hydrogenated according to the reaction:

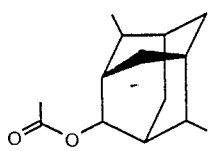

In general the hydrogenation reaction of the various adamantane derivatives having the methylene moiety are shown according to the reaction:

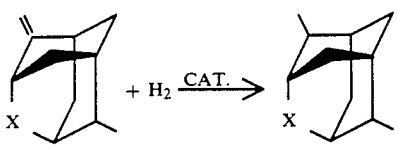

wherein X represents one of the moieties:

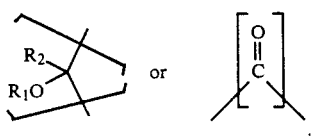

It is interesting to note that during the etherification reaction additional epimers of the compound having the structure:

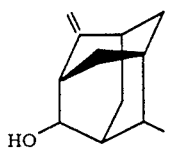

are formed, to wit, the compounds having the structures:

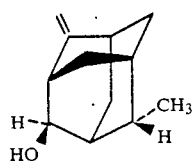

and

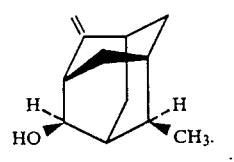

The adamantane derivatives of our invention have intense and substantive aromas which can be described as sandalwood, woody, patchouli, rhubarb, ginger, minty, amyris, camphoraceous, cardamon, earthy, cedarwood-like, vetiver, peppery, grapefruit peel-like, rose-like, ambery, spicy, ginger root, rosemary, piney, chrysanthemum-like, green and fir balsam pine-like, with sweet, amyris, camphoraceous, patchouli, woody, piney, cedarwood, sandalwood, herbaceous, incense, olibanum, vetiver, grapefruit peel-like, floral, sweet pea, rose, peony, fruit, early morning forest path, green, ginger root and amber topnotes. Table I below sets forth the summary of the particular compounds and their aromas:

TABLE I

| Composition of Matter | Perfumery Properties |
|---|---|
| The compound having the structure: <br><br> produced according to Example III, bulked fractions 6-9. | A sandalwood, woody, patchouli, rhubarb, ginger, minty and amyris aroma with amyris, camphoraceous, patchouli, woody, and piney topnotes. |
| The compound having the structure: <br><br> produced according to Example IIIA. | A camphoraceous, ginger cardamon and woody aroma profile. |
| The compound having the structure: <br><br> prepared according to Example IV, bulked fractions 8-18. | A cedarwood-like, sandalwood-like camphoraceous, woody, minty and earthy aroma with cedarwood, sandalwood, patchouli, camphoraceous, herbaceous, incense and olibanum topnotes. |
| The compound having the structure: <br><br> prepared according to Example V(B), bulked fractions 7-9. | A cedarwood-like, patchouli, vetiver, peppery, grapefruit peel-like and camphoraceous aroma with vetiver and grapefruit peel-like topnotes. |
| The compound having the structure: <br><br> prepared according to Example VI, bulked fractions 10-16. | A woody, rose-like and peony-like aroma with floral, sweet pea, rose and peony topnotes. |

TABLE I-continued

| Composition of Matter | Perfumery Properties |
|---|---|
| The compound having the structure: 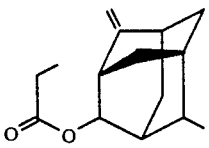 prepared according to Example VI, bulked fractions 5-19. | An ambery, woody and cedarwood-like aroma with fruity and woody topnotes. |
| The compound having the structure: 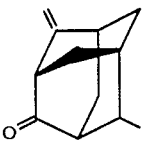 prepared according to Example VII. | A camphoraceous aroma with early morning forest path, green, piney, woody and camphoraceous topnotes. |
| The compound having the structure: 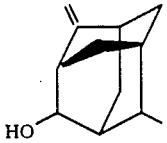 prepared according to Example X, bulked fractions 4 and 5. | A spicy, ginger root, rosemary and camphoraceous aroma with green, woody and ginger root topnotes. |
| The compound having the structure: 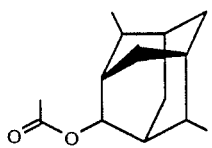 prepared according to Example XI, bulked fractions 5-9. | A woody, ambery, vetiver, cedarwood, piney and chrysanthemum-like aroma with woody, amber and olibanum topnotes. |
| The compound having the structure: 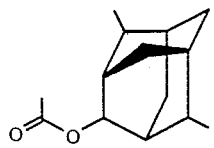 prepared according to Example XIII, bulked fractions 2-18. | A woody, amber, vetiver, cedarwood, piney and chrysanthemum-like aroma with woody, amber and olibanum topnotes. |
| The mixture of compounds having the structures: 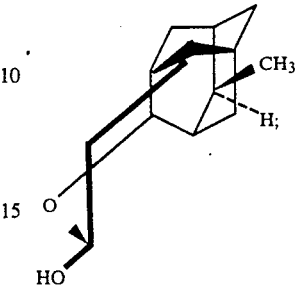 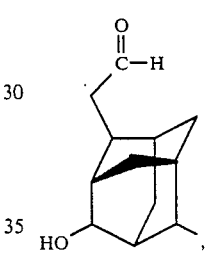 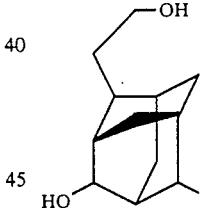 and 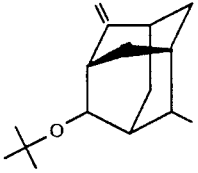 prepared according to Example XIV, fraction 6. | A green, woody and fir balsam-like aroma profile. |
| The mixture of compounds having the structures: 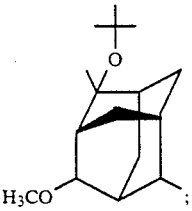 | A camphoraceous aroma with sweet camphoraceous topnotes. |

TABLE I-continued

| Composition of Matter | Perfumery Properties |
|---|---|
| (structure with CH3-O, O, and tert-butyl-O groups) prepared according to Example XV. | |
| (structure with OH and tert-butyl-O groups) | |
| (structure with OH and O-CH3 groups) and | |
| (structure with OCH3 and HO groups) | |
| The compound having the structure: (ketone structure) bulked fractions 4–6 produced according to Example XII. | A fresh, camphoraceous, sage-like and woody aroma profile with camphoraceous and woody topnotes. |
| The compound having the structure: (structure with H3CO) prepared according to Example XVI. | A natural, fresh pine, forest aroma profile. |

DETAILED DESCRIPTION OF THE INVENTION

In carrying the reaction:

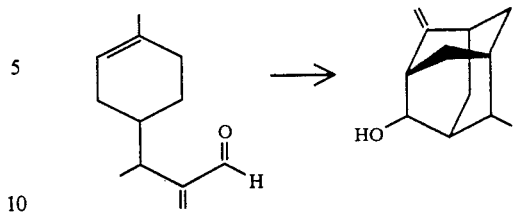

the reaction may take place in the presence of base; but must take place in the absence of acid. Accordingly, the reaction can be written:

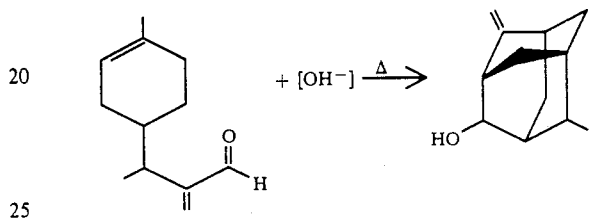

and can take place in the presence of sodium bicarbonate, sodium carbonate, potassium bicarbonate, potassium carbonate or disodium acid phosphate in the absence of solvent.

The temperature of reaction may be in the range of from about 130° C. up to about 250° C. with a preferred temperature of 210°–230° C. The reaction pressure may vary from about 0.5 up to about 10 atmospheres with a preferred reaction pressure of about 1 atmosphere. The reaction mechanism is shown, thusly:

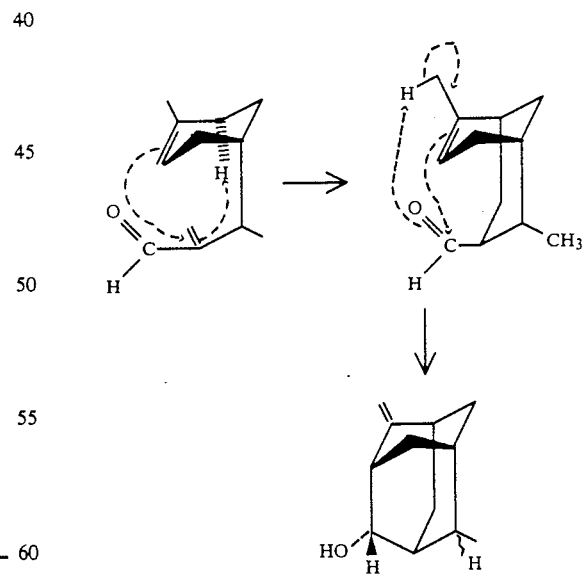

At the end of the reaction, the reaction product is distilled by means of fractional distillation (e.g., at a vapor temperature of 128°–133° C. and a pressure of 5–12 mm/Hg.).

The compound having the structure:

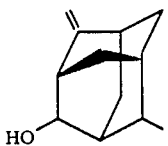

produced in this fashion is actually in the form of two isomers having the structures:

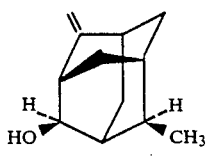

and

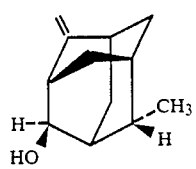

As will be shown, infra, the mixture of these two compounds is further empimerized to the compounds having the structures:

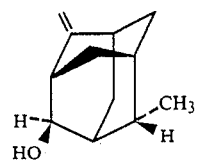

and/or

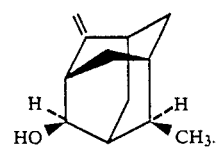

The resulting alcohols or epimers thereof can then, if desired, be further reacted with a reducing agent such as hydrogen whereby the methylene double bond is reduced according to the reaction:

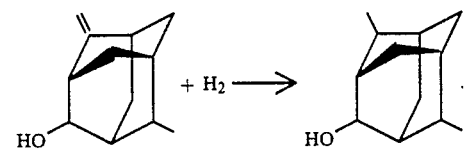

The reaction may be carried out in the presence of an inert solvent such as isopropyl alcohol but must be carried out in the presence of a hydrogenation catalyst, for example, Raney nickel or palladium suspended on carbon or palladium suspended on calcium carbonate, for example, 5% palladium on calcium carbonate. The reaction temperature may range from about 80° C. up to about 150° C. and the reaction pressure may range from about 80 psig up to about 150 psig. At the end of the reaction, the reaction mass is filtered, the solvent is evaporated and the reaction product is fractionally distilled.

The compound having the structure:

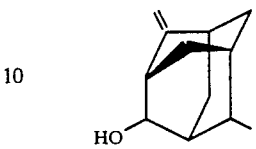

or the hydrogenated compound thus produced having the structure:

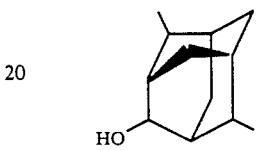

may be esterified, etherified or oxized.

The esterification reaction, to wit:

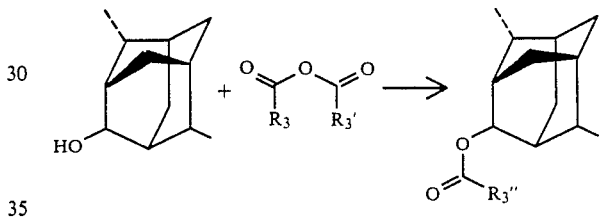

takes place wherein the dashed line represents a carbon-carbon single bond or a carbon-carbon double bond and $R_3$ are the same or different hydrogen or lower alkyl with the proviso that $R_3$ and $R_3'$ are not both hydrogen. In addition, the formate ester having the structure:

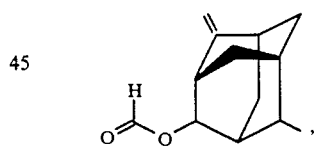

for example, can be produced by means of reaction of formic acid with acetic anhydride according to the reaction:

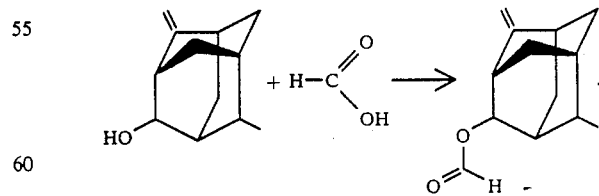

In fact, the reaction may take place at a temperature in the range of from about 10 up to about 40° C. in the presence of an acid catalyst such as a sulfuric acid catalyst or a hydrochloric acid. Other esterification reagents include acetic anhydride which reacts with the compound having the structure:

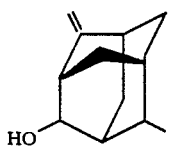

according to the reaction:

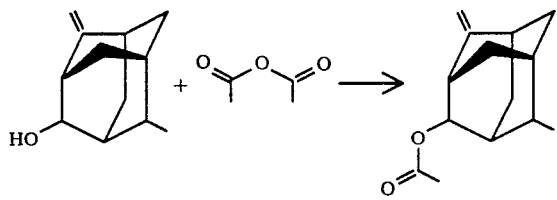

or propionic acid anhydride which reacts with the compound having the structure:

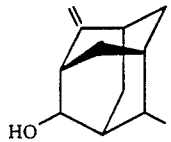

according to the reaction:

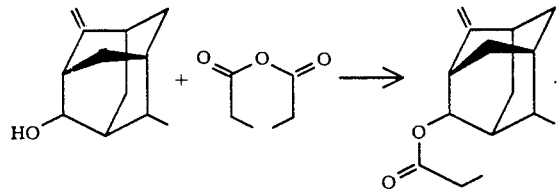

The oxidation reaction can be carried out to form a compound having the structure:

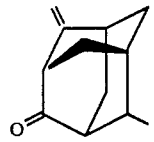

or it can be carried out to form a compound having the structure:

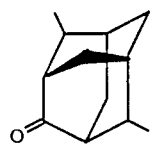

In carrying out the reaction:

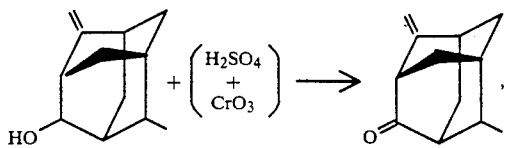

a temperature of from about 0° up to about 250° C. can be used. The reaction can be carried out in the presence of any chromic oxidizing agent, for example, "Collins" reagent which is chromium trioxide in methylene dichloride or it can be carried out in the presence of pyridinium dichromate or pyridinum chlorochromate at temperatures in the range of 0° to 40° C. The reaction can also be carried out in the presence of a copper chromite catalyst at a temperature in the range of 200°-220° C. The reaction may be carried from about 0.8 up to about 2 atmospheres with 1 atmosphere pressure being preferred.

The etherification reactions, to wit:

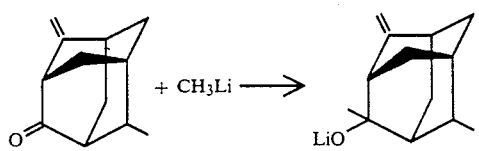

or the sequence:

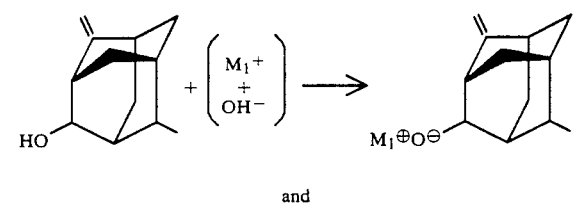

and

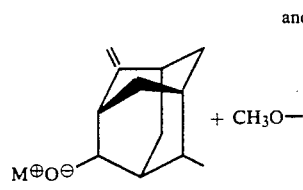

are carried out as follows:

With respect to the reaction:

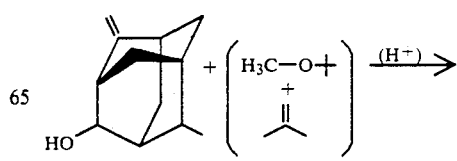

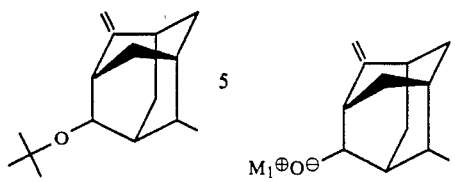

the reaction can be carried out in the presence of any mineral acid, e.g., hydrochloric acid, sulfuric acid or phosphoric acid. The reaction is carried out using isobutylene in admixture with methyl tertiary butylether with a mole ratio of isobutylene:methyl tertiary butylether ranging from about 0.5:1.5 up to about 1.5:0.5. The reaction temperature may vary from about 35° C. up to about 50° C. The reaction time may vary from about 5 hours up to about 15 hours. With this particular reaction, various byproducts are formed having the structures, to wit:

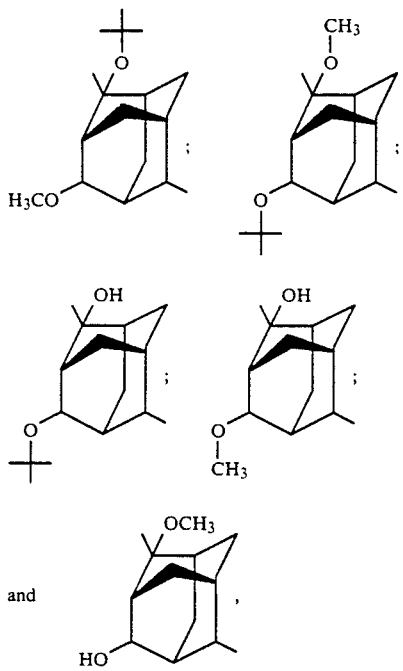

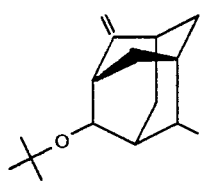

in addition to the compound having the structure:

With respect to the reaction sequence:

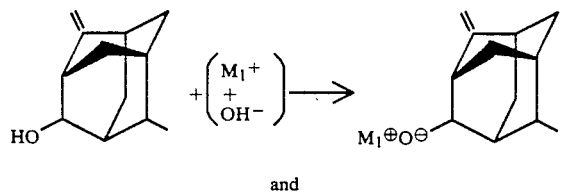

and

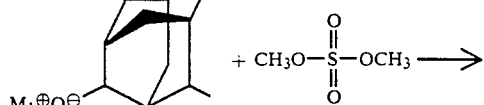

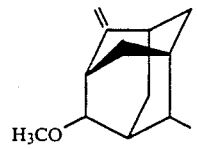

whereby the compound having the structure:

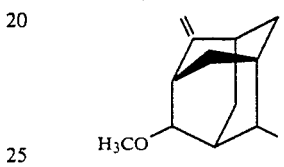

is formed, the first reaction, to wit:

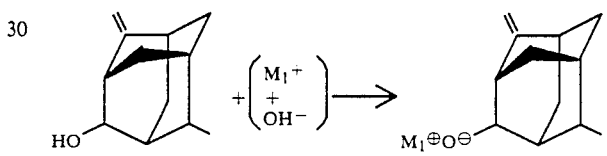

takes place in the presence of a strong base such as sodium hydroxide, lithium hydroxide or potassium hydroxide at a temperature in the range of from about 10° up to about 40° C. In the alternative however the reaction may take place using sodium hydride or sodium in place of the alkali metal hydroxide in order to form the compound having the structure:

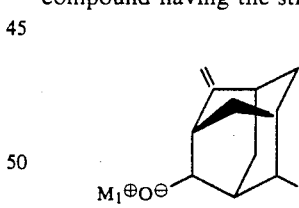

where $M_1$ is alkali metal. The resulting product having the structure:

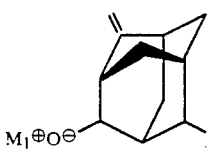

is then reacted with dimethyl sulphate at a temperature in the range of 40°–80° C. with a mole ratio of dimethyl sulphate:compound having the structure:

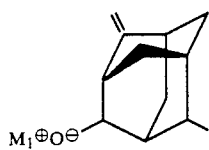

being from about 1:1 up to about 1.2:1 according to the reaction:

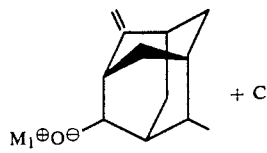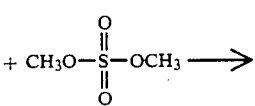

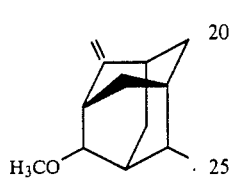

The resultant oxidized compounds, e.g., ketones, for example, the ketone having the structure:

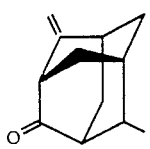

may be further reacted to form tertiary alcohols as with alkyl lithium and lower alkyl grignard reagents according to the reaction sequence:

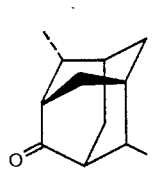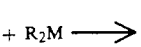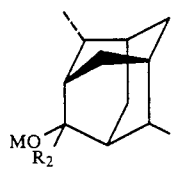

and

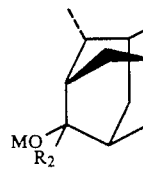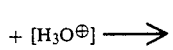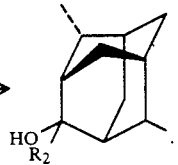

wherein the dashed line represents a carbon-carbon single bond or a carbon-carbon double bond; and wherein M represents Li, MgBr, MgCl or MgI and $R_2$ represents lower alkyl. In the alternative $R_2$ could also represent lower alkenyl or lower alkynyl, or aryl or aralkyl or alkaryl. The conditions of this reaction are as set forth in Hallden-Aberton, J.Org.Chem., Volume 46, No. 3, 1981, pages 538–546 the disclosure of which is incorporated herein by reference. Such conditions are also set forth in U.S. Pat. No. 4,439,354 at column 22, 23 and 24 the disclosure of which is incorporated herein by reference.

The resulting compound, for example, the compound having the structure:

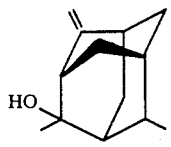

may be esterified according to the reaction, for example:

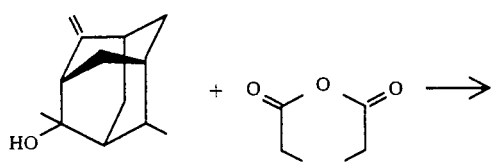

or, for example:

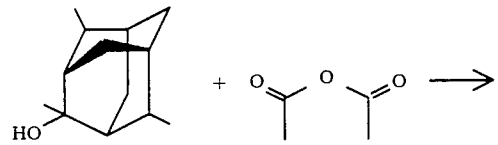

according to esterification conditions as set forth at column 21 of U.S. Letters Patent No. 4,439,345 the specification of which is incorporated herein by reference. In addition, the compound having the structure, for example:

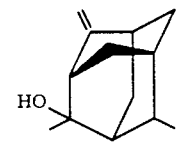

can be etherified forming, for example, the methylether by first reacting the compound with sodium and then reacting the resulting sodium organometallic compound with methyliodide in order to form the methylether.

The conditions of the etherification are set forth at columns 20 and 21 of U.S. Pat. No. 4,439,345 the specification of which is incorporated herein by reference.

The adamantane derivatives of our invention having an alkylidene substituent at the "4" position of the adamantane ring which is:

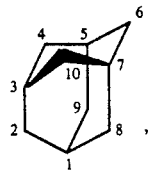

for example, the compound having the structure:

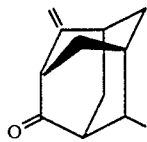

or the compound having the structure:

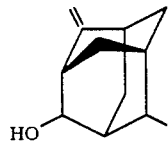

or the compound having the structure:

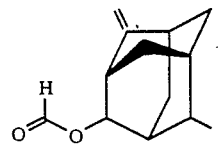

or the compound having the structure:

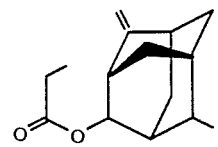

may be reacted via an "oxo" reaction shown, generically as follows:

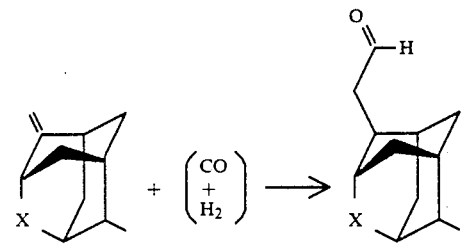

wherein x has the structure:

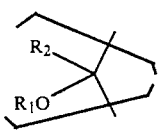

or

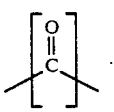

and wherein $R_1$ represents hydrogen, lower alkyl or lower acyl and wherein $R_2$ represents hydrogen or lower alkyl. Thus, for example, when the compound having the structure:

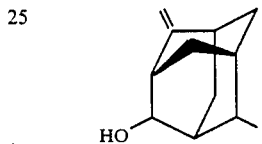

is reacted with carbon monoxide and hydrogen, the following reaction takes place:

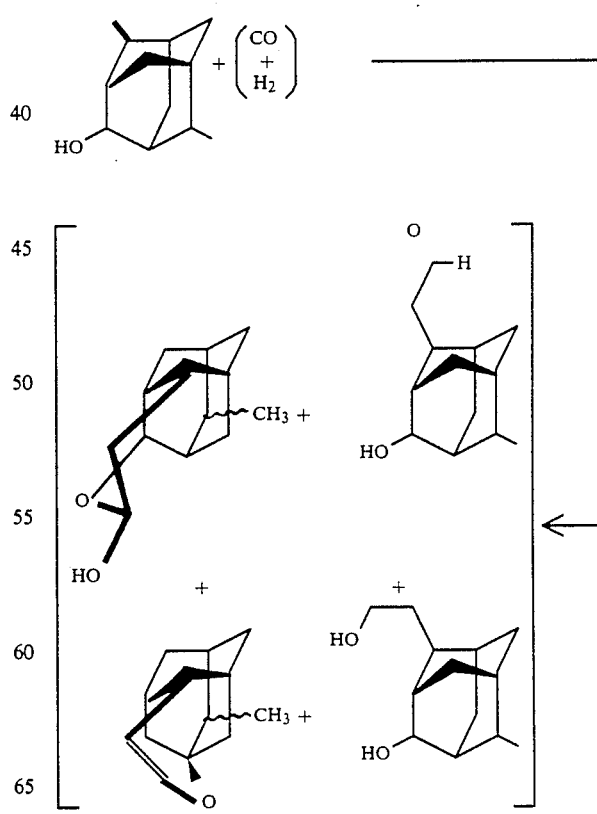

wherein compounds shown by the structures:

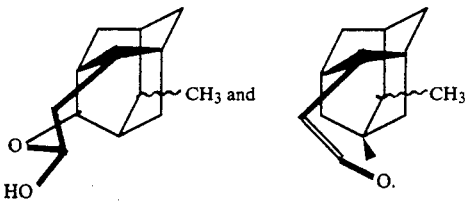

are indicative of one or more isomers each as indicated by the wavy line showing the methyl moiety bonded at the "9" position of the adamantane moiety. The reaction of the adamantane derivatives having the alkylidene substitution at the "4" position with carbon monoxide and hydrogen, the "oxo" reaction is carried out in the presence of a "oxo reaction catalyst" such as rhodium, $Co_2(CO)_8$, or organophosphorous polydentate ligand such as those described in European Published Application No. 33,554 published on Aug. 12, 1981, the specification of which is incorporated herein by reference. Examples of which are:

$\phi_2\text{-P}-(CH_2)_2-P\phi_2$, $\phi\text{-P}+(CH_2)_2-P\phi_2]_2$, $P+(CH_2)_2-P\phi_2]_3$, $\phi_2P-HC=CH-P\phi_2$, and $\phi\text{-P}-\underset{\underset{CH_3}{|}}{CH}-CH_2-P\phi_2$ at pressures of from about 3 atmospheres up to about 1,000 atmospheres and at temperatures in the range of from about 30° C. up to about 150° C. Preferably when using a rhodium catlayst, the temperature of reaction is between 70° and 110° C.; when using a $Co_2(CO)_8$ catalyst, the temperature is between 110° and 120° C.; and when using a ligand such as those exemplified in European Published Application No. 33,544, the specification of which is incorporated herein by reference, the temperature may vary from 95° C. up to 120° C. as is set forth in the following table:

TABLE A

| Ligand | Reaction Temperature |
| --- | --- |
| $\phi_2P(CH_2)_2P\phi_2$ | 95–120° C. |
| $\phi P\begin{cases}CH_2-CH_2-P\phi_2\\CH_2-CH_2-P\phi_2\end{cases}$ | 120° C. |
| $P\begin{cases}CH_2-CH_2-P\phi_2\\CH_2-CH_2-P\phi_2\\CH_2-CH_2-P\phi_2\end{cases}$ | 120° C. |
| $\phi_2P-CH=CH-P\phi_2$ | 120° C. |
| $\phi_2P-\underset{\underset{CH_3}{|}}{CH}-CH_2-P\phi_2$ | 95° C. |
| $\phi_2P(CH_2)_4P\phi_2$ | 95° C. |
| $\phi_2P(CH_2)_3P\phi_2$ | 95° C. |
| $P\phi_3$ | 120° C. |
| $\phi_2P(CH_2)_{10}P\phi_2$ | 120° C. |
| $\phi_2PCH_2P\phi_2$ | 120° C. |
| $(CH_3)_2P(CH_2)_2P(CH_3)_2$ | 120° C. |

The resulting reaction product is then separated as by fractional distillation thereby yielding a mixtures of compounds including, but not limited to aldehydes.

The resulting mixtures and/or compounds (if further separated as by preparative GLC) may be used "as is" for their organoleptic properties or they may be further reacted by oxidation or reduction techniques, e.g., as by hydrogenation using a hydrogenation catalyst or by oxidation using a chromium oxidation catalyst. Furthermore, the aldehyde-containing compositions may be further reacted as by reduction with an alkali metal or alkali metal hydride such as sodium borohydride, lithium aluminum hydride and the like. When a reaction takes place using a reducing agent such as sodium borohydride or lithium aluminum hydride, the mole ratio of aldehyde:alkali metal hydride is in the range of from about 1:1 up to about 4:1 with a preferred mole ratio of aldehyde:alkali metal hydride being about 3:1. The reaction takes place at reflux conditions in a solvent which will permit reflux conditions at atmospheric pressure. The reaction takes place in the presence of an inert solvent, that is, a solvent inert to the reactants and the reaction product and one which will permit a reflux temperature at atmospheric pressure in the range of from about 80° C. up to about 100° C. A preferred solvent is isopropyl alcohol. The concentration of aldehyde in the reaction mass may vary from about 5 moles per liter up to about 15 moles per liter with a concentration of aldehyde in the reaction mass (initially) being about 10 moles per liter. The concentration of alkali metal hydride in the reaction mass may very from about 2 moles per liter up to about 6 moles per liter with a preferred concentration of alkali metal hydride in the reaction mass being about 4 moles per liter.

The adamantane derivatives of our invention can be used to contribute powerful, long-lasting, sandalwood, woody, patchouli, rhubarb, ginger, minty, amyris, camphoraceous, cardamon, earthy, cedarwood-like, vetiver, peppery, grapefruit peel-like, rose-like, ambery, spicy, ginger root, rosemary, piney, chrysanthemumlike, green and fir balsam pine-like aromas, with sweet, amyris, camphoraceous, patchouli, woody, piney, cedarwood, sandalwood, herbaceous, incense, olibanum, vetiver, grapefruit peel-like, floral, sweet pea, rose, peony, fruity, early morning forest path, green, ginger root and amber topnotes to perfume compositions, perfumed articles, colognes, deodorizing articles, deodorizing compositions and malodor maskants. Examples of perfumed articles are anionic, cationic, nonionic and zwitterionic detergents, drier-added fabric softener compositions and drier-added fabric softener articles as well as hair preparations. As olfactory agents, the adamantane derivatives of our invention can be formulated into or used as components of a "perfume composition" or can be used as components of a "perfumed article" or the perfume composition may be added to perfumed articles.

The term "perfume composition" is used herein to mean a mixture of organic compounds including, for example, alcohols (other than the hydroxy-substituted adamantane derivatives of our invention); aldehydes (other than the oxo reaction products of our invention); ketones, (other than the keto-substituted adamantane derivatives of our invention), nitriles, ethers (other than the alkoxy-substituted adamantane derivatives of our invention), lactones, natural essential oils, synthetic essential oils, synthetic essential oils and frequently hydrocarbons which are admixed so that the combined odors of the individual components produce a pleasant or desired fragrance. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaportation; and (d) topnotes which are usually low boiling, fresh smelling materials.

In perfume compositions, the individual component will contribute its particular olfactory characteristics, but the overall effect of the perfume composition will be the sum of the effects of each of the ingredients. Thus, the individual adamantane derivatives of this invention or mixtures thereof can be used to alter the aroma characteristics of a perfume composition, for example, by highlighting or moderating the olfactory reaction contributed by another ingredient in the composition.

The amount of the adamantane derivative(s) of this invention which will be effective in perfume compositions, depends on many factors including the other ingredients, their amounts, and the effects which are desired. It has been found that perfume compositions containing as little as 0.5% of one or more of the adamantane derivatives of our invention or even less can be used to impart interesting sandalwood, woody, patchouli, rhubarb, ginger, minty, amyris, camphoraceous, cardamon, earthy, cedarwood-like, vetiver, peppery, grapefruit peel-like, rose-like, ambery, spicy, ginger root, rosemary, piney, chrysanthemum-like, green and fir balsam pine-like aromas, with sweet, amyris, camphoraceous, patchouli, woody, piney, cedarwood, sandalwood, herbaceous, incense, olibanum, vetiver, grapefruit peel-like, floral, sweet pea, rose, peony, fruit, early morning forest path, green, ginger root and amber topnotes to soaps, liquid and solid anionic, cationic, nonionic and zwitterionic detergents, cosmetic powders, liquid and solid fabric softeners, optical brightener compositions, perfumed polymers and other products. The amount employed can range up to 50% or higher and will depend on considerations of cost, nature of the end product and the effect desired on the finished product and the particular fragrance sought.

The adamantane derivatives of this invention can be used alone or a perfume composition as an olfactory component in detergents and soaps, space odorants and deodorants; colognes, toilet waters, bath salts, hair preparations, such as lacquers, brilliantines, pomades and shampoos; cosmetic preparations such as creams, deodorants, hand lotions and sun screens; powders such as talcs, dusting powders, face powders and the like. When used as an olfactory component of a perfumed article, as little as 0.01% of one or more of the adamantane derivatives of our invention will suffice to impart interesting, long-lasting, sharp, sandalwood, woody, patchouli, rhubarb, ginger, minty, amyris, camphoraceous, cardamon, earthy, cedarwood-like, vetiver, peppery, grapefruit peel-like, rose-like, ambery, spicy, ginger root, rosemary, piney, chrysanthemum-like, green and fir balsam pine-like aromas, with sweet, amyris, camphoraceous, patchouli, woody, piney, cedarwood, sandalwood, herbaceous, incense, olibanum, vetiver, grapefruit peel-like, floral, sweet pea, rose, peony, fruit, early morning forest path, green, ginger root and amber topnotes. Generally, no more than 0.5% is required.

In addition, the perfume composition can contain a vehicle or carrier for the adamantane derivative(s) taken alone or taken together with other ingredients. The vehicle can be a liquid such as an alcohol such as ethanol, a glycol such as propylene glycol or the like. The carrier can be an absorbent solid such as gum, (e.g., gum arabic, guar gum and xanthan gum) or components for encapsulating the composition such as gelatin which can be used to form a capsule wall surrounding the perfume oil as by means of coacervation.

An additional aspect of our invention provides an organoleptically improved smoking tobacco product and additives therefor including methods of making the same which overcome problems heretofore encountered in the creation or enhancement of specific desired sweet, oriental notes. Such notes both prior to and on smoking in both the main stream and the side stream, may now be readily controlled and maintained at the desired uniform level regardless of variations in the tobacco components of the blend; or the nature of the filter used in conjunction with the smoking tobacco article.

This invention further provides improved tobacco additives for materials used in the fabrication of tobacco articles (particularly smoking tobacco articles) and methods whereby desirable sweet, oriental notes may be imparted to smoking tobacco products and may be readily varied and controlled to produce the desired uniform flavoring characteristics.

In carrying out this aspect of our invention, we add to smoking tobacco materials or a suitable substitute therefor (e.g., dried lettuce leaves) an aroma and flavor additive containing as an active ingredient(s), one or more of the adamantane derivatives of our invention.

In addition to the adamantane derivatives of our invention, other flavoring and aroma additives may be added to the smoking tobacco material or substitute therefor either separately or in admixture with one or more adamantane derivatives of our invention:

I.

SYNTHETIC MATERIALS

Beta-methylcinnamaldehyde;
Eugenol;
Dipentene;
Damascenone;
Maltol;
Ethyl maltol;
Delta-undecalactone;
Delta-decalactone;
Benzaldehyde;
Amyl acetate;
Ethyl butyrate;
Ethyl valerate;
Ethyl acetate;
2-Hexen-1-ol;
2-Methyl-5-isopropyl-1-3-nonadiene-8-one;
2-Methyl-5-isopropylacetophenone;
2-Hydroxy-2,5,5,8a-tetramethyl-1-(2-hydroxyethyl)-decahydronaphthalene;
Dodecahydro-3a,6,69a-tetramethylnaptho(2,1-B)-furan;4-Judrpxujexempoc acid, gamma-lactone;
Polyisoprenoid hydrocarbons defined in Example V of U.S. Pat. No. 3,589,372 issued on June 29, 1971.

II.
NATURAL OILS

Celery seed oil;
Coffee extract;
Bergamot oil;
Nutmeg oil; and
Origanum oil.

An aroma and flavoring concentrate containing one or more of the adamantane derivatives of our invention and, if desired, one or more of the above-indicated additional flavoring additives may be added to the smoking tobacco material, to the filter or to the leaf or paper wrapper or to a filter which is part of the smoking article. The smoking tobacco material may be shredded, cured, cased or blended tobacco material or reconstituted tobacco material or tobacco substitutes (e.g., lettuce leaves) or mixtures thereof. The proportions of flavoring additives may be varied in accordance with taste, but insofar as enhancement or the imparting of sweet, oriental, "Turkish" like notes prior to and on smoking, in both the main stream and the side stream, we have found that satisfactory results are obtained if the proportion by weight of the sum total of adamantane derivatives to smoking tobacco material is between 50 ppm and 1500 ppm (0.005%–0.15%) of the active ingredients to the smoking tobacco material. We have further found that satisfactory results are obtained if the proportions by weight of the sum total of adamantane derivatives used to flavoring material is between 0.05:1 and 0.50:1.

Any convenient method for incorporating the adamantane derivatives in the tobacco product may be employed. Thus, the adamantane derivatives taken alone or along with other flavoring additives may be dissolved in a suitable solvent such as a food grade ethanol, pentane, diethyl ether and/or other volatile organic solvents, and the resulting solution may either be sprayed on a cured, cased and blended blended tobacco material; or the tobacco material or filter may be dipped into such solution. Under certain circumstances a solution of one or more of the adamantane derivatives of our invention taken alone or taken further together with other flavoring additives are set forth, supra, may be applied by means of a suitable applicator such as a brush or roller on the paper or leaf wrapper for the smoking product, or it may be applied to the filter by either spraying or dipping or coating.

Furthermore, it will be apparent that only a portion of the tobacco or substitute therefor need be treated, and the thus-treated tobacco may be blended with other tobaccos before the ultimate tobacco product is formed. In such cases, the tobacco treated may have one or more of the adamantane derivatives of our invention in excess if the amounts of concentrations above indicated so that when blended with other tobaccos, the final product will have the percentage within the indicated range.

While our invention is particularly useful in the manufacture of smoking tobacco such as cigarette tobacco, cigar tobacco and pipe tobacco, other tobacco products formed from sheeted tobacco dust or fines may also be used. As stated, supra, one or more of the adamantane derivatives of our invention can be incorporated with materials such as filter tip materials, seam paste, packaging materials and the like which are used along with the tobacco to form a product adpated for smoking. Furthermore, the adamantane derivatives of our invention can be added to certain tobacco substitutes of natural or synthetic origin (e.g., dried lettuce leaves) and, accordingly, by the term "tobacco" as used throughout this specification is meant any composition intended for human consumption, by smoking or otherwise, whether composed of toacco plant parts or substitued materials or both.

It will thus be apparent that the adamantane derivatives of our invention can be utilized to alter, modify, augment or enhance sensory properties, particularly organoleptic properties, such as flavor(s) and/or frangrance(s) of a wide variety of consumable materials.

In accordance with one specific example of our invention, an aged, cured and shredded domestic burley tobacco is sprayed with a 20% alcohol solution of the compound having the structure:

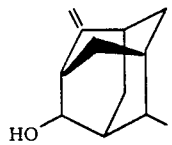

in an amount to provide a tobacco composition containing 800 ppm by weight of the compound having the structure:

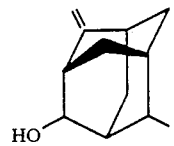

on a dry basis. Thereafter the alcohol is removed by evaporation and the tobacco is manufactured into cigarettes by the usual techniques. The cigarette, when treated as indicated has a desired and pleasant aroma which is detectable in the main stream and in the side stream when the cigarette is smoked. The aroma as described as being oriental, natural Turkish tobacco-like with pleasant and long-lasting cigar box-like nuances.

Our invention also relates to the utilization of controlled release technolgy for the controlled release of perfumes into gaseous environments; odor maskants and deodorizing agents into gaseous environments; and tobacco aromatizing and flavors into smoking article filters from polymers such as mixtures of epsilon polycaprolactone polymers and polyethylene which poly epsilon caprolactone polymers are defined according to at least one of the structures:

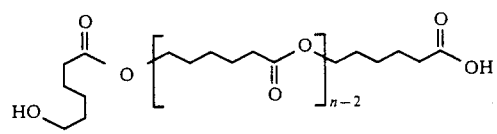

and/or

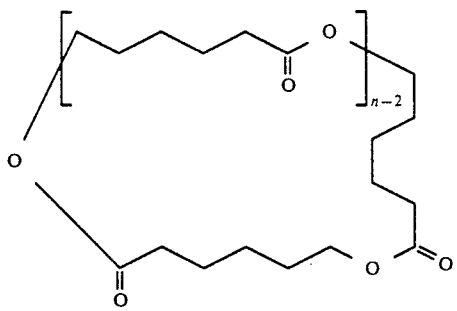

wherein "n" is from about 50 up to about 1,200 with the proviso that the average "n" n the system varies from about 150 up to about 700 according to the mathematical statement:

$$[700 \geq n \geq 150]$$

with the term n being the average number of repeating monomeric units for the epsilon polycaprolactone polymer. The perfumed or flavored material's release rate from such polymer mixture is close to "zero order". As a general rule, the release rate in a polymeric matrix is proportional to $t^{-\frac{1}{2}}$ until about 60% of the functional fluid (e.g., the adamantane derivative of our invention) is released from the polymeric matrix. The release rate thereafter is related exponentially to time as a general rule according to the equation:

$$\frac{dM_t}{dt} = k_1 e^{-k_2 t}$$

wherein $k_1$ and $k_2$ are constants. According to Kydonieus, "Controlled Release Technologies: Methods, Theory, and Applications", the amount of perfume composition released is proportional to time as long as the concentration of perfume or flavor material present, e.g., the adamantane derivatives of our invention is higher than the solubility of the agent in the matrix. Thus, such dispersed systems are similar to the dissolved systems except that instead of a decreased release rate after 60% of the perfume or flavor material has been emitted, the relationship holds almost over the complete release curve. Kydonieus further states, that if one assumes that the release of functional fluid by diffusion is negligible in monolithic erodible systems, the speed of erosion will control the release rate and release by erosion by a surface-area-dependent phenomenon, the release is constant (zero order) as long as the surface area does not change during the erosion process. This is the case with the polymers containing the adamantane derivatives of our invention.

The polyepsilon caprolactone polymers useful in practicing our invention are more specifically described in the brochure of the Union Carbide Corporation, 270 Park Avenue, New York, N.Y. 10017, entitled "NEW POLYCAPROLACTONE THERMOPLASTIC POLYMERS PCL-300 AND PCL-700" (incorporated herein by reference) the polyepsilon caprolactone polymers are composed of a repeating sequence of non-polar methylene groups and relatively polar ester groups. The average number of repeating monomeric units varies between 150 and 700 depending on the particular "PCL" number. Thus, regarding PCL-300 the average number of repeating monomeric units is about 300.

Regarding PCL-700, the average number of repeating monomeric units is 700.

The polyepsilon caprolactone homopolymers which are ultimately taken in admixture with such materials as polyethylene useful in the practice of our invention may also be stabilized using stabilizers as defined in U.S. Pat. No. 4,360,682 issued on Nov. 23, 1982, the specification of which is incorporated herein by reference. The stabilizing materials which stabilize the polyepsilon caprolactone useful in conjunction with our invention against discoloration are dihydroxybenzenes such as hydroquinone or compounds having the formula:

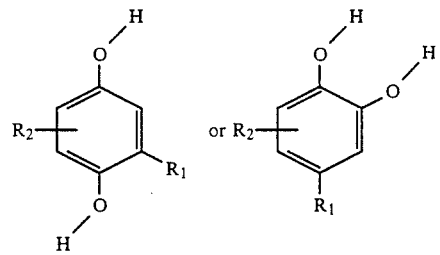

in which $R_1$ is alkyl of from 1 to 8 carbon atoms, and $R_2$ is hydrogen or alkyl of 1 to 8 carbon atoms. It is preferable to have such stabilizer in the polyepsilon caprolactone homopolymer in an amount of from about 100 to 500 ppm. Such stabilizers do not interfer with the functional fluids dissolved and/or adsorbed into the polymeric matrix.

The method of incorporating the adamantane derivatives of our invention or perfume compositions containing same into the polymers may be according to the technique of U.S. Pat. No. 3,505,432 issued on Apr. 7, 1970 (the specification for which is incorporated herein by reference) or U.S. Pat. No. 4,274,498 issued on Jan. 27, 1981, the disclosure of which is incorporated by reference herein.

Thus, for example, a first amount of liquid polyethylene-polyepsilon caprolactone plymer mixture (50:50) is mixed with one or more of the adamantane derivatives of our invention. Drops are formed from the mixture and the drops are solidified. The solidified drops are then melted, if desired, with a second amount of unscented low density polyethylene, for example, or polypropylene, for example. Usually, but not necessarily, the second amount of polymer is larger than the first amount. The resulting mixture thus obtained is solidified subsequent to or prior to ultimate casting into a utilitarian shape.

Thus, in accordance with one aspect of our invention the imparting of scent is effected in two stages. In a first stage, a 50:50 (weight:weight) polyepsilon caprolactone, e.g., PCL-700: polyethylene in molten form is admixed with a high percentage of one or more of the adamantane derivatives of our invention, e.g., the compound having the structure:

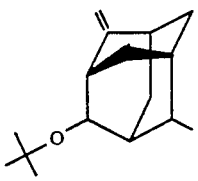

and the mixture is solidified in the form of pellets or beads. These pellets or beads thus contain a high percentage of adamantanes (e.g., up to 45% by weight of the entire mixture) and may be used as "master pellets" which thereafter, in a second stage, if desired, may be admixed and liquified with additional polymers such as additional polyethylene or mixtures of polyethylene and polyepsilon caprolactone in an unscented state, or unscented polypropylene. In addition, additional polymers or copolymers may be used, for example, copolymers specified and described in United Kingdom patent specification No. 1,589,201 published on May 7, 1981, the specification for which is incorporated by reference herein.

In accordance with the present invention at least one of the adamantane derivatives of our invention is added to the polymer in a large closed contaier or drum which is maintained under controlled temperature conditions while the polymer in a melted condition is mixed with at least one of the adamantane derivatives under agitation.

In order that the perfume or flavor be added uniformly to the polymer, the temperature of the melt is constantly controlled during the process. The polymer-perfume mixture is then directed through an enlongated conduit or pipe element having a plurality of orifices adjacent to the lower most portion thereof. The polymer enriched by at least one of the adamantane derivatives of our invention is permitted to drip through the orifices onto a continuously moving, cooled conveyor upon which the polymer containing at least one of the adamantane derivatives of our invention solidifies into small size pellets with the perfume and/or flavor imprisoned therein. The apparatus useful in conjunction with this process advantageously includes a conveyor of a material which will not adhere to the polymer which contains at least one of the adamantane derivatives of our invention.

In order that the droplets form into uniform pellets or beads, the conveyor is continuously washed with a liquid such as water to maintain the surface relatively cool. The pellets are delivered by the conveyor into a container and packaged for shipment or for further incorporation ito articles of manufacture, e.g., garbage bags (using the deodorization quality of the adamantane derivatives of our invention) or tobacco filters (using the tobacco flavoring or flavor enhancement properties of the adamantane derivatives of our invention).

The following Examples A, I and II set forth the preparation of the precursors of the adamantane derivatives of our invention. Examples III–XVI set forth preparation of the adamantane derivative compositions of our invention. Examples XVIII, et seq. set forth the organoleptic uses of the adamantane derivatives of our invention prepared according to Examples III–XVI.

The following Examples III, et seq. serve to illustrate our invention, and this invention is to be considered restricted thereto only as indicated in the appended claims.

All parts and percentages given herein are by weight unless otherwise specified.

EXAMPLE A

PREPARATION OF
3(4-METHYL-3-CYLOHEXEN-1-YL)BUTANAL

Reaction:

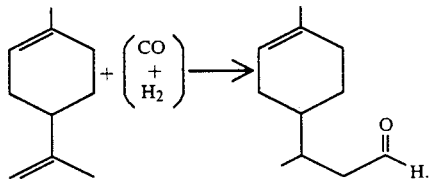

PART I

PRODUCTION OF OXO REACTION CATALYST 150 ml Methanol is admixed with 36 grams of triphenyl phosphine, 1.2 grams of $RhCl_3.H_2O$ and 2.4 grams of sodium bicarbonate. The resulting mixture is heated at reflux for a period of one hour and then cooled.

PART II

OXO REACTION

Into an autoclave rated for 1000 psig pressure and containing heating elements is placed 2583.7 grams (18.99 moles) of D-limonene having the structure:

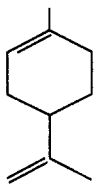

and the oxo reaction catalyst prepared in Part I, supra. The autoclave is sealed and heated to 110° C. and pressurized to 600 psig using a 50:50 mole:mole mixture of carbon monoxide and hydrogen. The autoclave pressure is then maintained at 600 psig and 110° C. for a period of eleven hours.

At the end of the eleven hour period, the autoclave is depressurized, the contents are cooled and the autoclave is opened. The contents of the autoclave are then distilled using a 2" splash column yielding the following fractions:

| Fraction No. | Vapor Temp. (°C.) | Liquid Temp. (°C.) | Vacuum mm/Hg. Pressure | Weight of Fraction (Grams) |
|---|---|---|---|---|
| 1 | 68/82 | 88/89 | 8/7 | 102.5 |
| 2 | 83 | 91 | 6 | 39.7 |
| 3 | 96 | 104 | 5 | 196.1 |
| 4 | 97 | 104 | 5 | 195.8 |
| 5 | 99 | 115 | 5 | 2318.3 |

-continued

| Fraction No. | Vapor Temp. (°C.) | Liquid Temp. (°C.) | Vacuum mm/Hg. Pressure | Weight of Fraction (Grams) |
|---|---|---|---|---|
| 6 | 93 | 119 | 5 | 107.6 |
| 7 | 80 | 125 | 4 | 10.0 |

The resulting product, having the structure:

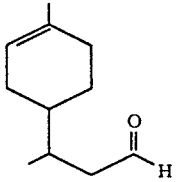

is then utilized in the following Example I.

FIG. 47 is the GLC profile for the crude reaction product prior to distillation. The peak indicated by reference numeral 5 is the peak for the compound having the structure:

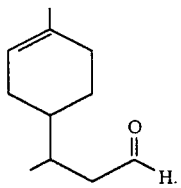

(Conditions: K-20M column programmed at 130°-220° C. at 8= C. per minute.

EXAMPLE I

PREPARATION OF 2-METHYLENE-3-(4-METHYL-3-CYCLOHEX-ENYL)BUTANAL

Reaction:

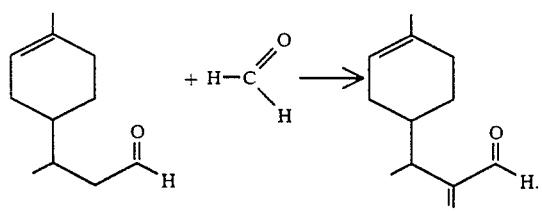

Into a 3 liter reaction vessel equipped with stirrer, thermometer, reflux condenser and heating mantle and nitrogen blanket apparatus is placed 613 grams (7.546 moles) of formaldehyde. 44.3 Grams (0.34 moles) of dibutyl amine is then added to the reaction mass. Over a period of 0.5 hours while maintaining the reaction mass at room temperature, 22.1 grams (0.37 moles) of acetic acid is added dropwise to the reaction mass.

The reaction mass, with stirring, is heated to 90°-95° C.

While maintaining the reaction mass at 90°-95° C. over a period of 0.5 hours, 1140 grams (6.86 moles) of the compound having the structure:

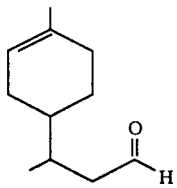

is added to the reaction mass.

The reaction mass is then refluxed for a period of 30 hours at 90°-95° C.

At the end of the 30 hour period, the reaction mass is cooled and washed with:

(a) water;

(b) 5% aqueous sodium carbonate; and (c) saturated sodium chloride solution.

686.5 Grams of the compound having the structure:

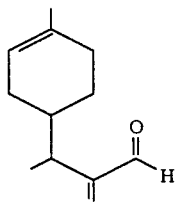

are produced (percent weight yield:60.2%).

The resulting washed product is then fractionally distilled on a 2" splash column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | /75 | /96 | 2.2 | 92.0 |
| 2 | 84 | 106 | 2.0 | 394.8 |
| 3 | 32 | 12 | 2.0 | 665.0 |

Fractions 2, 3, 4, 5 and 6 are bulked and redistilled on a 1" Goodloe column yieldign the following fractions:

| Fraction No. | Vapor Temp. (°C.) | Liquid Temp. (°C.) | Vacuum mm/Hg. Pressure | Reflux Ratio | Weight of Fraction (Grams) |
|---|---|---|---|---|---|
| 1 | /70 | /91 | 1.4 | 12:1 | 29 |
| 2 | 74 | 90 | 1.5 | 12:1 | 26 |
| 3 | 83 | 101 | 2.3 | 9:1 | 58 |
| 4 | 82 | 101 | 2.1 | 9:1 | 60 |
| 5 | 83 | 101 | 2.2 | 9:1 | 79 |
| 6 | 82 | 101 | 1.6 | 9:1 | 78 |
| 7 | 85 | 103 | 1.7 | 7:1 | 92 |
| 8 | 85 | 103 | 1.7 | 7:1 | 56 |
| 9 | 79 | 104 | 1.5 | 7:1 | 100 |
| 10 | 80 | 107 | 1.6 | 7:1 | 101 |
| 11 | 80 | 119 | 1.6 | 7:1 | 81 |
| 12 | 80 | 165 | 1.6 | 7:1 | 35 |

FIG. 1 is the GLC profile for the crude reaction product. The peak indicated by reference numeral 10 is the peak for the compound having the structure:

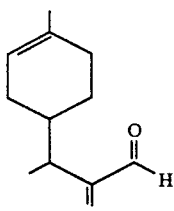

(Conditions: K-20M column programmed at 130°–200° C. at 8° C. per minute).

FIG. 2 is a cross scan GC profile for the crude reaction product. The peak indicated by reference numeral 21 is the peak for the compound having the structure:

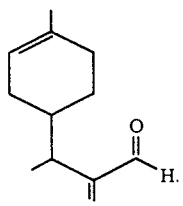

The peaks indicated by reference numerals 22 and 23 are the peaks for byproducts of the reaction having the structure:

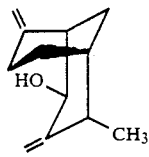

wherein in each of the compounds one of the dashed lines is a carbon-carbon double bond and the other of the dashed lines is a carbon-carbon single bond and each of the compounds is different from the other.

FIG. 3 is the NMR spectrum for the compound having the structure:

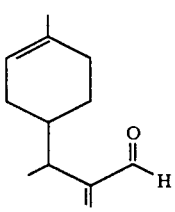

(CFCl₃ solvent) at 100 MHz.

EXAMPLE II

PREPARATION OF 2-METHYLENE-3-(4-METHYL-3-CYCLOHEXENYL)BUTANAL

Reaction:

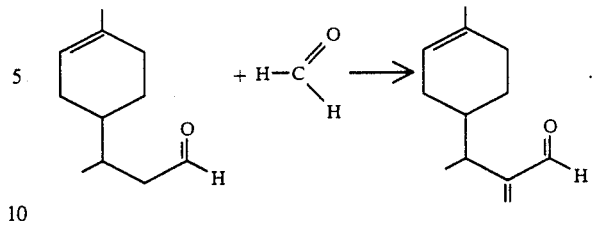

Into a 3 liter reaction vessel equipped with stirrer, thermometer, reflux condenser and heating mantle are placed 1410 grams (17.35 moles) of formaldehyde and 101.3 grams (0.78 moles) of dibutyl amine. Over a period of 15 minutes, 82.8 grams (1.38 moles) of acetic acid is added to the reaction mass. The reaction mass is then heated to 90° C. and over a period of 35 minutes 2640 grams (15.9 moles) of the compound having the structure:

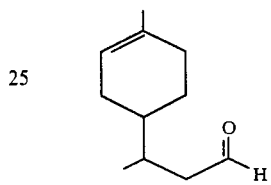

is added to the reaction mass with stirring. The reaction mass is maintained with stirring at 90° C. for a period of 2 hours. At the end of the 2 hour period, the reaction mass is extracted with one volume of toluene. The toluene extract is then washed as follows:

(a) one volume of 5% phosphoric acid;
(b) one volume of water; and
(c) one volume of saturated sodium bicarbonate.

The reaction mass is then distilled on a 2" splash column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | /43 | /80 | 3.00/2.4 | |
| 2 | 103 | 113 | 0.5 | 356 |
| 3 | 118 | 125 | 1.7 | 869 |
| 4 | 120 | 127 | 2.9 | 849 |
| 5 | 129 | 170 | 1.8 | 771 |
| 6 | 95 | 203 | 1.7 | 153. |

The weight yield is 93% of product having the structure:

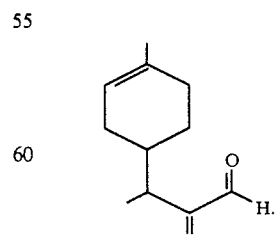

FIG. 4 is the GLC profile for fraction 4 of the foregoing distillation (Conditions: K-20M column programmed at 130°–220° C. at 8° C. per minute). The peak indicated by reference numeral 41 is the peak for the compound having the is the peak for the compound having the structure:

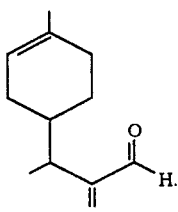

EXAMPLE III

PREPARATION OF 2-HYDROXY-4-METHYLENE-8-METHYL TRICYCLO[3.3.1.1³,⁷] DECANE (ALSO NAMED 4-METHYL-8-METHYLENE-2-ADAMANTOL)

Reaction:

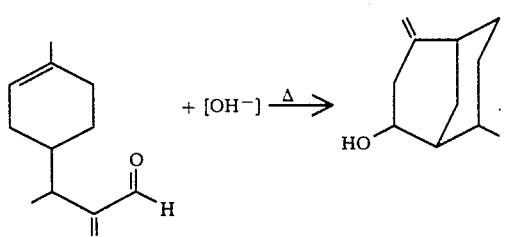

Into a 5 liter reaction vessel equipped with stirrer, thermometer, reflux condenser and heating mantle are placed 100 grams PRIMOL ® and 26 grams of sodium bicarbonate. The reaction mass is heated to 78° C. While maintaining the reaction mass at 78° C. over a period of one hour, 835 grams of the compound having the structure:

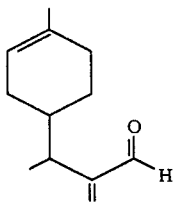

prepared according to Example II is added to the reaction vessel. During the addition the reaction vessel is heated up slowly to 210° C. While maintaining the reaction mass at 200°–210° C. over a period of 2.5 hours an additional 1665 grams of the compound having the structure:

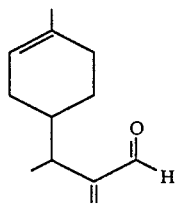

is added to the reaction mass with stirring. The reaction mass is then stirred at a temperature in the range of 208°–212° C. for a period of two hours.

The reaction mass is then distilled on a packed column packed with Raschig Rings yielding the following fractions:

| Fraction No. | Vapor Temp. (°C.) | Liquid Temp (°C.) | Vacuum mm/Hg. Pressure | Weight of Fraction (Grams) |
| --- | --- | --- | --- | --- |
| 1 | 117/ | 135/ | 8.0 | 40 |
| 2 | 122 | 137 | 7.8 | 171 |
| 3 | 128 | 141 | 8.7 | 196 |
| 4 | 129 | 143 | 11.7 | 414 |
| 5 | 137 | 153 | 12.1 | 844 |
| 6 | 133 | 191 | 5.7 | 673 |
| 7 | 109 | 205 | 5.0 | 6. |

FIG. 5 is the GLC profile for the crude reaction product. The peaks indicated by reference numerals 52 and 53 are peaks indicating solvent. The peak indicated by reference numeral 51 is the peak for the reaction product having the structure:

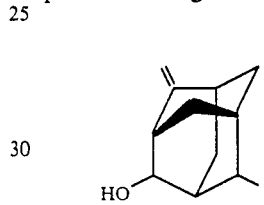

which is a mixture of isomers having the structures:

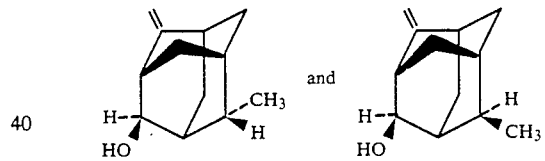

(Conditions: Carbowax column programmed at 130°–220° C. at 8° C. per minute).

Bulked distillation fractions 6–9 have a sandalwood, woody, patchouli, rhubarb, ginger, minty and amyris aroma with amyris, camphoraceous, patchouli, woody and piney topnotes.

EXAMPLE III (A)

PREPARATION OF 2-HYDROXY-4-METHYLENE-8-METHYL TRICYCLO[3.3.1.1³,⁷] DECANE (ALSO NAMED 4-METHYL-8-METHYLENE-2-ADAMANTOL

Reaction:

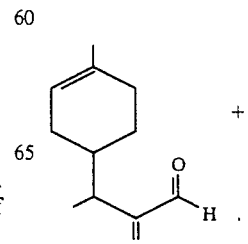

-continued

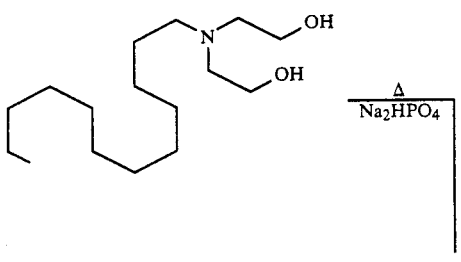

Into a 20 ml Parr bomb set in an oil bath is placed 10 grams of the compound having the structure:

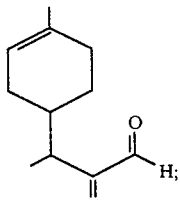

0.5 grams of Na₂HPO₄; and 5 grams of ETHOMEEN® C-12 (n-dodecyl-di-hydroxyethyl amine manufactured by the Rohm And Haas & Company of Philadelphia, Penn.).

The Parr bomb is closed and the oil bath is heated to 200°-240° C. and maintained at 200°-240° C. for a period of three hours.

At the end of the three hour period, the Parr bomb is cooled and opened and the reaction mass is analyzed.

FIG. 5A is the GLC profile for the crude reaction product. The peak indicated by FIG. 54 is the peak for one or both of the compounds defined according to the structure:

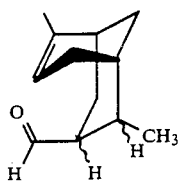

wherein one of the dashed lines is a carbon-carbon double bond and the other of the dashed lines is a carbon-carbon single bond; the peaks indicated by FIGS. 56 and 57 are for one or both of the compounds defined according to the structure:

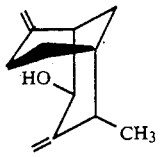

wherein one of the dashed lines is a carbon-carbon double bond and the other of the dashed lines is a carbon-carbon single and the peak indicated by reference numeral 55 is the peak for the compound defined according to the structure:

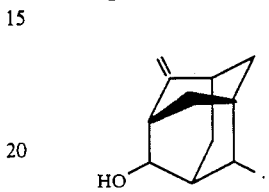

FIG. 5B is the NMR spectrum for the compound having the structure:

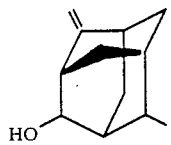

(a mixture of isomers having the structures:

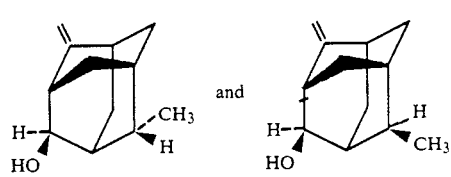

FIG. 5C is the NMR spectrum for one or both of the compounds defined according to the structure:

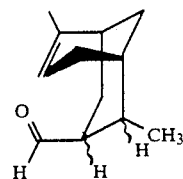

wherein one of the dashed lines is a carbon-carbon double bond and the other of the dashed lines is a carbon-carbon single bond.

The reaction product has a camphoraceous, gingery, cardamon and woody aroma profile.

EXAMPLE IV

PREPARATION OF 4-METHYLENE-8-METHYL TRICYCLO[3.3.1.1³,⁷]DECANYL-2-FORMATE (ALSO NAMED 8-METHYL-4METHYLENE-2-ADAMANTOL FORMATE)

Reaction:

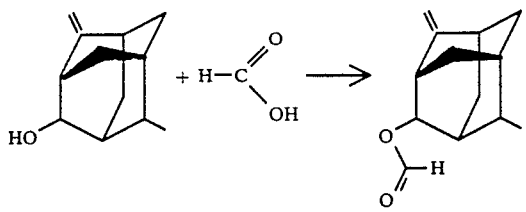

Into a 2 liter reaction vessel equipped with stirrer, thermometer, reflux condenser and heating mantle are placed 677 grams (3.8 moles) of the compound having the structure:

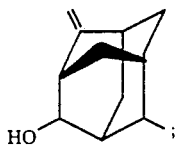

240 grams of formic acid and 2 grams of oxalic acid. The resulting mixture with stirring is heated to 80° C. Over a period of three hours, 530 grams of acetic anhydride is fed into the reaction mass while maintaining the reaction mass at 90°–95° C. The reaction mass is then maintained at 82°–83° C. for a period of 0.70 hours. the reaction mass is then cooled and the aqueous phase is separated from the organic phase. The aqueous phase is extracted with 100 cc of toluene and the toluene extract is combined with the organic phase. The organic layer is then washed as follows:

(a) one 400 ml portion of saturated sodium chloride solution;
(b) one portion of 5% aqueous sodium bicarbonate; and
(c) two portions of saturated sodium chloride.

The resulting product is then dried over anhydrous magnesium sulfate and distilled on 2" splash column yielding the following fractions:

| Fraction No. | Vapor Temp. (°C.) | Liquid Temp. (°C.) | Vacuum mm/Hg. Pressure | Weight of Fraction (Grams) |
|---|---|---|---|---|
| 1 | 55/ | 74/ | 100 | |
| 2 | 60 | 105 | 270 | |
| 3 | 49 | 83 | 115 | |
| 4 | 52 | 110 | 65 | 52 |
| 5 | 45/108 | 128/118 | 70/4.5 | 80 |
| 6 | 97 | 107 | 1.6 | 150 |
| 7 | 96 | 104 | 1.4 | 103 |
| 8 | 95 | 103 | 1.3 | 82 |
| 9 | 97 | 107 | 1.2 | 119 |
| 10 | 108 | 128 | 1.3 | 84 |
| 11 | 128 | 190 | 1.6 | 39 |
| 12 | 128 | 200 | 1.8 | 8. |

Fractions 4–10 are bulked and redistilled on a 1"×10" Goodloe column yielding the following fractions:

| Fraction No. | Vapor Temp. (°C.) | Liquid Temp. (°C.) | Vacuum mm/Hg. Pressure | Reflux Ratio | Weight of Fraction (Grams) |
|---|---|---|---|---|---|
| 1 | 77/56 | 114/133 | 1.5/1.4 | 19:1 | 53 |
| 2 | 92 | 120 | 1.6 | 9:1 | 17 |
| 3 | 93 | 114 | 1.6 | 9:1 | 13 |
| 4 | 97 | 118 | 1.7 | 4:1 | 18 |
| 5 | 94 | 119 | 1.5 | 4:1 | 35 |
| 6 | 95 | 119 | 1.5 | 4:1 | 27 |
| 7 | 96 | 116 | 1.66 | 4:1 | 43 |
| 8 | 96 | 116 | 1.56 | 4:1 | 42 |
| 9 | 97 | 116 | 1.75 | 4:1 | 37 |
| 10 | 97 | 116 | 1.63 | 4:1 | 52 |
| 11 | 98 | 117 | 1.60 | 4:1 | 51 |
| 12 | 96 | 117 | 1.55 | 4:1 | 42 |
| 13 | 97 | 118 | 1.60 | 4:1 | 44 |
| 14 | 97 | 125 | 1.57 | 4:1 | 40 |
| 15 | 97 | 138 | 1.51 | 4:1 | 36 |
| 16 | 98 | 150 | 1.63 | 4:1 | 20 |
| 17 | 112 | 180 | 1.77 | 4:1 | 13. |

FIG. 6 is the GLC profile for the crude reaction product prior to distillation containing the compound having the structure:

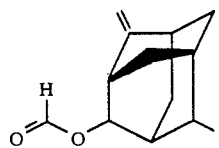

(Conditions: Carbowax column programmed at 130°–220° C. at 8° C. per minute).

FIG. 7 is the NMR spectrum for the compound having the structure:

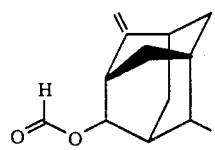

The compound having the structure:

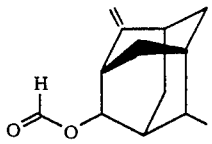

has a woody, cedarwood-like, sandalwood-like, camphoraceous, minty and earthy aroma profile with cedarwood, sandalwood, patchouli, camphoraceous, herbaceous, incense and olibanum topnotes (bulked distillation fractions 8–18).

EXAMPLE V(A)

PREPARATION OF 4-METHYLENE-8-METHYL-TRICYCLO[3.3.1.1$^{3,7}$]DECAN-2YL ACETATE(ALSO NAMED 8-METHYL-4-METHYLENE-2-ADAMANTOL ACETATE)

Reaction:

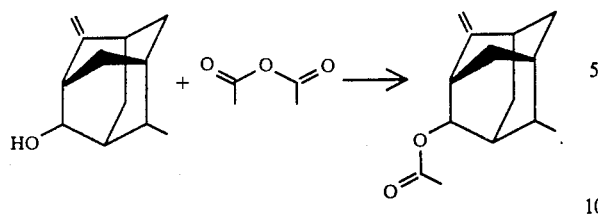

Into a 500 ml reaction flask equipped with stirrer, thermometer, reflux condenser and heating mantle is placed 100 grams of acetic anhydride. The acetic anhydride is heated to 80° C. and over a period of 0.5 hours, 71 grams of the compound having the structure:

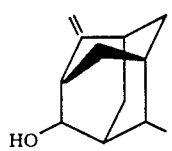

is added to the acetic anhydride (dropwise). The reaction mass is then heated between 78° and 80° C. for a period of five hours and is then refluxed at 115° C. for a period of four hours.

FIG. 8 is the GLC profile for the crude reaction product. The peaks indicated by reference numerals 81 and 82 are the peaks for the two isomers of the compound having the structure:

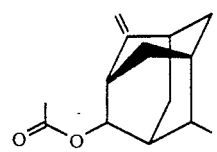

which two isomers have the structures:

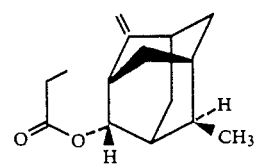

and

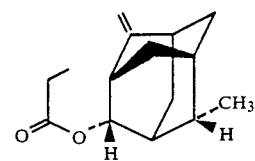

(Conditions: Carbowax column programmed at 130°-220° C. at 8° C. per minute).

FIG. 9 is the NMR spectrum for the compound having the structure:

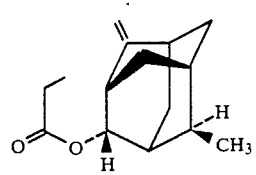

FIG. 10 is the NMR spectrum for the compound having the structure:

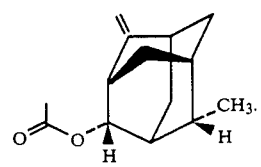

EXAMPLE V(B)

PREPARATION OF 4-METHYLENE-8-METHYL-TRICYCLO[3.3.1.1$^{3,7}$]DECAN-2-YL ACETATE(ALSO NAMED 8-METHYL-4-METHYLENE-2-ADAMANTOL ACETATE)

Reaction:

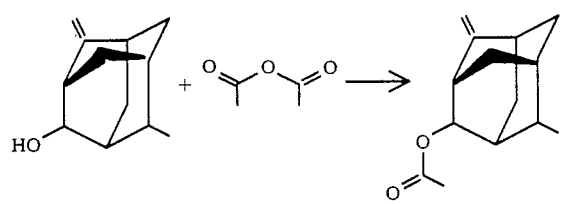

Into a 1 liter reaction vessel equipped with stirrer, thermometer, reflux condenser and heating mantle are placed 180 grams of acetic anhydride. The acetic anhydride is heated to 95° C. and over a period of 0.5 hours, 298 grams of the compound having the structure:

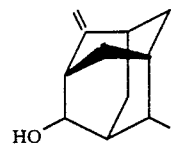

is added to the acetic anhydride, dropwise without refluxing. 100 Grams of toluene is added to the reaction mass and the reaction mass is heated at 97°-99° C. for a period of one hour. At the end of the one hour period, the reaction mass is distilled on a 1"×10" Goodloe column yielding the following fractions:

| Fraction No. | Vapor Temp. (°C.) | Liquid Temp. (°C.) | Vacuum mm/Hg. Pressure | Reflux Ratio | Weight of Fraction (Grams) |
|---|---|---|---|---|---|
| 1 | 103/ | 133/ | 250/ | 1:1 | 183 |
| 2 | 56 | 109 | 44.0 | 1:1 | 123 |
| 3 | 78 | 123 | 2.2 | 4:1 | 38 |
| 4 | 108 | 138 | 2.6 | 4:1 | 88 |
| 5 | 102 | 121 | 2.63 | 4:1 | 30 |
| 6 | 104 | 123 | 2.76 | 4:1 | 33 |

-continued

| Fraction No. | Vapor Temp. (°C.) | Liquid Temp. (°C.) | Vacuum mm/Hg. Pressure | Reflux Ratio | Weight of Fraction (Grams) |
|---|---|---|---|---|---|
| 7 | 98 | 121 | 2.18 | 4:1 | 30 |
| 8 | 98 | 120 | 2.14 | 4:1 | 25 |
| 9 | 98 | 121 | 2.19 | 4:1 | 24 |
| 10 | 98 | 125 | 2.10 | 4:1 | 20 |
| 11 | 97 | 138 | 2.02 | 4:1 | 19 |
| 12 | 98 | 180 | 2.09 | 4:1 | 14 |
| 13 | 95 | 200 |  | 4:1 | 5 |

FIG. 11 is the GLC profile for the crude reaction product containing the compounds having the structures:

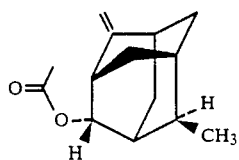

and

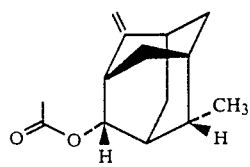

(Conditions: Carbowax column programmed at 130°–220° C. at 8° C. per minute). Bulked distillation fractions 7-9 have a cedarwood-like, patchouli, vetiver, peppery, grapefruit peel-like and camphoraceous aroma profile with woody, vetiver and grapefruit peel-like topnotes.

EXAMPLE VI

PREPARATION OF 4-METHYLENE-8-METHYL TRICYCLO[3.3.1.1³,⁷]DECAN-2-YL PROPIONATE (ALSO NAMED 4-METHYL-8-METHYLENE-2-ADAMANTOL PROPIONATE)

Reaction:

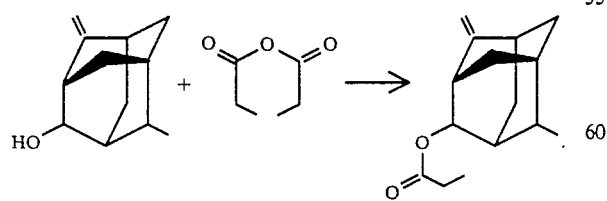

Into a 1 liter reaction vessel equipped with stirrer, thermometer, reflux condenser and heating mantle is placed 356 grams of the compound having the structure:

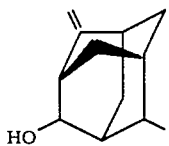

The compound having the structure:

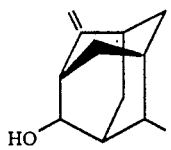

is heated to 80°–90° C. and over a period of one hour while maintaining the reaction mass at 88° C., 340 grams of propionic anhydride is added to the reaction mass with stirring.

The reaction mass is then maintained at 88° C. for a period of four hours whereupon the reaction temperature is raised to 110° C. and maintained at that temperature for a period of one hour.

The reaction mass is then distilled on a 1½″×12″ Goodloe column yielding the following fractions:

| Fraction No | Vapor Temp. (°C.) | Liquid Temp. (°C.) | Vacuum mm/Hg. Pressure | Reflux Ratio | Weight of Fraction (Grams) |
|---|---|---|---|---|---|
| 1 | 78/55 | 118/116 | 135/16 | 3:1 |  |
| 2 | 52 | 102 | 6.6 | 9:1 | 24 |
| 3 | 53 | 122 | 6.1 | 9:1 | 29 |
| 4 | 56 | 137 | 2.2 | 9:1 | 35 |
| 5 | 108 | 133 | 2.3 | 9:1 | 26 |
| 6 | 117 | 138 | 2.0 | 9:1 | 34 |
| 7 | 102 | 132 | 1.3 | 9:1 | 27 |
| 8 | 101 | 131 | 1.3 | 9:1 | 28 |
| 9 | 104 | 133 | 1.4 | 9:1 | 10 |
| 10 | 113 | 133 | 2.1 | 9:1 | 29 |
| 11 | 113 | 135 | 1.9 | 9:1 | 45 |
| 12 | 120 | 137 | 2.6 | 9:1 | 31. |
| 13 | 120 | 137 | 2.8 |  | 29 |
| 14 | 120 | 138 | 2.6 |  | 32 |
| 15 | 120 | 138 | 2.64 |  | 28 |
| 16 | 119 | 141 | 2.47 |  | 26 |
| 17 | 120 | 152 | 2.60 |  | 25 |
| 18 | 120 | 154 | 2.64 |  | 20 |
| 19 | 120 | 180 | 2.64 |  | 26. |

FIG. 12 is the GLC profile for the crude reaction product containing the compound having the structure:

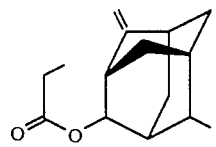

(Conditions: Carbowax column programmed at 130°–220° C. at 8° C. per minute).

FIG. 13 is the NMR spectrum for the compound having the structure:

The compound having the structure:

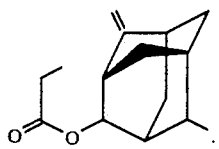

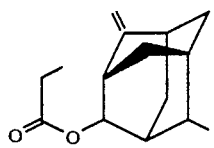

(bulked fractions 10-16 has a woody, rose-like, peony-like aroma profile with floral, sweet pea, rose and peony topnotes).

When fractions 5-19 are bulked, the resulting mixture has an ambery, woody and cedarwood-like aroma profile with fruity and woody topnotes.

EXAMPLE VII

PREPARATION OF 4-METHYLENE-8-METHYL TRICYLO[3.3.1.1³,⁷]DECAN-2ONE (ALSO NAMED 8-METHYL-4-METHYLENE ADAMANTONE-2)

Reaction:

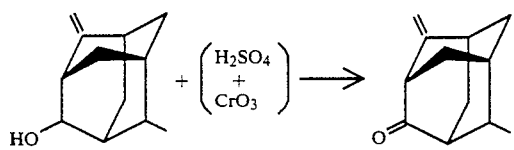

Into a 5 liter reaction vessel equipped with stirrer, thermometer, reflux condenser and heating mantle are placed 280 ml acetone and 420 grams of the compound having the structure:

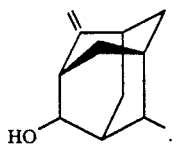

The resulting mixture is cooled to 15° C. Slowly over a period of five hours a mixture of 235 grams of chromium trioxide and 205 grams of sulfuric acid and 1500 ml water is added dropwise while maintaining the reaction mass at 25° C.

At the end of the five hour addition period, the reaction mass is stirred at 25° C. for a period of eight hours.

The organic phase is separated from the aqueous phase and the aqueous phase is extracted with toluene. The toluene extract is combined with the organic phase and the resulting product is distilled on a 2" splash column yielding the following fractions:

| Fraction No. | Vapor Temp. (°C.) | Liquid Temp (°C.) | Vacuum mm/Hg. Pressure | Weight of Fraction (Grams) |
|---|---|---|---|---|
| 1 | 37/85 | 76/100 | /400 | 256 |
| 2 | 87 | 109 | 400 | 202 |
| 3 | 69 | 107 | 400-50 | 188 |
| 4 | 107 | 128 | 3.6 | ⎫ |
| 5 | 112 | 148 |  | ⎬ 205 |
| 6 | 120 | 175 | 2.0 | ⎭ |
|   |     |     |     | ⎫ |
| 7 | 120 | 180 | 1.0 | ⎬ 9 |
|   |     |     |     | ⎭ |
|   |     |     |     | 214. |

Fractions 4, 5 and 6 are bulked and redistilled on a 1"×10" Goodloe column yielding the following fractions:

| Fraction No. | Vapor Temp. (°C.) | Liquid Temp. (°C.) | Vacuum mm/Hg. Pressure | Weight of Fraction (Grams) |
|---|---|---|---|---|
| 1 | 72/93 | 108/115 | 2.17/2.11 | 13 |
| 2 | 93 | 116 | 2.01 | 17 |
| 3 | 93 | 117 | 2.0 | 19 |
| 4 | 94 | 118 | 2.0 | 27 |
| 5 | 95 | 117 | 2.0 | 25 |
| 6 | 93 | 118 | 2.1 | 10 |
| 7 | 95 | 118 | 2.1 | 20 |
| 8 | 95 | 120 | 2.1 | 15 |
| 9 | 95 | 126 | 2.1 | 17 |
| 10 | 90 | 200 | 2.1 | 15. |

FIG. 14 is the GLC profile for the crude reaction product prior to distillation (Conditions: Carbowax column programmed at 130°-220° C. at 8° C. per minute).

FIG. 15 is the NMR spectrum of the compound having the structure:

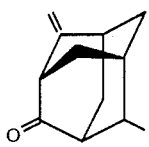

The compound having the structure:

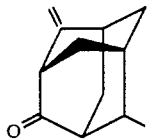

(bulked fractions 4-8) has a camphoraceous aroma with early morning forest path, green, piney, woody and camphoraceous topnotes.

EXAMPLE VIII

PREPARATION OF 2-HYDROXY-4-METHYLENE-2,8-DIMETHYL-TRICYCLO[3.3.1.1³,⁷] DECAN (ALSO NAMED 2,8-DIMETHYL-4-METHYLENE-2-ADAMANTOL)

Reactions:

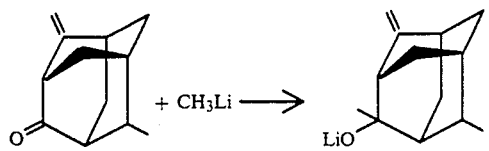

and

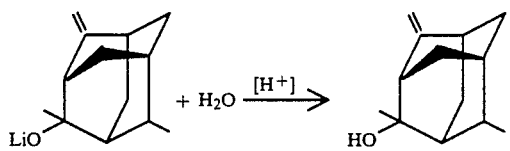

Into a microvial reaction vessel placed in an ice bath and cooled to 0° C. is added 1 gram of lithium in 1 ml diethyl ether. To the resulting mixture is added 0.44 grams of the compound having the structure:

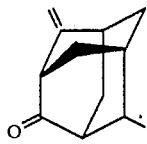

prepared according to Example VII. The reaction mixture is permitted to stand for a period of 2.5 hours.

A mixture of 1:1 methanol:toluene is then added to the resulting product. 15 ml Saturated sodium chloride is then added to the resulting product. The resulting productis a solid.

FIG. 16 is a GLC profile of the reaction product. (Conditions: Carbowax column programmed at 130°-220° C. at 8° C. per minute). The peak indicated by reference numeral 162 is the peak for the compound having the structure:

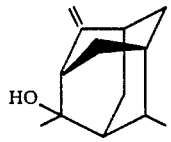

The peak indicated by reference numeral 161 is for another isomer of the compound having the structure:

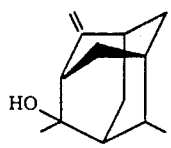

The peak indicated by reference numeral 163 is for yet another isomer of the compound having the structure:

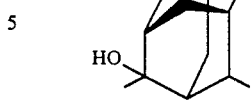

The peak indicated by reference numeral 164 is for the compound having the structure:

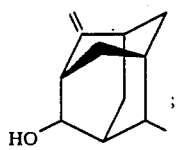

a mixture of isomers having the structures:

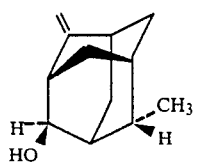

and

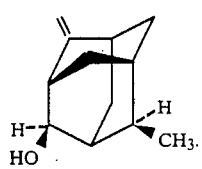

FIG. 17 is the NMR spectrum for the compound of peak 161 of FIG. 16; an isomer of the compound having the structure:

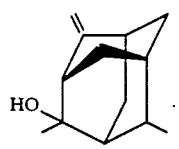

FIG. 18 is the NMR spectrum of the peak indicated by reference numeral 162 of FIG. 16; an isomer of the compound having the structure:

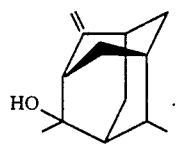

FIG. 19 is the NMR spectrum for the peak indicated by reference numeral 163 of FIG. 16; another isomer of the compound having the structure:

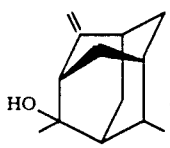

FIG. 20 is the NMR spectrum for the peak indicated by reference numeral 164 of FIG. 16; for the compound having the structure:

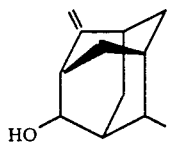

a mixture of isomers having the structures:

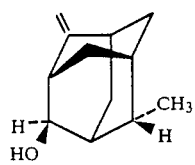

and

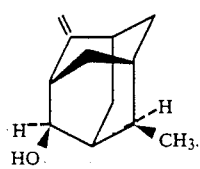

EXAMPLE IX

PREPARATION OF 4-METHYLENE-2,8-DIMETHYL-TRICYCLO[3.3.1.1$^{3,7}$]DECAN-2-YL ACETATE (ALSO HAVING THE NAME 2,8-DIMETHYL-4-METHYLENE-2-ADAMANTOL ACETATE)

Reaction:

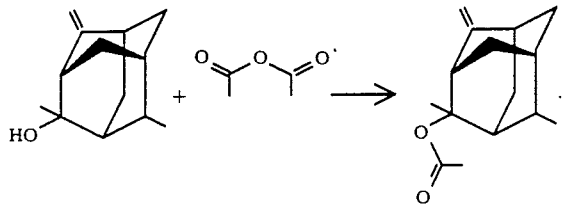

Into a 2 dram vial immersed in a 10 ml beaker equipped with water bath and hot plate is placed 0.71 grams of the compound having the structure:

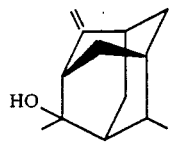

and 0.34 grams of acetic anhydride. The resulting mixture is heated to 80°–100° C. for a period of one hour.

The resulting product has the structure:

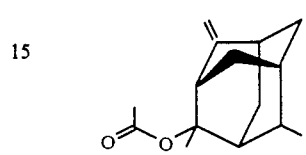

FIG. 21 is the GLC profile of the crude reaction product containing the compound having the structure:

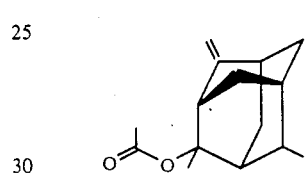

EXAMPLE X

PREPARATION OF 2-HYDROXY-4,8-DIMETHYL TRICYCLO[3.3.1.1$^{3,7}$]DECAN (ALSO NAMED 2,8-DIMETHYL-2-ADAMANTOL)

Reaction:

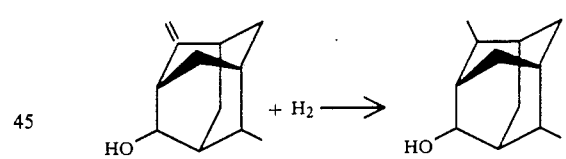

Into a 1 liter Parr bomb is placed 543.9 grams of the compound having the structure:

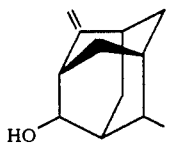

200 ml isopropyl alcohol and 5.5 grams of palladium on carbon catalyst (10% palladium on carbon). The Parr bomb is sealed and pressurized to 100 psig with hydrogen and maintained at a temperature of 100° C. with stirring for a period of two hours. At the end of the two hour period, the Parr bomb is cooled and the contents are filtered.

The solvent (isopropyl alcohol) is stripped under vacuum and the resulting product is distilled on a 2" splash column yielding the following fractions:

| Fraction No. | Vapor Temp. (°C.) | Liquid Temp. (°C.) | Vacuum mm/Hg. Pressure | Weight of Fraction (Grams) |
|---|---|---|---|---|
| 1 | 40/ | 99/ | | 16 |
| 2 | 119 | 141 | | 164 |
| 3 | 125 | 145 | 7 | |
| 4 | 125 | 150 | 7 | 352 |
| 5 | 120 | 159 | 7 | |

Fractions 3 and 4 are bulked and redistilled on a 1"×10" Goodloe column yielding the following fractions:

| Fraction No. | Vapor Temp. (°C.) | Liquid Temp. (°C.) | Vacuum mm/Hg. Pressure | Reflux Ratio | Weight of Fraction Grams |
|---|---|---|---|---|---|
| 1 | 118/125 | 137/141 | 7.1/6.9 | 4:1 | 17 |
| 2 | 126 | 144 | 7.2 | 4:1 | 37 |
| 3 | 127 | 145 | 7.5 | 4:1 | 31 |
| 4 | 130 | 152 | 7.6 | 4:1 | 54 |
| 5 | 137 | 155 | 7.7 | 4:1 | 50 |
| 6 | 134 | 163 | 8.1 | 4:1 | 22 |
| 7 | 137 | 155 | 6.5 | 4:1 | 37 |
| 8 | 126 | 151 | 6.1 | 4:1 | 29. |

FIG. 22 is the GLC profile for the crude reaction product prior to distillation. The peak indicated by reference numeral 2200 is the peak for the compound having the structure:

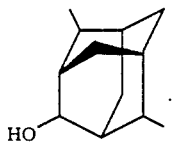

The peak indicated by reference numeral 2200 is the peak for the compound having the structure:

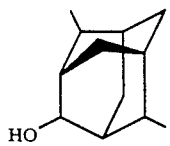

(Conditions: Carbowax column programmed at 130°-220° C. at 8° C. per minute).

FIG. 23 is the NMR spectrum for the compound having the structure:

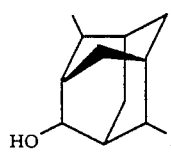

The compound having the structure:

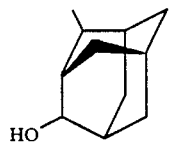

(bulked fractions 4 and 5) has a spicy, ginger root, rosemary and camphoraceous aroma profile with green, woody and ginger root topnotes.

EXAMPLE XI

PREPARATION OF 4,8-DIMETHYL TRICYCLO[3.3.1.1$^{3,7}$]DECAN-2-YL ACETATE (ALSO NAMED 4,8-DIMETHYL-2-ADAMANTOL ACETATE)

Reaction:

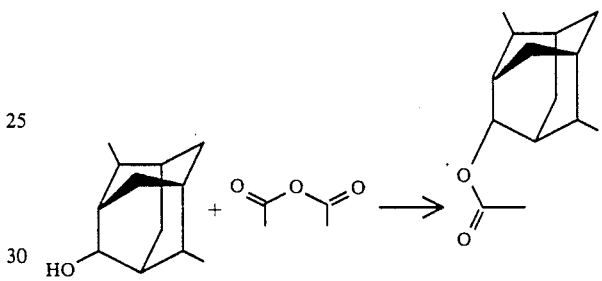

Into a 1 liter reaction vessel equipped with stirrer, thermometer, reflux condenser and heating mantle are placed 120 grams of tetrahydrofuran and 199 grams of the compound having the structure:

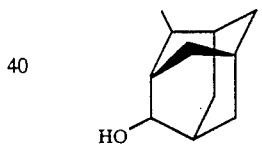

prepared according to Example X. The resulting mixture is heated to 110° C. Over a period of two hours, 130 grams of acetic anhydride is added to the reaction mass while maintaining the temperature of the reaction mass at 110° C.

At the end of the addition period for the acetic anhydride, the reaction mass is cooled to 50°-60° C. and transferred to a distillation pot.

The resulting product is first stripped of excess acetic anhydride under vacuum and distilled on a 1"×10" Goodloe column yielding the following fractions:

| Fraction No. | Vapor Temp. (°C.) | Liquid Temp. (°C.) | Vacuum mm/Hg. Pressure | Reflux Ratio | Weight of Fraction (Grams) |
|---|---|---|---|---|---|
| 1 | 54/ | 138/ | 20/ | 4:1 | 17 |
| 2 | 76 | 142 | 3.2 | 4:1 | 10 |
| 3 | 118 | 134 | 3.0 | 4:1 | 19 |
| 4 | 118 | 135 | 2.9 | 4:1 | 20 |
| 5 | 118 | 136 | 2.8 | 4:1 | 23 |
| 6 | 118 | 135 | 2.8 | 9:1 | 29 |
| 7 | 117 | 138 | 2.7 | 9:1 | 35 |
| 8 | 116 | 147 | 2.6 | 9:1 | 17 |
| 9 | 121 | 156 | 3.2 | 9:1 | 23 |
| 10 | 122 | 167 | 3.3 | 9:1 | 20 |
| 11 | 121 | 200 | 3.4 | 9:1 | 13 |

| Fraction No. | Vapor Temp. (°C.) | Liquid Temp. (°C.) | Vacuum mm/Hg. Pressure | Reflux Ratio | Weight of Fraction (Grams) |
|---|---|---|---|---|---|
| 12 | 121 | 250 | | 9:1 | 6. |

FIG. 24 is the GLC profile for the reaction product containing the compound having the structure:

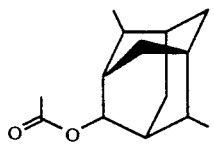

(Conditions: Carbowax column programmed at 130°-220° C. at 8° C. per minute).

FIG. 25 is the NMR spectrum for the compound having the structure:

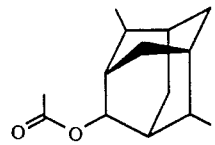

The compound having the structure:

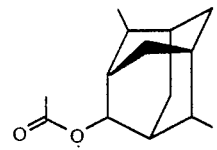

(bulked fractions 5-9) has a woody, ambery, vetiver, cedarwood, piney and chrysanthemum-like aroma profile with woody, amber and olibanum topnotes.

EXAMPLE XII

PREPARATION OF 4,8-DIMETHYL-TRICYCLO[3.3.1.1³,⁷]DECAN-2-ONE (ALSO NAMED 4,8-DIMETHYL-2-ADAMANTANONE)

Reaction:

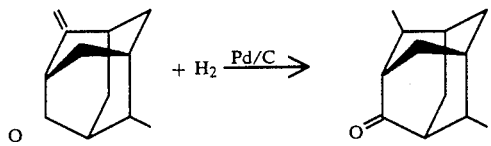

Into a 1 liter Parr bomb is placed 116 grams of methylethyl ketone; 2 grams of a palladium on carbon catalyst (10% palladium on carbon) and 115.5 grams (0.656 moles) of the compound having the structure:

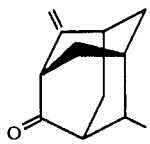

The Parr bomb is closed and heated to 100° C. and pressurized to a 100 psig-250 psig over a period of three hours with hydrogen. At the end of the three hour hydrogenation period, the Parr bomb is cooled and opened and the contents are filtered.

The filtrate is then distilled on a 2" splash column yielding the following fractions:

| Fraction No. | Vapor Temp. (°C.) | Liquid Temp. (°C.) | Vacuum mm/Hg. Pressure | Weight of Fraction (Grams) |
|---|---|---|---|---|
| 1 | /96 | /112 | 2.4 | 81.4 |
| 2 | 40 | 210 | 2.4 | 17.1. |

The distillation fractions are then redistilled on a 2 foot Goodloe column yielding the following fractions:

| Fraction No. | Vapor Temp. (°C.) | Liquid Temp. (°C.) | Vacuum mm/Hg. Pressure | Reflux Ratio | Weight of Fraction (Grams) |
|---|---|---|---|---|---|
| 1 | 82/89 | 119/127 | 1.6/1.6 | 9:1 | 14.1 |
| 2 | 89 | 128 | 1 6 | 9:1 | 9.1 |
| 3 | 95 | 146 | 3.0 | 9:1 | 8.1 |
| 4 | 98 | 205 | 3.0 | 9:1 | 13.3 |
| 5 | 98 | 230 | 1.6 | 9:1 | 3.6. |

FIG. 28 is the GLC profile for the crude reaction product prior to distillation (Conditions: SE-30 column programmed at 130°-220° C. at 8° C. per minute).

The resulting product has the structure:

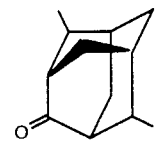

as confirmed by NMR, IR and mass spectral analyses.

EXAMPLE XIII

PREPARATION OF 4,8-DIMETHYL-TRICYCLO[3.3.1.1³,⁷]DECAN-2-YL ACETATE (ALSO NAMED 4,8-DIMETHYL-2-ADAMANTOL ACETATE)

Reaction:

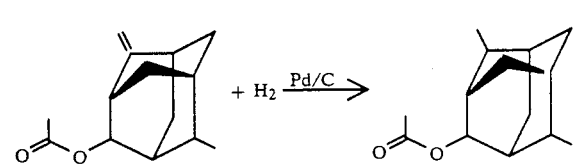

Into a 2 liter Parr bomb is placed 6 grams of 10% palladium on carbon catalyst; 600 grams of the compound having the structure:

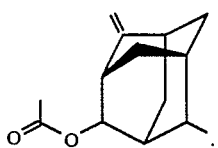

The Parr bomb is sealed and pressurized to 100 psig with hydrogen and heated at 100° C. for a period of 1.2 hours. At the end of the 1.2 hour period, the Parr bomb is cooled and the contents are filtered and distilled at 116°–118° C.; 2.6–3.0 mm/Hg. yielding 20 fractions.

FIG. 29 is the GLC profile of the reaction prior to distillation containing the compound having the structure:

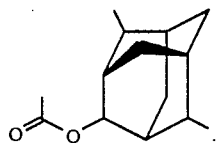

This compound has a woody, amber, vetiver, cedarwood, pine, chrysanthemum-like aroma with woody, olibanum and amber topnotes. (Bulked distillation fractions 2-18).

EXAMPLE XIV

"OXO" REACTION PRODUCT PRODUCED BY REACTION OF CARBON MONOXIDE AND HYDROGEN ON 2-HYDROXY-4-METHYLENE-8-METHYL TRICYCLO[3.3.1.1$^{3,7}$]DECANE

Reaction:

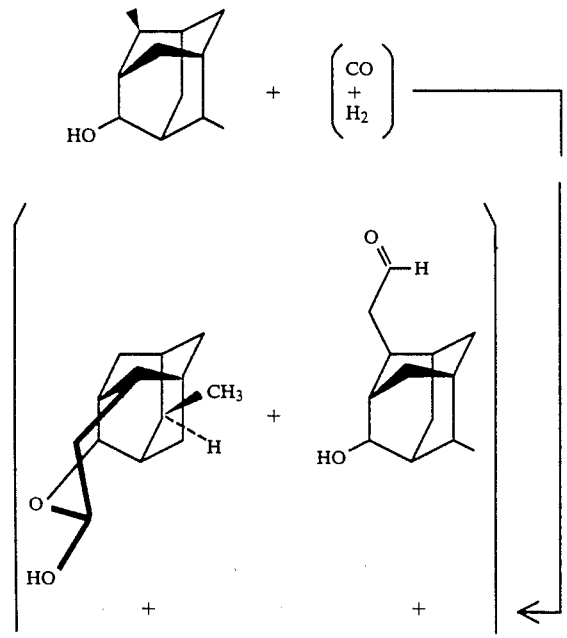

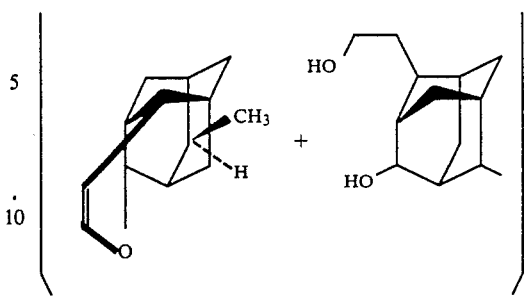

PART I

PRODUCTION OF OXO REACTION CATALYST 150 ml Methanol is admixed with 18 grams of triphenyl phosphine, 0.6 grams of RhCl$_3$.H$_2$O and 1.2 grams of sodium bicarbonate. The resulting mixture is heated at reflux for a period of one hour and then cooled.

PART II

OXO REACTION

Into a 2 liter autoclave rated for 1000 psig pressure and containing heating elements is placed 409.6 grams of the compound having the structure:

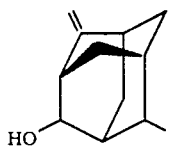

and 742 grams of toluene together with the oxo reaction catalyst prepared in Part I. The autoclave is sealed and heated to 100° C. and pressurized to 600 psig using a 50:50 mole:mole mixture of carbon monoxide and hydrogen. The autoclave pressure is then maintained at 600 psig and 100° C. for a period of 6.5 hours. At the end of the 6.5 hour period, the autoclave is depressurized, the contents are cooled and the autoclave is opened. The contents of the autoclave are then distilled using a 2" splash column yielding the following fractions:

| Fraction No. | Vapor Temp. (°C.) | Liquid Temp. (°C.) | Vacuum mm/Hg. Pressure | Weight of Fraction (Grams) |
|---|---|---|---|---|
| 1 | /37 | /63 | /100 | 75.5 |
| 2 | 43 | 105 | 100 | 78.8 |
| 3 | 30 | 110 | 80 | 21.5 |
| 4 | 85 | 154 | 70 | 53.3 |
| 5 | 128 | 175 | 80 | 107.0 |
| 6 | 155 | 186 | 80 | 105.8 |
| 7 | 159 | 194 | 2.3 | 98.1 |
| 8 | 120 | 220 | 1.4 | 53.9 |

FIG. 30 is the GLC profile for the crude reaction product prior to distillation (Conditions: SE-30 column programmed at 130°–220° C. at 8° C. per minute).

The peak indicated by reference numeral 301 is the peak for methyl alcohol solvent. The peak indicated by reference numeral 302 is the peak for the toluene solvent. The peak indicated by reference numeral 303 is the peak for the compound having the structure:

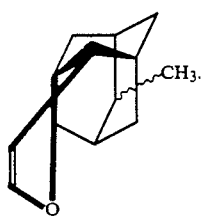

The peak indicated by reference numeral 304 is the peak for the compound having the structure:

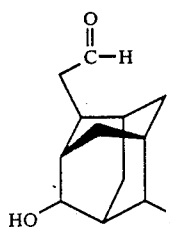

The peak indicated by reference numeral 305 is the peak for the compound having the structure:

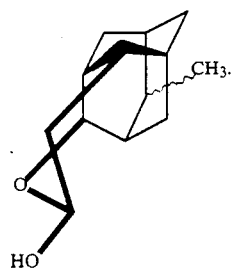

FIG. 31 is the GLC profile for distillation fraction 6 of the foregoing distillation (Conditions: SE-30 column programmed at 130°–220° C. at 8° C. per minute).

FIG. 32 is the GLC profile for distillation fraction 7 of the foregoing distillation (Conditions: SE-30 column programmed at 130°–220° C. at 8° C. per minute).

FIG. 33 is the NMR spectrum for the peak indicated by reference numeral 303 on FIG. 30 for the compound having the structure:

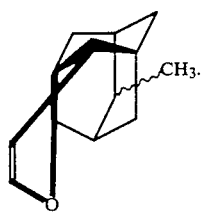

FIG. 34 is the NMR spectrum for the compound having the structure:

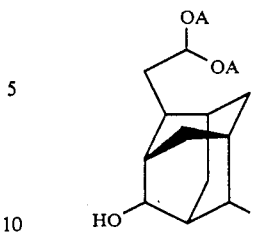

wherein A represents the methyl adamantyloxy moiety.

FIG. 35 is the NMR spectrum for the peak indicated by reference numeral 305 on FIG. 30; for the compound having the structure:

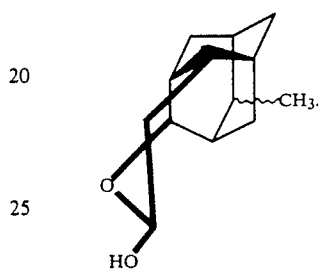

FIG. 36 is the NMR spectrum for distillation fraction 6 of the foregoing distillation showing the existence of the three compounds having the structures:

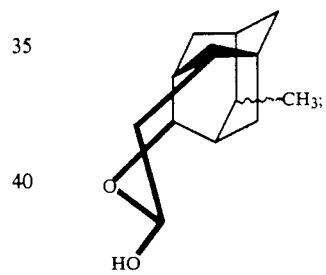

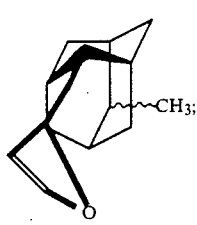

and

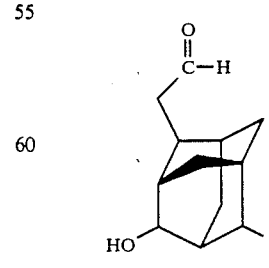

FIG. 37 is the NMR spectrum for distillation fraction 7 of the foregoing distillation.

The mixture of compounds having the structures:

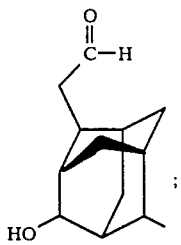

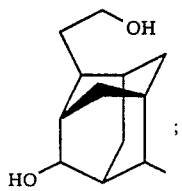

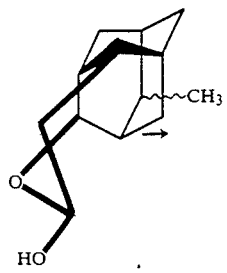

and

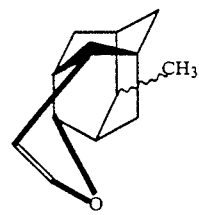

has a green, woody and fir balsum pine-like aroma profile.

EXAMPLE XV

PREPARATION OF ETHERIFIED REACTION PRODUCT OF 2-HYDROXY-4-METHYLENE-8-METHYL TRICYCLO[3.3.1.1$^{3,7}$]DECAN

Reaction:

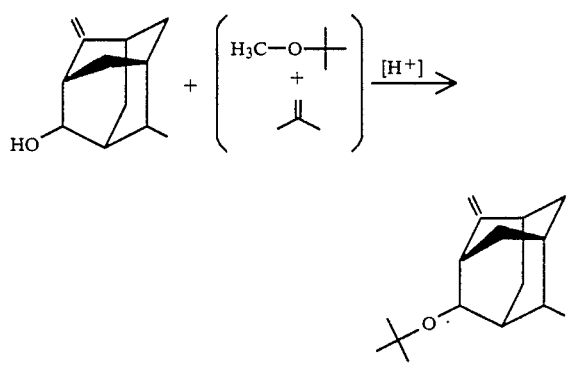

with production of byproducts having the structures:

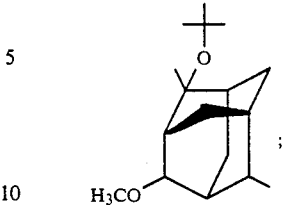

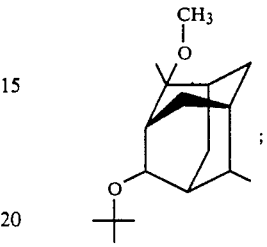

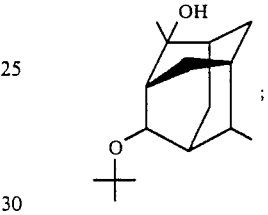

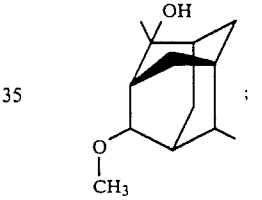

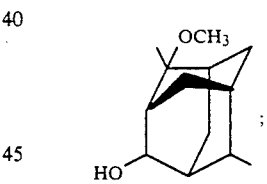

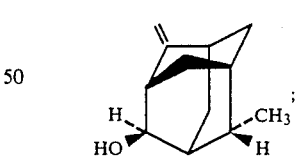

and

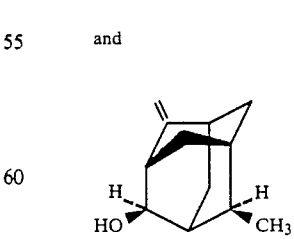

Into a 5 liter reaction vessel equipped with stirrer, thermometer, reflux condenser and heating mantle are placed 120 grams of tertiary butyl methyl ether; 500 grams of the compound having the structure:

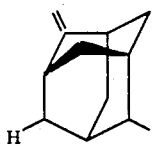

and 115 grams of Amberlyst ® 15 (a styrene sulfonic acid ion exchange catalyst manufactured by the Rome & Haas Company of Philadelphia, Pa. The resulting mixture is heated to 35°–40° C. Over an eight hour period, 1168 grams of isobutylene is added to the reaction mass. At the end of the addition of the isobutylene the reaction mass is cooled and washed with 10% sodium bicarbonate.

The resulting product was fractionally distilled on a stone-packed column yielding the following fractions:

| Fraction No. | Vapor Temp. (°C.) | Liquid Temp. (°C.) | Vacuum mm/Hg. Pressure | Weight of Fraction (Grams) |
|---|---|---|---|---|
| 1 | 42/59 | 73/118 | 220 | |
| 2 | 54 | 142 | 90 | 38 |
| 3 | 80/92 | 116/124 | 2.0/1.6 | 50 |
| 4 | 101 | 128 | 1.6 | 91 |
| 5 | 110 | 143 | 1.6 | 87 |
| 6 | 138 | 178 | 1.3 | 65 |
| 7 | 142 | 208 | 1.2 | 17 |
| 8 | 140 | 214 | 1.1 | |

FIG. 37A is the GLC profile for the reaction product prior to distillation. The peak group indicated by reference numeral 370 is for the compound having the structure:

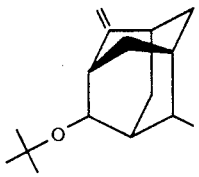

(Conditions: Carbowax column programmed at 130°–220° C. at 8° C. per minute).

FIG. 37B is the GLC profile for distillation fraction 3 of the foregoing distillation. The peak group indicated by reference numeral 371 is for the compound having the structure:

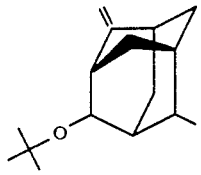

FIG. 38 is the NMR spectrum for peak group 371 of FIG. 37B for distillation fraction 3 of the foregoing distillation; for the compound having the structure:

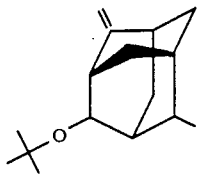

FIG. 37C is the GLC profile for distillation fraction 3 of the foregoing distillation. The peak indicated by reference numeral 372 is the peak for the newly formed isomers of the starting material having the structure:

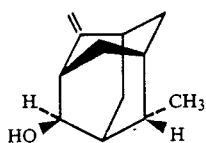

and

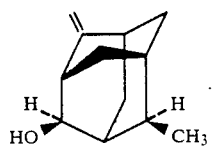

FIG. 39 is the GLC profile for distillation fraction 6 of the foregoing distillation. The peak indicated by reference numeral 391 is the peak for the compound having the structure:

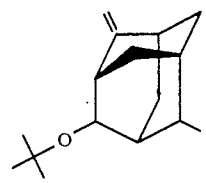

The peak indicated by reference numeral 392 is the peak for one or both of the compounds having the structures:

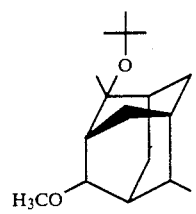

and/or

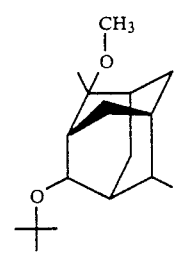

The peak indicated by reference numeral 393 is the peak for the compound having the structure:

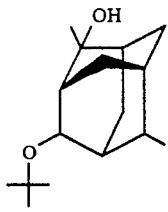

The peak indicated by reference numeral 394 is the peak for the starting materials having the structures:

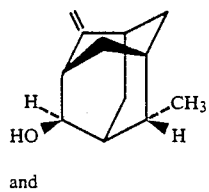

and

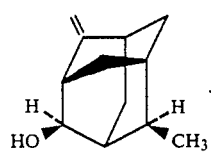

The peak indicated by reference numeral 395 is the peak for one or both of the compounds having the structures:

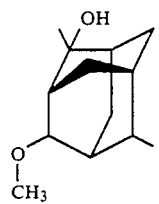

and/or

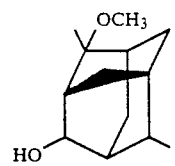

FIG. 40 is the NMR spectrum for the peak indicated by reference numeral 392 of the GLC profile of FIG. 39 for one or both of the compounds having the structures:

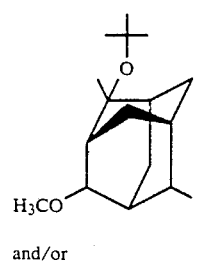

and/or

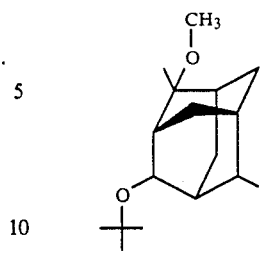

FIG. 41 is the NMR spectrum for the peak indicated by reference numeral 393 of the GLC profile of FIG. 39 for the compound having the structure:

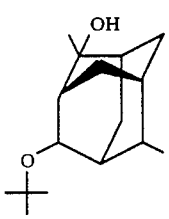

FIG. 42 is the NMR spectrum for the peak indicated by reference numeral 394 of the GLC profile of FIG. 39 for the compounds having the structures:

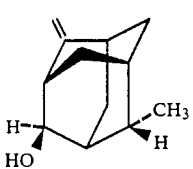

and

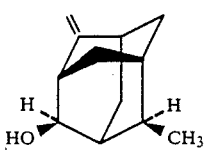

FIG. 43 is the NMR spectrum for the peak indicated by reference numeral 395 of the GLC profile of FIG. 39 for one or both of the compounds having the structures:

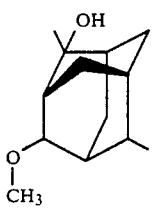

and/or

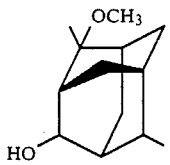

-continued

FIG. 44 is the NMR spectrum for the peak indicated by reference numeral 372 of FIG. 37C for the newly formed isomers of the starting material having the structures:

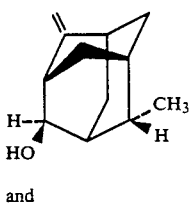

and

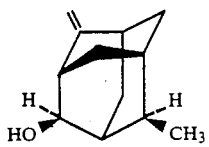

Fraction 6 has an intense and long-lasting camphoraceous aroma with sweet, camphoraceous topnotes.

EXAMPLE XVI

PREPARATION OF 2-METHYOXY-4,8-DIMETHYL-4-METHYLENE-TRICYCLO[3.3.1.1$^{3,7}$]DECANE

Reactions:

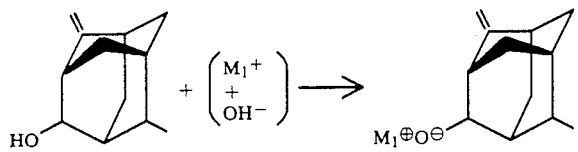

(wherein M$_1$ is sodium) and

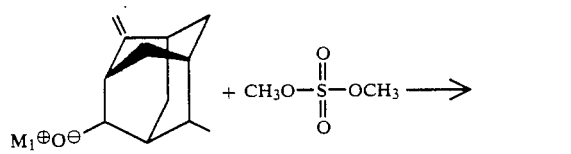

(wherein M$_1$ is sodium).

Into a 250 ml reaction flask equipped with stirrer, thermometer, reflux condenser and heating mantle are placed 40 ml toluene, 50 grams of the compound having the structure:

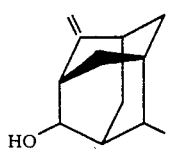

and 1.5 grams of ALIQUAT® 336 (Tricapryl methyl ammonium chloride phase transfer agent produced by Henkel Chemicals Inc. at Minneapo, Minn). The resulting product exotherms 229° C. 49 Grams of 50% aqueous sodium hydroxide is added to the reaction mass. The reaction mass is then heated to 45° C. and 38 grams of dimethyl sulfate is added to the reaction mass with stirring over a period of 0.5 hours during which time the reaction mass temperature goes up to 51° C. The reaction mass is then stirred at 45°-52° C. for a period of eight hours. At the end of the eight hour period, GLC analysis indicates no further conversion.

FIG. 45 is the GLC profile for the crude reaction product. The peak indicated by reference numeral 450 is the peak for the compound having the structure:

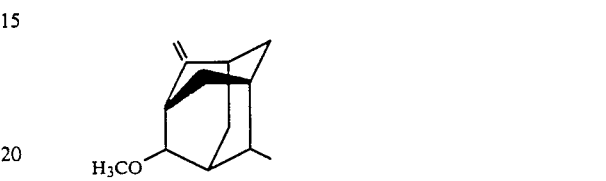

The peak indicated by reference numeral 451 is the peak for the starting material having the structure:

FIG. 46 is the NMR spectrum for the peak indicated by reference numeral 450 of FIG. 45; for the compound having the structure:

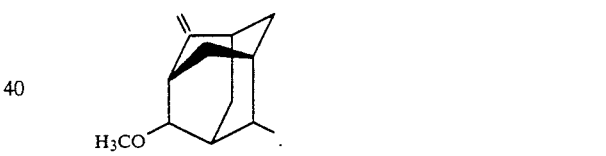

EXAMPLE XVII

PERFUME FORMULATION

The following "woody cologne" perfume formulations are prepared:

|  | XVII (A) | XVII (B) | XVII (C) | XVII (D) |
|---|---|---|---|---|
| Bergamot oil | 150 | 150 | 150 | 150 |
| Orange oil | 200 | 200 | 200 | 200 |
| Lemon oil | 50 | 50 | 50 | 50 |
| Eugenol | 10 | 10 | 10 | 10 |
| 4-(4-Methyl-4-hydroxy amyl) 3 cyclohexene carboxaldehyde | 40 | 40 | 40 | 40 |
| Ylang oil | 2 | 2 | 2 | 2 |
| Petigrain Paraguay | 10 | 10 | 10 | 10 |
| Gamma methyl ionone | 20 | 20 | 20 | 20 |
| Vetiver Venezuela | 18 | 18 | 18 | 18 |
| 3-Alpha-Methyl dodecahydro-6,6,9a-trimethylnaptho-[2,1-b]furan | 5 | 5 | 5 | 5 |
| Product produced by reaction of acetic anhydride polyphosphoric acid and 1,5,9-trimethyl cyclododecatriene- | 5 | 5 | 5 | 5 |

-continued

| | XVII (A) | XVII (B) | XVII (C) | XVII (D) |
|---|---|---|---|---|
| 1,5,9 according to the process of Example I of U.S. Pat. No. 3,718,698 the specification for which is incorporated by reference herein | | | | |
| Octahydro-9,9-dimethyl-1,6-methanonaphthalene-1-(2H)-ol produced according to Example III of U.S. Pat. No. 3,996,169 the specification for which is incorporated by reference herein | 50 | 50 | 50 | 50 |
| The compound having the structure: | 12 | 0 | 0 | 0 |

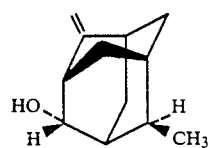

produced according to Example III, bulked fractions 6–9.

| The compound having the structure: | 0 | 12 | 0 | 0 |
|---|---|---|---|---|

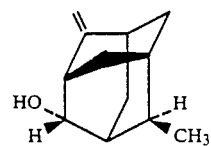

produced according to Example III(A).

| The compound having the structure: | 0 | 0 | 12 | 0 |
|---|---|---|---|---|

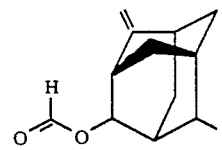

produced according to Example IV, bulked fractions 8–18.

| The compound having the structure: | 0 | 0 | 0 | 12 |
|---|---|---|---|---|

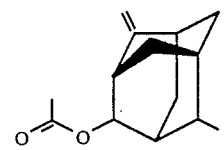

produced according to Example V(B), bulked fractions 7–9.

The compound having the structure

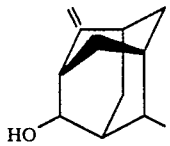

produced according to Example III, imparts to this woody cologne formulation a sandalwood, woody, patchouli, rhubarb, ginger, minty and amyris undertone with amyris, camphoraceous, patchouli, woody and piney topnotes. Accordingly, the perfume formulation of Example XVII(A) can be described as "woody cologne with sandalwood, woody, patchouli, rhubarb, ginger, minty and amyris undertones and amyris, camphoraceous, patchouli, woody and piney topnotes".

The compound having the structure:

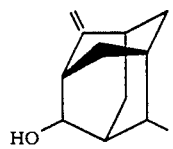

prepared according to Example III(A), imparts to this woody cologne formulation a camphoraceous, ginger, cardamon and woody undertones. Accordingly, the perfume formulation of Example XVII(B) can be described as "woody cologne with camphoraceous, gingery, cardamon and woody undertones".

The compound having the structure:

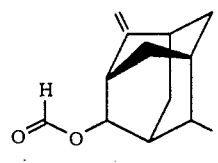

imparts to this woody cologne formulation a woody, cedarwood-like, sandalwood-like, camphoraceous, minty and earthy undertones, with cedarwood, sandalwood, patchouli, camphoraceous, herbaceous, incense and olibanum topnotes. Accordingly, the perfume formulation of Example XVII(C) can be described as "woody cologne with woody, cedarwood-like, sandalwood-like, camphoraceous, minty and earthy undertones and cedarwood, sandalwood, patchouli, camphoraceous, herbaceous, incense and olibanum topnotes".

The compound having the structure:

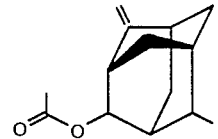

produced according to Example V(B), bulked fractions 7–9, imparts to this woody cologne formulation cedarwood-like, patchouli, vetiver, peppery, grapefruit peel-like and camphoraceous undertones with woody, vetiver, grapefruit peel-like topnotes. Accordingly, the perfume formulation of Example XVII(D) can be described as "woody cologne with cedarwood-like, patchouli, vetiver, peppery, grapefruit peel-like and camphoraceous undertones and woody, vetiver and grapefruit peel-like topnotes".

EXAMPLE XVIII

PINE FRAGRANCE

The following pine fragrance formulations are prepared:

|  | XVIII (A) | XVIII (B) | XVIII (C) | XVIII (D) |
|---|---|---|---|---|
| Isobornyl acetate | 100 | 100 | 100 | 100 |
| Camphor | 10 | 10 | 10 | 10 |
| Alpha-Terpineol | 25 | 25 | 25 | 25 |
| Fir balsam absolute (50% in diethyl phthalate) | 20 | 20 | 20 | 20 |
| Coumarin | 4 | 4 | 4 | 4 |
| Linalool | 30 | 30 | 30 | 30 |
| Fenchyl alcohol | 10 | 10 | 10 | 10 |
| Anethol | 12 | 12 | 12 | 12 |
| Lemon terpenes washed | 50 | 50 | 50 | 50 |
| Borneol | 5 | 5 | 5 | 5 |
| Galbanum oil | 5 | 5 | 5 | 5 |
| Turpentine Russian | 150 | 150 | 150 | 150 |
| Eucalyptol | 50 | 50 | 50 | 50 |
| 2,2,6-trimethyl-1-cyclo-hexene-1-carboxaldehyde | 12 | 12 | 12 | 12 |
| Maltol (1% in diethyl phthalate | 5 | 5 | 5 | 5 |
| The compound having the structure: 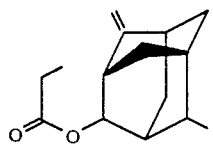 produced according Example VI, bulked fractions 10-16. | 28 | 0 | 0 | 0 |
| The compound having the structure: 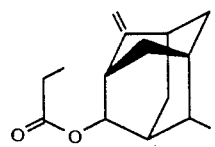 produced according to Example VI, bulked fractions 5-19. | 0 | 28 | 0 | 0 |
| The compound having the structure: 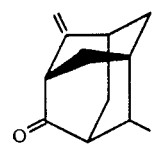 produced according to Example VII, bulked fractions 4-8. The compound having the structure: | 0 | 0 | 28 | 0 |

|  | XVIII (A) | XVIII (B) | XVIII (C) | XVIII (D) |
|---|---|---|---|---|
| 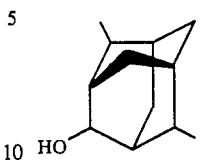 produced according to Example X, bulked fractions 4 and 5. | | | | |

The compound having the structure:

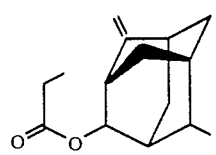

prepared according to Example VI, bulked fractions 10-16 imparts to this pine formulation a woody, rose-like and peony-like undertone, with floral, sweet pea, rose and peony topnotes. Accordingly, the perfume formulation of Example XVIII(A) can be described as "piney, with woody, rose-like and peony-like undertones and floral sweet pea, rose and peony topnotes".

The compound having the structure:

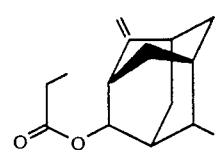

prepared according to Example VI, bulked fractions 5-19 imparts to this pine formulation an ambery, woody, cedarwood-like undertone with fruity and woody topnotes. Accordingly, the perfume formulation of Example XVIII(B) can be described as "piney with ambery, woody and cedarwood-like undertones and fruity and woody topnotes".

The compound having the structure:

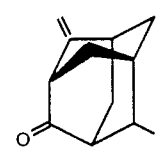

prepared according to Example VII bulked fractions 4-8 imparts to this piney formulation camphoraceous undertones with early morning forest path, green, piney, woody and camphoraceous topnotes. Accordingly, the perfume formulation of Example XVIII(C) can be described as "piney with camphoraceous undertones and early morning forest path, green, piney, woody and camphoraceous topnotes".

The compound having the structure:

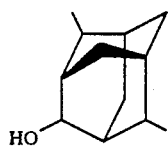

produced according to Example X bulked fractions 4 and 5 imparts to this piney formulation spicy, ginger root, rosemary and camphoraceous undertones with green, woody and ginger root topnotes. Accordingly, the perfume formulation of Example XVIII(D) can be described as "piney with spicy, ginger root, rosemary and camphoraceous undertones and green, woody and ginger root topnotes".

EXAMPLE XIX

FLORAL PERFUME COMPOSITIONS

The following floral fragrance formulations are prepared:

| | FLORAL FRAGRANCE | | | |
|---|---|---|---|---|
| | XIX (A) | XIX(B) | XIX(C) | XIX(D) |
| Citronellol | 12.3 | 12.3 | 12.3 | 5.0 |
| Geraniol | 2.5 | 2.5 | 2.5 | 5.0 |
| Amyl Cinnamic Aldehyde | 24.6 | 24.6 | 24.6 | 5.0 |
| Galaxolide ® 50 (Trademark for Tricyclic Isochroman of International Flavors & Fragrances Inc.) | 9.8 | 9.8 | 9.8 | 5.0 |
| Vertenex High Cis (Cis-t-Butylcyclo hexenyl Acetate; Para Isomer) | 7.4 | 7.4 | 7.4 | 5.0 |
| Rose Oxide | 0.7 | 0.7 | 0.7 | 5.0 |
| Cinnamic Alcohol | 19.6 | 19.6 | 19.6 | 5.0 |
| Aldehyde C-11 (n-Undecylenic Aldehyde) | 0.5 | 0.5 | 0.5 | 5.0 |
| Aldehyde C-12 (n-Dodecyl Aldehyde in 10% solution in diethyl phthalate) | 0.5 | 0.5 | 0.5 | 5.0 |
| Citronellal (10% solution in diethyl phthalate) | 0.5 | 0.5 | 0.5 | 5.0 |
| Phenyl Ethyl Acetate | 2.5 | 2.5 | 2.5 | 5.0 |
| Ylang Oil | 1.2 | 1.2 | 1.2 | 5.0 |
| Indisan (Hydrogenated derivative of reaction product of Camphene and Resorcinol) | 3.7 | 3.7 | 3.7 | 5.0 |
| Musk Ketone | 5.0 | 5.0 | 5.0 | 5.0 |
| Oakmoss Resin | 0.5 | 0.5 | 0.5 | 0.5 |
| Liatrix Absolute (10% in diethyl phthalate) | 2.5 | 2.5 | 2.5 | 5.0 |
| Vetiver Acetate | 1.2 | 1.2 | 1.2 | 5.0 |
| Diethyl Phthalate | 5.0 | 5.0 | 5.0 | 5.0 |
| The mixture of compounds having the structures: | | | | |

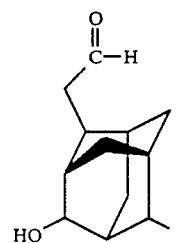

| | FLORAL FRAGRANCE | | | |
|---|---|---|---|---|
| | XIX (A) | XIX(B) | XIX(C) | XIX(D) |
| and | 0.0 | 0.0 | 15.0 | 0.0 | produced according to Example XIV, fraction 6.
Mixture of compounds having the structures:

-continued

FLORAL FRAGRANCE

| | XIX (A) | XIX(B) | XIX(C) | XIX(D) |
|---|---|---|---|---|
| 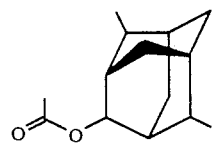 and 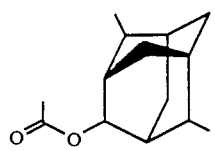 prepared according to Example XV. | 0.0 | 0.0 | 0.0 | 35.0 |

The compound having the structure:

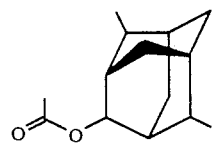

produced according to Example XI, bulked fractions 5–9 imparts to this floral fragrance formulation woody, ambery, vetiver, cedarwood, piney and chrysanthemum-like undertones with woody, amber and olibanum topnotes. Accordingly, the fragrance formulation of Example XIX(A) can be described as "floral with woody, amber, vetiver, cedarwood, piney and chrysanthemum-like undertones and woody, amber and olibanum topnotes".

The compound having the structure:

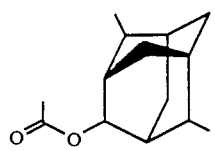

prepared according to Example XIII, bulked fractions 2–18 imparts to this floral fragrance a woody, amber, vetiver, cedarwood, piney and chrysanthemum-like undertone, with woody, amber and olibanum topnotes. Accordingly, the fragrance formulation of Example XIX(B) can be described as "floral with woody, amber, vetiver, cedarwood, piney and chrysanthemum-like undertones and woody, amber, olibanum topnotes".

The mixture of compounds having the structures:

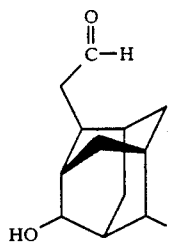

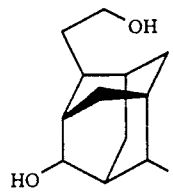

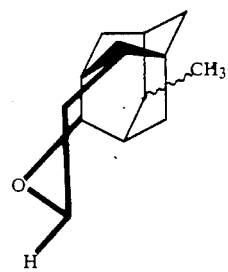

and

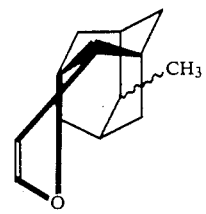

prepared according to Example XIV, fraction 6 imparts to this floral formulation a green, woody and fir balsam-like undertones. Accordingly, the fragrance formulation of Example XIX(C) can be described as "floral with green, woody and fir balsam-like undertones".

The mixture of compounds having the structures:

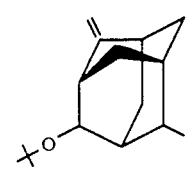

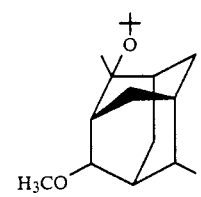

-continued

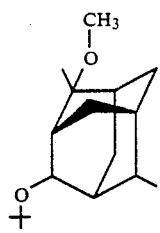

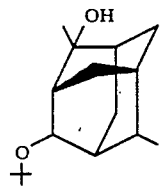

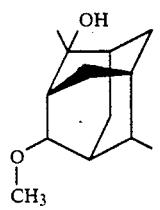

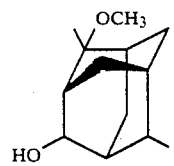

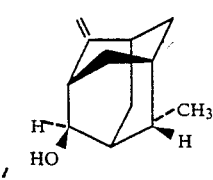

and

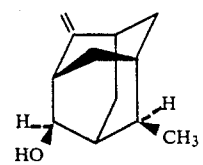

produced according to Example XV, imparts to this floral fragrance a camphoraceous undertone with sweet camphoraceous topnotes. Accordingly, the fragrance formulation of Example XIX(D) can be described as "floral with a camphoraceous undertone and sweet camphoraceous topnotes".

EXAMPLE XX

PREPARATION OF COSMETIC POWDER COMPOSITIONS

Cosmetic powder compositions are prepared by mixing in a ball mill 100 grams of talcum powder with 0.25 grams of each of the substances set forth in Table II below. Each of the cosmetic powder compositions has an excellent aroma as described in Table II below:

TABLE II

| SUBSTANCE | AROMA DESCRIPTION |
|---|---|
| The compound having the structure: [structure] produced according to Example III, bulked fractions 6-9. | A sandalwood, woody, patchouli, rhubarb, ginger, minty and amyris aroma profile with amyris, camphoraceous, patchouli, woody and piney topnotes. |
| The compound having the structure: [structure] produced according to Example III(A). | A camphoraceous, gingery, cardamon and woody profile. |
| The compound having the structure: [structure] produced according to Example IV, bulked fractions 8-18. | A woody, cedarwood-like, sandalwood-like, camphoraceous, minty and earthy aroma profile with cedarwood, sandalwood, patchouli, camphoraceous, herbaceous, incense and olibanum topnotes. |
| The compound having the structure: [structure] prepared according to Example V(B), bulked fractions 7-9. | A cedarwood-like, patchouli, vetiver, peppery, grapefruit peel-like and camphoraceous aroma profile, with woody, vetiver and grapefruit peel topnotes. |
| The compound having the structure: [structure] produced according to Example VI, bulked fractions 10-16. | A woody, rose-like and peony-like aroma profile, with floral, sweet pea, rose and peony topnotes. |
| The compound having the structure: [structure] produced according to Example VI, bulked fractions 5-19. | An ambery, woody and cedarwood-like aroma profile, with fruity and woody topnotes. |
| The compound having the structure: | A camphoraceous aroma with early morning forest path, |

TABLE II-continued

| SUBSTANCE | AROMA DESCRIPTION |
|---|---|
| [structure] produced according to Example VII, bulked fractions 4–8. | green, piney, woody and camphoraceous topnotes. |
| The compound having the structure: [structure with HO] produced according to Example X, bulked fractions 4 and 5. | A spicy, ginger root, rosemary and camphoraceous aroma profile, with green, woody and ginger root topnotes. |
| The compound having the structure: [acetate structure] produced according to Example XI, bulked fractions 5–9. | A woody, ambery, vetiver, cedarwood, piney and chrysanthemum-like aroma profile, with woody, amber and olibanum topnotes. |
| The compound having the structure: [acetate structure] produced according to Example XIII, bulked fractions 2–18. | A woody, amber, vetiver, cedarwood, piney and chrysanthemum-like aroma profile, with woody, amber and olibanum topnotes. |
| Mixture of compounds having the structures: [aldehyde-HO structure] [OH structure] | A green, woody and fir balsam-like aroma profile. |
| [CH3/HO structure] and [CH3/O structure] produced according to Example XIV, distillation fraction 6. | |
| Mixture of compounds having the structures: [several structures with OtBu, OMe, OH groups] | A camphoraceous aroma with sweet, camphoraceous topnotes. |

TABLE II-continued

| SUBSTANCE | AROMA DESCRIPTION |
|---|---|
| 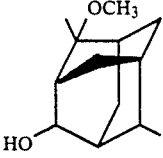produced according to Example XV. | |
| Fragrance formulation of Example XVII(A). | Woody cologne with sandalwood, woody, patchouli, rhubarb, ginger, minty and amyris undertones and amyris, camphoraceous, patchouli, woody and piney topnotes. |
| Fragrance formulation of Example XVII(B). | Woody cologne with camphoraceous, gingery, cardamon and woody undertones. |
| Fragrance formulation of Example XVII(C). | Woody cologne with woody, cedarwood-like, sandalwood-like, camphoraceous, minty and earthy undertones and cedarwood, sandalwood, patchouli, camphoraceous, herbaceous, incense and olibanum topnotes. |
| Fragrance formulation of Example XVII(D). | Woody cologne with cedarwood-like, patchouli, vetiver, peppery, grapefruit peel-like, and camphoraceous undertones and woody, vetiver and grapefruit peel-like topnotes. |
| Fragrance formulation of Example XVIII(A). | Piney, with woody, rose-like and peony-like undertones and floral sweet pea, rose and peony topnotes. |
| Fragrance formulation of Example XVIII(B). | Piney with ambery, woody and cedarwood-like undertones and fruit and woody topnotes. |
| Fragrance formulation of Example XVIII(C). | Piney with camphoraceous undertones and early morning forest path, green, piney, woody and camphoraceous topnotes. |
| Fragrance formulation of Example XVIII(D). | Piney with spicy, ginger root, rosemary and camphoraceous undertones and green, woody and ginger root topnotes. |
| Fragrance formulation of Example XIX(A). | Floral with woody, amber, vetiver, cedarwood, piney and chrysanthemum-like undertones and woody, amber and olibanum topnotes. |
| Fragrance formulation of Example XIX(B). | Floral with woody, amber, vetiver, cedarwood, piney and chrysanthemum-like undertones and woody, amber, olibanum topnotes. |
| Fragrance formulation of Example XIX(C). | Floral with green, woody and fir balsam-like undertones. |
| Fragrance formulation of Example XIX(D). | Floral with a camphoraceous undertone and sweet camphoraceous topnotes. |
| The compound having the structure:prepared according to Example XII, bulked fractions 4–6. | A fresh, camphoraceous, sage-like and woody aroma profile, with camphoraceous and woody topnotes. |
| The compound having the structure: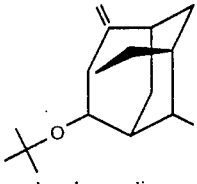produced according to Example XVI. | A natural, fresh pine, forest aroma profile. |

EXAMPLE XXI

PERFUMED LIQUID DETERGENT

Concentrated liquid detergents with aromas as set forth in Table II of Example XX (which detergents are prepared from Lysine salt of n-dodecyl benzene sulfonic aicd as more specifically described in the U.S. Pat. No. 3,948,818 issued on Apr. 6, 1976, the specification for which is incorporated by reference herein) are prepared containing each of the substances set forth in Table II of Example XX, supra. They are prepared by adding and homogeneously mixing the appropriate quantity of perfumery substance as set forth in Table II of Example XX in the liquid detergent. The detergents all possess aromas as set forth in Table II of Example XX, the intensity increasing with greater concentrations of perfumery substance of Table II of Example XX, supra.

EXAMPLE XXII

PREPARATION OF A COLOGNE AND HANDKERCHIEF PERFUME

The perfume substances of Table II of Example XX, supra, are incorporated into colognes at concentrations of 1.5%, 2.0%, 2.5%, 3.0% and 4.0% in 80%, 85and 90% aqueous ethanol; and into a handkerchief perfume composition at concentrations of 10%, 15%, 20%, 25% and 30% (in 85%, 90% and 95% aqueous ethanol). Distinct and definitive aromas as set forth in Table II of Example XX are imparted to the cologne and to the handkerchief perfume compositions.

EXAMPLE XXIII

PREPARATION OF A DETERGENT COMPOSITION

A total of 100 grams of a detergent powder (a nonionic detergent powder containing a proteolytic enzyme prepared according to Example I of Canadian Letters Patent No. 985,190 issued on Mar. 9, 1976, the disclosure of which is incorporated by reference herein) is mixed with 0.15 grams of each of the substances homogeneous compositions are obtained. These compositions have excellent aromas as set forth in Table II of Example XX.

EXAMPLE XXIV

PREPARATION OF SOAP

Each of the perfumery substances of Table II of Example XX are incorporated into soap (LVU-1) at 0.1% by weight of each substance. After two weeks in the oven at 90° F., each of the soaps showed no visual effect from the heat. Each of the soaps manifested an excellent aroma as set forth in Table II of Example XX, supra.

EXAMPLE XXV

PREPARATION OF SOAP COMPOSITION

One hundred grams of soap chips (IVORY ®, registered trademark of the Procter & Gamble Co. of Cincinnati, Ohio) are mixed individually with one gram each of the perfumery substances of Table II of Example XX, supra, until a homogeneous composition is obtained. The homogeneous composition is then treated under three atmospheres pressure at 180° C. for a period of three hours and the resulting liquid is placed into a soap mold. the resulting soap cakes, on cooling, manifest excellent aromas as set forth in Table II of Example XX, supra.

EXAMPLE XVI

PREPARATION OF A SOLID DETERGENT COMPOSITION

A detergent is prepared from the following ingredients according to Example I of Canadian Letters Patent No. 1,007,948, the specification for which is incorporated by reference herein.

| Ingredients | Parts by Weight |
| --- | --- |
| "Neodol 45-11" (a $C_{14}$–$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a "phosphate-free" detergent. A total of 100 grams of this detergent is admixed separately with 0.15 grams of each of the perfume substances of Table II of Example XX, supra. The detergent samples each have excellent aromas as set forth in Table II of Example XX, supra.

EXAMPLE XXVII

Utilizing the procedure os Example I at column 15 of U.S. Pat. No. 3,632,396 (the specification for which is incorporated by reference herein), a non-woven cloth substrate useful as a dryer-added fabric softening article of manufacture is prepared, wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.);
   57% $C_{20\text{-}22}$ HAPS;
   22% isopropyl alcohol;
   20% antistatic agent;
   1% of one of the perfume substances of Table II of Example XX, supra.

A fabric softening composition prepared as set forth above having the above aroma characteristics as set forth in Table II of Example XX, supra, essentially consists of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of substrate. The aroma set forth in Table II of Example XX is imparted in a pleasant manner to the headspace in the dryer on operation thereof, using said dryer-added fabric softening non-woven fabric.

EXAMPLE XXVIII

TOBACCO FLAVOR FORMULATION

Cigarettes are produced using the following tobacco formulation:

| Ingredients | Parts by Weight |
| --- | --- |
| Bright | 40.1 |
| Burley | 24.9 |
| Maryland | 1.1 |
| Turkish | 11.6 |
| Stem (flue-cured) | 14.2 |
| Glycerine | 2.8 |
| $H_2O$ | 5.3 |
| Ethyl butyrate | .05 |
| Ethyl valerate | .05 |
| Maltol | 2.00 |
| Cocoa Extract | 26.00 |
| Coffee Extract | 10.00 |
| Ethyl Alcohol (95%) | 20.00 |
| $H_2O$ | 41.90 |

To 50% of the cigarettes, 10 and 20 ppm of one of the compounds set forth in Table III are added. These cigarettes are hereinafter called "experimental" cigarettes and the cigarettes without the adamantane derivatives in the following table are hereinafter called "control" cigarettes. The control and experimental cigarettes are then evaluated by paired comparison and the results are as set forth in Table III below.

All cigarettes both control and experimental are evaluated for smoke flavor with 20 mm cellulose acetate filters.

TABLE III

| Adamantane Derivative | Smoking Tobacco Flavor Evaluation |
| --- | --- |
| The compound having the structure: | An intense, oriental Turkish-like flavor with |

TABLE III-continued

| Adamantane Derivative | Smoking Tobacco Flavor Evaluation |
|---|---|
| 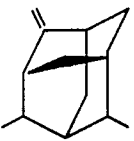 produced according to Example III, bulked fractions 6-9. | patchouli and gingery nuances both prior to and on smoking. |
| The compound having the structure: 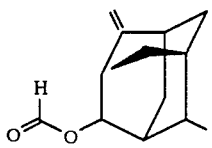 produced according to Example IV, bulked fractions 8-18. | An oriental/incense aroma and taste prior to and on smoking causing the Virginia tobacco to have "Turkish tobacco" nuances on smoking. |
| The compound having the structure: 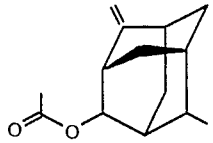 prepared according to Example V(B), bulked fractions 7-9. | An oriental aroma and taste prior to and on smoking in the main stream and in the side stream causing the Virginia-like tobaccos to be more "Turkish-like". Also present are pleasant vetiver-like nuances. |

EXAMPLE XXIX

A fabric washing deodorant detergent powder product is prepared by admixing the following ingredients:

| Ingredients | Parts by Weight |
|---|---|
| Linear alkylbenzene sulfonate | 9.0 |
| $C_{13}$-$C_{15}$ straight chain alcohols (30:30:40 mixture of $C_{13}$, $C_{14}$ and $C_{15}$ straight chain alcohol) | 4.0 |
| Sodium tripolyphosphate | 16.0 |
| ZEOLIGHT ® | 8.0 |
| Sodium silicate | 4.0 |
| Magnesium silicate | 0.8 |
| Ethylene diamine | 0.6 |
| N,N,N',N'[tetra(methylene phosphonic acid)] sodium carboxy methyl cellulose | 0.9 |
| Anti-foam | 1.5 |
| Sodium Perborate tetrahydrate | 14.0 |
| N,N,N'N'-Tetraacetyl Glycoluril | 4.2 |
| The compound having the structure: 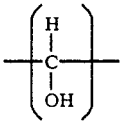 prepared according to Example XVI. | 4.45 |
| Water | 45.0 |
| Sodium sulfate | 5.0 |

The resulting fabric washing deodorant detergent powder on use gives rise to a very pleasant "fresh pine forest" aroma without any aesthetically displeasing aromas susequent to washing of fabrics in the standard washing machine cycle.

Dodorant detergent products have also been prepared according to Examples I-IX of U.S. Pat. No. 4,304,679 incorporated by reference herein.

Thus, exemplified herein by reference are the following:

(a) a deodorant detergent product comprising:
  (i) from 0.5 to 99.99% by weight of a non-soap detergent active compound; and
  (ii) from 0.01 to 10% by weight of a deodorant composition comprising from 45 to 100% by weight of at least one adamantane derivative of our invention having the structure:

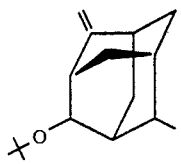

(prepared according to Example XVI) or the adamantane derivative of our invention having the structure:

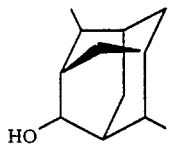

produced according to Example X, supra, bulked fractions 4 and 5; said adamantane derivative having a lipoxidase-inhibiting capacity of at least 50% or a Raoult variance ratio of at least 1.1 as stated in said U.S. Pat. No. 4,304,679, with the adamantane derivatives having the structures:

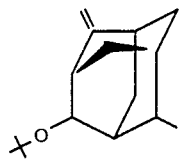

and

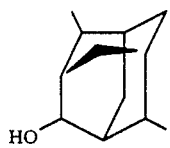

having deodorant values of from 0.5 to 3.5 as measured by the deodorant value test as specifically set forth in said U.S. Pat. No. 4,304,679 and exemplified therein.

Furthermore, the examples of U.S. Pat. No. 4,663,068 are also incorporated herein by reference.

(i) from 5 to 40% by weight of a non-soap detergent active compound comprising an anionic detergent active compound;
(ii) from 1 to 90% of a non-soap detergency builder;

(iii) from 1 to 30% by weight a peroxy bleach compound together with an activator therefor;

(iv) from 0.1 up to 10% by weight of a bleach stable perfume which comprises 50-100% by weight of at least one bleach stable adamantane derivative having the structures:

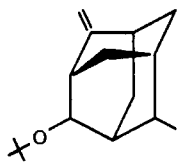

and

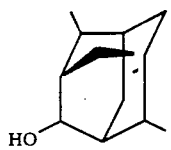

having a Lipoxidase-inhibiting capacity of at least 50% or a Raoult variance ratio of at least 1.1 as defined accordig to U.S. Pat. No. 4,663,068 incorporated by reference herein, with the adamantane derivatives being stable in the presence of sodium perborate tetrahydrate or any other alkali metal perborate tetrahydrate ad N,N,N',N'-tetraacetyl ethylenediamine (TEAD) according to the bleach stability test as defied in said U.S. Pat. No. 4,663,068 incorporated by reference herein, the bleach stable deodorant schiff base having a Malodor Reduction Value of from 0.25 up to 3.0 as measured by the Malodor Reduction Value test defined in said U.S. Pat. No. 4,663,068 incorporated by reference herein.

The peroxy bleach activator may be exemplified by the following peroxy bleach activators:
N,N,N',N'-tetraacetyl ethylenediamine;
N,N,N',N'-tetraacetyl glycoluril;
Glucose pentaacetate;
Sodium acetoxybenzene sulphonate;
Sodium nonanoyloxybenzene sulphonate;
Sodium octanoyloxybenzene sulphonate; and
mixtures thereof.

The non-soap anionic detergent active compound may be selected from the group consisting of sodium and potassium alkyl sulphates, sodium potassium and ammonium alkyl benzene sulphonates, sodium alkyl glyceryl ether sulphates, sodium coconut oil fatty acids monoglyceride sulphates and sulphonates, sodium and potassium salts of sulphuric acid esters of higher ($C_9$-$C_{18}$) fatty alcohol-alkylene oxide, the reaction products of fatty acids esterified with isethionic acid and neutralized with sodium hydroxide, sodium and potassium salts of fatty acid amides of methyl taurine, alkane monosulphonates, olefin sulphonates and mixtures thereof.

The nonionic detergent active compound may be selected from the group consisting of reaction products of alkylene oxides with alkyl ($C_6$-$C_{22}$) phenols, the condensation products of aliphatic ($C_8$-$C_{18}$) primary or secondary linear or branched alcohols with ethylene oxide, producs made by condensation of ethylene oxide with the reaction products of propylene oxide and ethylene diamine, long-chain tertiary amine oxides, lonechain phosphine oxides and dialkyl sulphoxides and mixtures thereof.

What is claimed is:

1. A deodorant detergent product comprising:
   (i) from 0.5 to 99.99% by weight of a non-soap detergent active compound; and
   (ii) from 0.01% to 10% by weight of a deodorant composition comprising from 45 to 100% by weight of at least one adamantane derivative defined according to the structure:

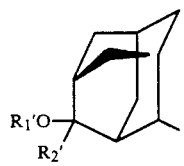

wherein $R_1'$ is hydrogen or acetyl; $R_2'$ is hydrogen or lower alkyl; and the dashed line represents a carbon-carbon single bond or a carbon-carbon double bond.

2. A deodorant detergent powder product suitable for use in the washing of fabrics which comprises:
   (i) from 5 to 40% by weight of a non-soap detergent active compound comprising an anionic detergent active compound;
   (ii) from 1 to 90% by weight of a non-soap detergency builder;
   (iii) from 1 to 30% by weight of a peroxy bleach compound together with an activator therefor; and
   (iv) from 0.1 up to 5% of a bleach stable deodorant perfume which comprises 50 to 100% of at least one adamantane derivative defined according to the structure:

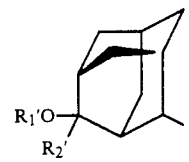

wherein $R_1'$ is hydrogen or acetyl; $R_2'$ is hydrogen or lower alkyl and the dashed line represents a carbon-carbon single bond or a carbon-carbon double bond.

3. The adamantane derivative defined according to the structure:

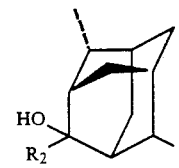

wherein $R_2$ is lower alkyl and wherein the dashed line is a carbon-carbon single bond or a carbon-carbon double bond.

4. The adamantane derivative of claim 3 having the structure:

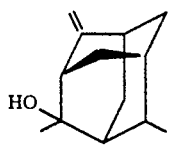

5. A process for augmenting or enhancing the aroma or taste of a consumable material selected from the group consisting of perfume compositions, perfumed articles, colognes, smoking tobacco compositions, smoking tobacco articles, deodorizing articles, deodorizing compositions and malodor maskants comprising the step of adding to said consumable material an aroma or taste augmenting or enhancing quantity of at least one adamantane derivative defined according to the generic structure:

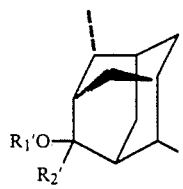

wherein $R_1'$ is hydrogen or acetyl; $R_2'$ is hydrogen or lower alkyl and the dashed line is a carbon-carbon single bond or a carbon-carbon double bond.

6. The process of claim 5 wherein the consumable material is a perfume composition, perfumed article or cologne.

7. The process of claim 6 wherein the adamantane derivative is a compound having the structure:

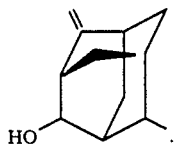

8. The process of claim 6 wherein the adamantane derivative is a compound having the structure:

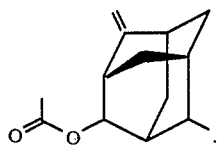

9. The process of claim 6 wherein the adamantane derivative is a compound having the structure:

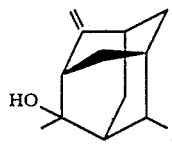

10. The process of claim 5 wherein the consumable material is a smoking tobacco composition or smoking tobacco article.

11. The process of claim 6 wherein the adamantane derivative is a compound having the structure:

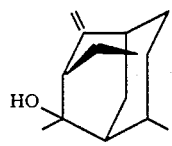

* * * * *